(12) United States Patent
Scadden et al.

(10) Patent No.: US 10,906,980 B2
(45) Date of Patent: *Feb. 2, 2021

(54) COMPOSITIONS AND METHODS FOR NON-MYELOABLATIVE CONDITIONING

(71) Applicants: President and Fellows of Harvard College, Cambridge, MA (US); The General Hospital Corporation, Boston, MA (US); The Children's Medical Center Corporation, Boston, MA (US)

(72) Inventors: David T. Scadden, Weston, MA (US); Rahul Palchaudhuri, Cambridge, MA (US); Derrick J. Rossi, Newton, MA (US); Agnieszka D. Czechowicz, Boston, MA (US)

(73) Assignees: President and Fellows of Harvard College, Cambridge, MA (US); The General Hospital Corporation, Boston, MA (US); The Children's Medical Center Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/726,803

(22) Filed: Dec. 24, 2019

(65) Prior Publication Data

US 2020/0148776 A1    May 14, 2020

Related U.S. Application Data

(63) Continuation of application No. 16/205,205, filed on Nov. 29, 2018, now Pat. No. 10,570,207, which is a continuation of application No. 15/148,837, filed on May 6, 2016, now Pat. No. 10,280,225, which is a continuation of application No. PCT/US2016/026276, filed on Apr. 6, 2016.

(60) Provisional application No. 62/239,573, filed on Oct. 9, 2015, provisional application No. 62/221,595, filed on Sep. 21, 2015, provisional application No. 62/220,204, filed on Sep. 17, 2015, provisional application No. 62/143,642, filed on Apr. 6, 2015.

(51) Int. Cl.
| | |
|---|---|
| *A61K 38/36* | (2006.01) |
| *A61K 39/385* | (2006.01) |
| *C07K 4/04* | (2006.01) |
| *C07K 16/28* | (2006.01) |
| *A61K 35/28* | (2015.01) |
| *A61K 38/16* | (2006.01) |
| *G01N 33/50* | (2006.01) |
| *A61K 47/68* | (2017.01) |
| *G01N 33/569* | (2006.01) |
| *G01N 33/574* | (2006.01) |

(52) U.S. Cl.
CPC .......... *C07K 16/2866* (2013.01); *A61K 35/28* (2013.01); *A61K 38/164* (2013.01); *A61K 38/168* (2013.01); *A61K 47/6825* (2017.08); *A61K 47/6849* (2017.08); *A61K 47/6898* (2017.08); *C07K 4/04* (2013.01); *C07K 16/289* (2013.01); *G01N 33/50* (2013.01); *G01N 33/56966* (2013.01); *G01N 33/57407* (2013.01); *G01N 33/57434* (2013.01)

(58) Field of Classification Search
None
See application file for complete search history.

(56) References Cited

U.S. PATENT DOCUMENTS

| | | | |
|---|---|---|---|
| 10,280,225 B2 | 5/2019 | Scadden et al. | |
| 2009/0148904 A1 | 6/2009 | Mayfield | |
| 2009/0191202 A1 | 7/2009 | Jamieson et al. | |
| 2010/0226927 A1 | 9/2010 | Weissman et al. | |
| 2011/0189209 A1 | 8/2011 | Neville, Jr. et al. | |
| 2011/0243841 A1 | 10/2011 | Chang et al. | |
| 2012/0288506 A1 | 11/2012 | Amatulli et al. | |
| 2016/0152733 A1 | 6/2016 | Thie et al. | |
| 2016/0222348 A1 | 8/2016 | Boehm et al. | |
| 2019/0100593 A1 | 4/2019 | Scadden et al. | |

FOREIGN PATENT DOCUMENTS

| | | |
|---|---|---|
| WO | WO-95/13093 A1 | 5/1995 |
| WO | WO-1999/024078 | 5/1999 |
| WO | WO-2004/002425 A2 | 1/2004 |
| WO | WO-2005026210 A2 | 3/2005 |
| WO | WO-2005/046711 A2 | 5/2005 |
| WO | WO-2008/067115 A2 | 6/2008 |
| WO | WO-2009/064815 A1 | 5/2009 |

(Continued)

OTHER PUBLICATIONS

Notice of Allowance from U.S. Appl. No. 16/205,205, dated Dec. 31, 2019.

Alexander, et al., "Depletion of Autoreactive Immunologic Memory Followed by Autologous Hematopoietc Stem Cell Transplantation in Patients with Refractory SLE Induces Long-Term Remission Through de novo Generation of a Juvenile and Tolerant Immune System," *Blood*, 113 (1):214-223 (Jan. 1, 2009).

Applebaum, "Immunobiologic Therapies for Myelodysplastic Syndrome," *Best Practice & Research Clinical Haematology*, 17(4):653-661, (Dec. 2004).

(Continued)

*Primary Examiner* — Michail A Belyavskyi
(74) *Attorney, Agent, or Firm* — Morse, Barnes-Brown & Pendleton, P.C.; Lisa M. Warren, Esq.

(57) ABSTRACT

Disclosed herein are non-myeloablative antibody-toxin conjugates and compositions that target cell surface markers, such as the CD34, CD45 or CD117 receptors, and related methods of their use to effectively conditioning a subject's tissues (e.g., bone marrow tissue) prior to engraftment or transplant. The compositions and methods disclosed herein may be used to condition a subject's tissues in advance of, for example, hematopoietic stem cell transplant and advantageously such compositions and methods do not cause the toxicities that are commonly associated with traditional conditioning methods.

30 Claims, 42 Drawing Sheets

(56) References Cited

FOREIGN PATENT DOCUMENTS

| WO | WO-2010115629 A2 | 10/2010 |
|---|---|---|
| WO | WO-2013/023015 A2 | 2/2013 |
| WO | WO-2013/126690 A1 | 8/2013 |
| WO | WO-2014/134539 A1 | 9/2014 |
| WO | WO-2015067667 A1 | 5/2015 |
| WO | WO-2016/016442 A1 | 2/2016 |
| WO | WO-2016/033201 A1 | 3/2016 |
| WO | WO-2016/071856 A1 | 5/2016 |
| WO | WO-2016/164502 A1 | 10/2016 |

OTHER PUBLICATIONS

Advanced Targeting Systems, Product Catalog, Molecular Surgery for Scientists, pp. 1-59, (2010).
Bhattacharya, et al., "Niche Recycling Through Division-Independent Egress of Hematopoietic," *J. Exp. Med.*, 206(12):2837-2850, (2009).
Burt, et al., "Treatment of Autoimmune Disease by Intense Immunosuppressive Conditioning and Autologous Hematopoietic Stem Cell Transplantation," *Blood Journal*, 92(10):3505-3514, (Nov. 15, 1998).
Chandrasekaran, et al. "Modeling Promising Nonmyeloablative Conditioning Regiments in Nonhuman Primates," *Human Gene Therapy*, 25:1013-1022, (Dec. 2014).
Chen, et al., "Durable Donor Engraftment After Radioimmunotherapy Using α-Emitter Astatine-211-Labeled Anti-CD45 Antibody for Conditioning in Allogeneic Hematopoietic Cell Transplantation," *Blood*, 119(5):1130-1138, (2012).
Chen, et al., "Mobilization as a Preparative Regiment for Hematopoietic Stem Cell Transplantation," *Blood*, 107(9):3764-3771, (2006).
Czechowicz, et al., "Efficient Transplantation via Antibody-Based Clearance of Hematopoietic Stem Cell Niches," *Science*, 318:1296-1299, (2007).
Derderian, et al., "In Utero Depletion of Fetal Hematopoietic Stem Cells Improves Engraftment After Neonatal Transplantation in Mice," *Blood Journal*, 124(6):973-980, (Aug. 7, 2014).
Fujisaki, et al., "In vivo imaging of Tregs Providing Immune Privilege to the Hematopoietic Stem Cell Niche," *Nature*, 474(7350):216-219, (2013).
Fukuda, et al., "The Chemokine GROβ Mobilizes Early Hematopoietic Stem Cells Characterized by Enhanced Homing and Engraftment," *Blood*, 110(3):860-869, (2007).
Goessling, et al., "Genetic Interaction of PGE2 and Wnt Signaling Regulates Developmental Specification of Stem Cells and Regeneration," *Cell*, 136:1136-1147, (2009).
Goldmacher, et al., "Anti-CD38-Blocked Ricin: An Immunotoxin for the Treatment of Multiple Myeloma," *Blood*, 84(9):3017-3025, (Nov. 1, 1994).
Hoggatt, et al., "Many Mechanisms Mediating Mobilization: An Alliterative Review," *Current Opinion in Hematology*, 18:231-238, (2011).
Hoggatt, et al., "Prostaglandin $E_2$ enhances Hematopoietic Stem Cell Homing, Survival, and Proliferation," *Blood*, 113(22):5444-5455, (2009).
Illies, et al., "Requirement of Inositol Pyrophosphates for Full Exocytotic Capacity in pancreatic β Cells," *Science*, 318: p. 1299, (2007).
Ishikawa, et al., "An Assay for Long-Term Engrafting Human Hematopoietic Cells Based on Newborn NOD/SCID/β2-Microglobulinnull Mice," *Experimental Hematology*, 30:488-494, (2002).
Janowiak, et al., "An Approach to Characterizing Single-Subunit Mutations in Multimeric Prepores and Pores of Anthrax Protective Antigen," *Protein Science*, 18:348-358, (2009).
Kraft, et al. "Effect and Kinetics of Depleting ACK-2 Anti C-Kit Monoclonal Antibody on Hematopoeisis and Hematopoetic Progenitors and Ability to Condition for Bone Marrow Transplantation," *Blood*, 104:4963, (2004) (Abstract—2 pages).

Merlini, et al., "Studies on C-Kit Protein Expression and C-Kit Gene Mutation in Multiple Myeloma," *Haematologica*, 94(suppl. 4): p. 87, P084 (Oct. 18-21, 2009).
Mourez, et al., "Mapping Dominant-Negative Mutations of Anthrax Protective Antigen by Scanning Mutagenesis," *PNAS*, 100(24):13803-13808, (2003).
North, et al., "Prostaglandin E2 Regulates Vertebrate Hematopoietic Stem Cell Homeostasis," *Nature*, 447(7147):1007-1011, (2007).
Pagel, et al., "Pretargeted Radioimmunotherapy Using Anti-CD45 Monoclonal Antibodies to Delivery Radiation to Murine Hematolymphoid Tissues and Human myeloid Leukemia," *Cancer Res.*, 69(1):185-192, (2009).
Palchaudhuri, et al., "32 Immunotoxin Enables Non-Genotoxic Conditioning for Hematopoietic Stem Cell Transplantation," 57th Annual Meeting & Exposition, Orlando, FL Dec. 5-8, 2015, 2 page.
Palchaudhuri, et al., "Non-Genotoxic Conditioning for Hematopoietic Stem Cell Transplantation Using a Hematopoietic-Cell-Specific Internalizing Immunotoxin," *Nature Biotech.*, Jun. 6, 2016, Abstract only, pp. 1-4. Retrieved from the Internet: <http://www.nature.com.nbt/journal/baop/ncurrent/full/nbt.3584.htms> on Jun. 8, 2016.
PCT Application No. PCT/US16/26040, entitled "Compositions and Related Methods for Non-Myeloablative Conditioning," filed on Apr. 5, 2016.
Polito, et al., "Immunotoxins and Other Conjugates Containing Saporin-S6 for Cancer Therapy," *Toxins*, 3:697-720, (2011).
Press, et al., "Retention of B-Cell-Specific Monoclonal Antibodies by Human Lymphoma Cells," *Blood*, 83(5):1390-1397, (1994).
Rogers, et al., "Mutant Anthrax Toxin B Moiety (Protective Antigen) Inhibits Angiogenesis and Tumor Growth," *Cancer Res.*, 67(20):9980-9985, (2007).
Rothenberg, et al., "Identification of a cKit+ Colonic Crypt Base Secretory Cell That Supports Lgr5+ Stem Cells in Mice," *Gastroenterology*, 142(5):1195-1205 (2012).
Sakamaki, "The Role of Gemtuzumab Ozogamicin in the Treatment of Acute Myeloid Leukemia Patients," *Gan to Kagaky Ryoho*, 35(9):1629-1634, (Sep. 2008).
Waldron, et al., "An Old Idea Tacking a New Problem: Targeted Toxins Specific for Cancer Stem Cells," *Antibodies*, 2:82-92, (2013).
Xue, et al., "Antibody Targeting KIT as Pretransplantation Conditioning in Immunocompetent Mice," *Blood*, 116(24):5419-5422, (2010).
Xue, "Antibody Targeting KIT as Pretransplantation Conditioning in Immunocompetent Mice," *Blood*, 116:5419-5422, (2010).
Yan, et al., "Characterization of Dominant-Negative Forms of Anthrax Protective Antigen," *Molecular Medicine*, pp. 46-51, (2003).
Examination Report No. 1 from AU Application No. 2017204125, dated Aug. 24, 2017.
Response to Examination Report No. 1 from AU Application No. 2017204125, dated Aug. 6, 2017.
International Search Report and Written Opinion from PCT/US2016/026276, dated Jul. 12, 2016.
Office Action from U.S. Appl. No. 15/148,837, dated Jan. 4, 2017.
Final Office Action from U.S. Appl. No. 15/148,837, dated May 22, 2017.
Notice of Allowance from U.S. Appl. No. 15/148,837, dated Dec. 13, 2018.
Non-Final Office Action from U.S. Appl. No. 16/205,205, dated Jul. 9, 2019.
Final Office Action from U.S. Appl. No. 16/205,205, dated Nov. 25, 2019.
Hoshino, et al., "Circadian Rhythm of Immune Function: Actual Condition and Importance of Biological (Immune) Clock," *Biotherapy*, 10(11):1371-1383, (1996).
Kuroda, et al., "Saporin Toxin-Conjugated Monoclonal Antibody Targeting Prostate-Specific Membrane Antigen Has Potent Anticancer Activity," *The Prostate*, 70:1286-1294, (2010).
Akbari, et al., "In Vitro Selective Depletion of CD4(+)CD25(+) Regulatory T-Cells From Pbmc Using Anti-Tac-SAP," *J. Immunotoxicol*, 9/4:368-373, Abstract only, 2012.
Chhabra, et al., "Successful Engraftment of Hematopoietic Stem Cells into Immunocompetent Recipients Using Only Anti-CD117 Antibody and CD47 Blockade as Conditioning," *Blood*, 124/21, p. 2410, (2014).

(56) References Cited

OTHER PUBLICATIONS

Li, et al., "3A4, A New Potential Target for B and Myeloid Lineage Leukemias," *J. Drug Target*, 19/9:797-804, Abstract only, 2011.
Morris, et al., "Antibody-Based Therapy of Leukaemia," *Expert Rev. Mol. Med., 11* p. e29, doi: 10.1017/S1462399409001215, 2009.

Immunotoxins as Conditioning Strategy

Internalizing protein immunotoxins have not been explored as conditioning agents.

Saporin-ribosome inactivating protein, able to kill cells regardless of cell cycle status.

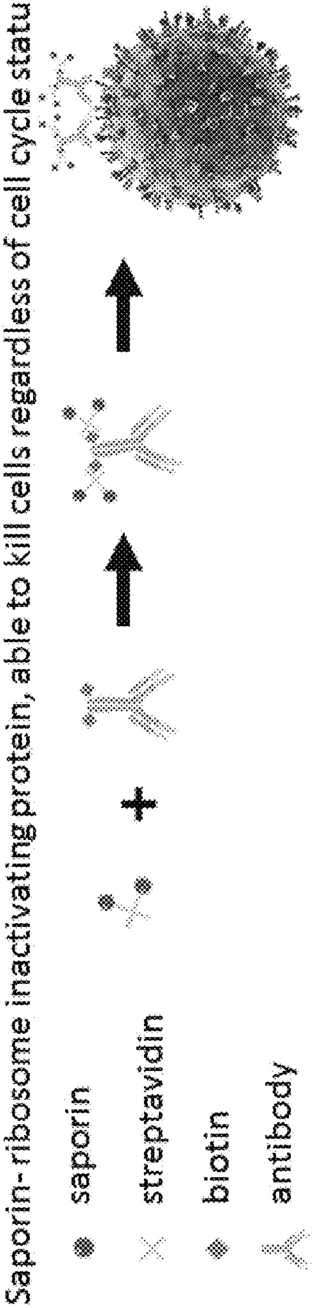

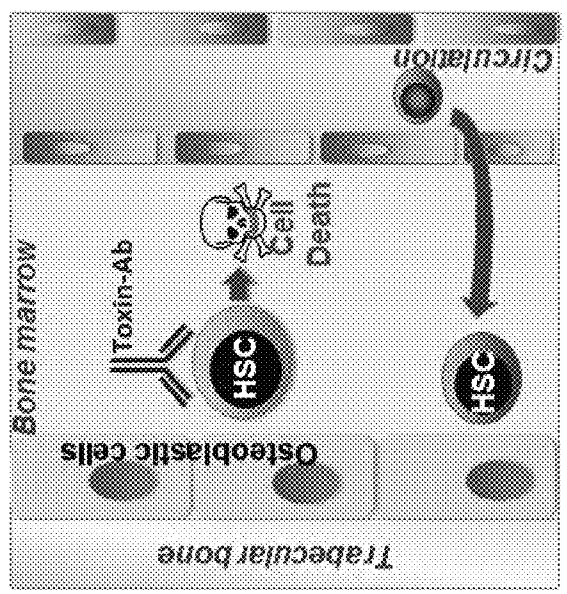

| Target | Engraftment |
|---|---|
| CD45 | ✓ |
| CD117 (2B8) | ✓ |
| CXCR4 | ✗ |
| VLA-4 (CD49d) | ✗ |
| VLA-6 (CD49f) | ✗ |
| CD51 | ✗ |

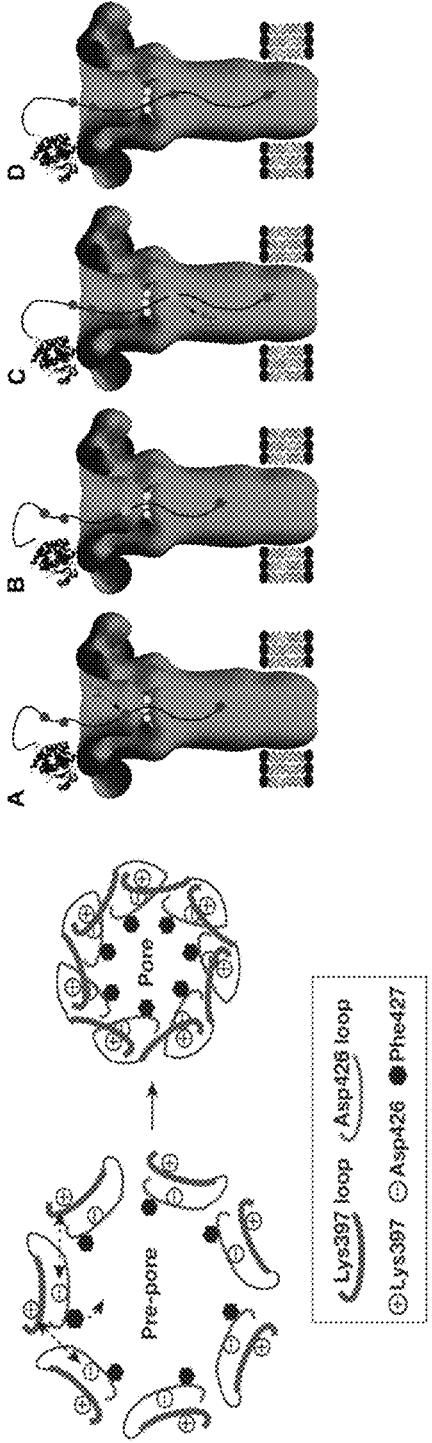

Mechanism of Translocation

- LF, EF, and LFN bind to PA63 with high affinity (*K*d ~ 1–2 nM; *k*on ~ $3\times10^{5}$ $M^{-1}$ $s^{-1}$; *k*off ~ $(3–5)\times10^{-4}$ $s^{-1}$),
- Mechanism of transport largely studied in planar bilayer membranes. ATP is not required but ΔpH is required.
- Charge-state Brownian-ratchet mechanism of translocation
- N-terminus of LFN is helical and extreme N-terminus is basic and destabilized in acidic pH, facilitating threading of protein into the pore in N-C direction
- Pore is cation selective and acidic residues must be protonated prior to translocation. Transport is unidirectional as acidic residues become deprotonated in cytosol (higher pH) and cannot back diffuse.
- Disulfide cross links introduced or addition of small molecule ligands to LFN-DTA or LFN-DHFR prevent translocation. Molecular Aspects of Medicine 30 (2009) 413–422

*FIG. 35*

Activity of LFN-DTA against human HSCs *in vitro*

Human mobilized peripheral blood CD34+ HSCs treated in vitro with various concentrations of LFN-DTA immunotoxin in the presence of 10nM WT-PA for 96 hours. Cell viability assessed using MTS assay (Promega). 100% cell death observed at 1 femtomolar concentration of LFN-DTA, demonstrating LFN-DTA can be used to enable potent killing of human HSCs.

*FIG. 36*

COMPOSITIONS AND METHODS FOR NON-MYELOABLATIVE CONDITIONING

RELATED APPLICATIONS

This application is a continuation of U.S. application Ser. No. 16/205,205, filed Nov. 29, 2018 (now U.S. Pat. No. 10,570,207, issued Feb. 25, 2020), which is a continuation of U.S. application Ser. No. 15/148,837, filed May 6, 2016 (now U.S. Pat. No. 10,280,225, issued May 7, 2019), which is a continuation of PCT Application No. PCT/US2016/026276, filed Apr. 6, 2016, which claims the benefit of U.S. Provisional Application No. 62/143,642, filed Apr. 6, 2015, U.S. Provisional Application No. 62/220,204, filed Sep. 17, 2015, U.S. Provisional Application No. 62/221,595, filed Sep. 21, 2015 and U.S. Provisional Application No. 62/239,573, filed Oct. 9, 2015, the entire teachings of these applications are incorporated herein by reference.

GOVERNMENT FUNDING

This invention was made with government support under HL097794, awarded by the National Institutes of Health. The government has certain rights in the invention.

BACKGROUND OF THE INVENTION

Hematopoietic stem cell transplant (HSCT) is primarily indicated to treat malignancies and requires a conditioning of the subject's tissues (e.g., bone marrow tissue) prior to engraftment. HSCT indications and hemoglobinopathies include, for example, sickle cell anemia, beta thalassemias, Fanconi anemia, Wiskott-Aldrich syndrome, adenosine deaminase SCID (ADA SCID), metachromatic leukodystrophy and HIV/AIDS; the list of indications will continue to expand with improvement in gene editing technologies. In certain instances, 20% engraftment of transplanted cells may alleviate or cure the disease.

Current non-targeted conditioning methods, which include, for example, irradiation (e.g., total body irradiation or TBI) and DNA alkylating/modifying agents, are highly toxic to multiple organ systems, hematopoietic and non-hematopoietic cells and the hematopoietic microenvironment. These harsh conditioning regimens effectively kill the host subject's immune and niche cells and adversely affect multiple organ systems, frequently leading to life-threatening complications.

To fully realize the curative potential of HSCT, the development of mild-conditioning regimens that avoid undesirable toxicity is essential. Needed are novel, preferably non-myeloablative, compositions and methods that may be used to condition a subject's tissues (e.g., bone marrow tissues), while lessening undesirable toxicity and minimizing the incidence of serious adverse reactions. Also needed are novel therapies that can selectively ablate an endogenous hematopoietic stem cell population in a target tissue, while minimizing or eliminating the effects of such therapies on non-targeted cells and tissues, such as platelets, white blood cells and red blood cells. Also needed are assays and methods for identifying agents that can selectively deplete or ablate an endogenous hematopoietic stem cell population.

SUMMARY OF THE INVENTION

Disclosed herein are methods and compositions that are useful for ablating selected cell populations and conditioning a subject's tissues for engraftment or transplant, as well as assays and methods of identifying candidate agents that are useful for conditioning a subject's tissues for engraftment or transplant. In certain embodiments, the methods and compositions disclosed herein are non-myeloablative. Also disclosed are methods of delivering a toxin to a cell, e.g., by targeting one or more markers (e.g., the cell surface CD45 or CD117 markers), such that the toxin is internalized; such methods are useful for effectively conditioning a subject for engraftment or transplant (e.g., conditioning a human subject for hematopoietic stem cell transplant).

Advantageously, the methods, assays and compositions disclosed herein do not cause the toxicities that have generally been associated with traditional conditioning methods, such as irradiation. For example, relative to traditional conditioning regimens, in certain embodiments the compositions and methods disclosed herein do not induce neutropenia, thrombocytopenia and/or anemia, yet result in a stable, mixed chimerism that is of therapeutic relevance. Such compositions and methods may be used, for example, to correct, cure or otherwise ameliorate one or more diseases in an affected subject (e.g., the methods and compositions disclosed herein may be used to correct or cure HIV, AIDS, or hemoglobinopathies, such as sickle cell anemia and Fanconi anemia).

In certain embodiments, disclosed herein are methods of conditioning a subject or a subject's target tissues for engraftment, such methods comprising a selective depletion or ablation of an endogenous stem cell (e.g., hematopoietic stem cell) or progenitor cell population in a target tissue of the subject by administering to the subject an effective amount of an agent coupled (e.g., functionally coupled) to a toxin, wherein the toxin is internalized by the endogenous stem cell population, thereby depleting or ablating the endogenous stem cell population in the target tissue and conditioning the subject for engraftment of a transplanted cell or cell population. In certain embodiments the agent is selected from the group consisting of an antibody and a ligand.

Also disclosed herein are methods of engrafting stem cells in a subject, such methods comprising: (a) administering to the subject an effective amount of an agent coupled to a toxin, wherein the toxin is internalized by an endogenous stem cell (e.g., hematopoietic stem cell) or progenitor cell population, thereby selectively depleting or ablating the endogenous stem cell population in a target tissue of the subject; and (b) administering a stem cell population to the target tissue of the subject, wherein the administered stem cell population engrafts in the target tissue of the subject.

In certain aspects, also disclosed herein are methods of treating a stem cell disorder in a subject, such methods comprising: (a) administering to the subject an effective amount of an agent coupled (e.g., functionally coupled) to a toxin, wherein the toxin is internalized by an endogenous stem cell (e.g., hematopoietic stem cell) or progenitor cell population in a target tissue of the subject, thereby depleting or ablating the endogenous stem cell or progenitor cell population in the target tissue of the subject; and (b) administering a stem cell population to the target tissue of the subject, wherein the administered stem cell population engrafts in the target tissue of the subject. In some embodiments, the stem cell population is administered to the target tissues of the subject after the immunotoxin has cleared or dissipated from the subject's target tissues.

In certain embodiments, the inventions disclosed herein are directed to methods of selectively depleting or ablating an endogenous hematopoietic stem cell (HSC) or progenitor cell population in a target tissue of a subject, the methods comprising administering to the subject an effective amount (e.g., 1.5 mg/kg, 3 mg/kg) of an agent coupled to a toxin; wherein the agent selectively binds to CD45 and the toxin is internalized by the endogenous HSC or progenitor cell population, thereby depleting or ablating the endogenous HSC or progenitor cell population in the target tissue.

In some embodiments, the inventions disclosed herein are directed to methods of selectively depleting or ablating an endogenous hematopoietic stem cell or progenitor cell population in a target tissue of a subject, the methods comprising administering to the subject an effective amount of an agent coupled (e.g., functionally coupled) to a toxin; wherein the agent selectively binds to CD117 and the toxin is internalized by the endogenous HSC or progenitor cell population, thereby depleting or ablating the endogenous HSC or progenitor cell population in the target tissue.

Also disclosed herein are methods of selectively ablating an endogenous stem cell (e.g., hematopoietic stem cells) or progenitor cell population in a target tissue of a subject, the methods comprising: administering to the subject an effective amount of an internalizing antibody which specifically or selectively binds to CD45 and is coupled to a toxin and thereby ablating the endogenous stem cell population in the target tissue.

In certain embodiments, disclosed herein are methods of stem cell transplant (e.g., hematopoietic stem cell transplant), such methods comprising: administering to a subject an effective amount of an internalizing antibody which specifically or selectively binds to CD117 and is coupled to a toxin and thereby ablating an endogenous stem cell population in a target tissue; and administering an exogenous stem cell population in the target tissue of the subject.

In certain aspects, also disclosed are methods of treating or curing a hemoglobinopathy (e.g., sickle cell anemia) in a subject, the methods comprising: administering to the subject an effective amount of an internalizing antibody that specifically or selectively binds to CD45 or CD117 and is coupled to a toxin and thereby ablating an endogenous stem cell (e.g., hematopoietic stem cell) or progenitor cell population in a target tissue of the subject; followed by a step of administering an exogenous stem cell population to the target tissue of the subject. In some embodiments, the exogenous stem cell population is administered to the target tissues of the subject after the immunotoxin (e.g., an anti-CD45-SAP or an anti-CD117-SAP immunotoxin) has cleared or dissipated from the subject's target tissues.

In certain aspects, the agents disclosed herein selectively target a population of cells of the target tissues. For example, in certain embodiments, such an agent (e.g., an antibody or ligand) may be internalized by a targeted hematopoietic stem cell upon binding of such agent to a cell surface protein expressed by the hematopoietic stem cell. Cell surface proteins expressed by the cells of the target tissue (e.g., hematopoietic stem cells residing in the bone marrow stem cell niche) thus provide a means of targeting, in some instances discriminately, the immunotoxins disclosed herein to a population of cells expressing that protein. In some instances, the expression of the protein is restricted to a specific cell population, and the protein can be used as a target to deliver the immunotoxin selectively to that cell population while not affecting or minimally affecting the cell populations which don't express the protein (e.g., non-target tissues or off-target tissues of the subject). Alternatively, the expression of the cell surface protein to be targeted by the immunotoxin is not restricted to a specific cell population; in these instances it is possible to use a different moiety to restrict delivery of the immunotoxin to only a subset of the cell population expressing the cell surface protein target. For example, in the context of a bispecific antibody, one specificity can be for the target cell surface protein and the other specificity can be for a marker having expression restricted to the cell population of choice.

In certain embodiments, the cells of a subject's target tissues comprise an endogenous stem cell population, such as for example, endogenous hematopoietic stem cells and/or progenitor cells residing in the target tissue. In certain aspects, the hematopoietic stem cells or progenitor cells express one or more markers that may be used to selectively target the agents comprising the immunotoxin compositions disclosed herein to the cells of the subject's target tissues.

Any markers that are capable of being used to discriminate the target cell population from the population of non-targeted cells, including any of the markers described herein, can be targeted by the agents that comprise the immunotoxins described herein for delivery of toxin to the cell population. For example, in certain aspects of the present inventions, an agent that comprises the immunotoxin composition may selectively bind to one or more cell surface markers expressed by the cells of the target tissues (e.g., a CD45-SAP immunotoxin may selectively bind to hematopoietic stem cells having cell surface expression of the CD45 marker). In certain embodiments, the targeted hematopoietic stem cells or progenitor cells express one or more markers that may be targeted and to which the immunotoxin selectively or preferentially binds, such markers selected from the group of markers consisting of HLA-DR, CD11a, CD18, CD34, CD41/61, CD43, CD45, CD49d (VLA-4), CD49f (VLA-6), CD51, CD58, CD71, CD84, CD90, CD97, CD117 (c-kit), CD133, CD134, CD162, CD166, CD184 (CXCR4), CD205 and CD361. In certain embodiments, the targeted cells (e.g., the hematopoietic stem cells or progenitor cells) in the target tissue express one or more markers that may be targeted and to which the immunotoxin selectively or preferentially binds, such markers selected from the group of markers consisting of: CD13, CD33, CD34, CD44, CD45, CD49d: VLA-4, CD49f: VLA-6, CD59, CD84: CD150 family, CD90: Thy1, CD93, CD105: Endoglin, CD117: cKit/SCF receptor, CD123: IL-3R, CD126: IL-6R, CD133, CD135: Flt3 receptor, CD166: ALCAM, CD184: CXCR4, Prominin 2, Erythropoietin R, Endothelial Cell-Selective Adhesion Molecule, CD244, Tie1, Tie2, MPL, G-CSFR or CSF3R, IL-1R, gp130, Leukemia inhibitory factor Receptor, oncostatin M receptor, Embigin and IL-18R. In still other embodiments, the targeted cells (e.g., hematopoietic stem cells or progenitor cells) in the target tissue express one or more markers that may be targeted and to which the agents that comprise the immunotoxin selectively bind, such markers selected from the group of markers consisting of: CD150, CD27 and CD201. For example, in some embodiments, the hematopoietic stem cells or progenitor cells express CD45. Similarly, in some embodiments, the hematopoietic stem cells or progenitor cells express CD117. Similarly, in some embodiments, the hematopoietic stem cells or progenitor cells express CD34.

In certain embodiments, the marker is selected from the group consisting of HLA-DR, CD11a, CD18, CD34, CD41/61, CD43, CD45, CD47, CD58, CD71, CD84, CD97, CD117 (c-kit), CD133, CD162, CD166, CD205 and CD361. In certain embodiments, the targeted cells comprise human hematopoietic stem cells expressing one or more markers that may be targeted and to which the agents that comprise the immunotoxin bind, such markers selected from the group consisting of CD7, CDw12, CD13, CD15, CD19, CD21, CD22, CD29, CD30, CD33, CD34, CD36, CD38, CD40, CD41, CD42a, CD42b, CD42c, CD42d, CD43, CD45, CD45RA, CD45RB, CD45RC, CD45RO, CD48, CD49b, CD49d, CD49e, CD49f, CD50, CD53, CD55, CD64a, CD68, CD71, CD72, CD73, CD81, CD82, CD85A, CD85K, CD90, CD99, CD104, CD105, CD109, CD110, CD111, CD112, CD114, CD115, CD117, CD123, CD124, CD126, CD127, CD130, CD131, CD133, CD135, CD138, CD151, CD157, CD162, CD164, CD168, CD172a, CD173, CD174, CD175, CD175s, CD176, CD183, CD191, CD200, CD201, CD205, CD217, CD220, CD221, CD222, CD223, CD224, CD225, CD226, CD227, CD228, CD229, CD230, CD235a, CD235b, CD236, CD236R, CD238, CD240, CD242, CD243, CD277, CD292, CDw293, CD295, CD298, CD309, CD318, CD324, CD325, CD338, CD344, CD349 and CD350.

In certain embodiments, the targeted cells comprise human hematopoietic stem cells expressing one or more markers that may be targeted and to which the agents that comprise the immunotoxin bind, such markers selected from the group consisting of CD11a, CD18, CD37, CD47, CD52, CD58, CD62L, CD69, CD74, CD97, CD103, CD132, CD156a, CD179a, CD179b, CD184, CD232, CD244, CD252, CD302, CD305, CD317 and CD361.

In certain embodiments, the endogenous cells (e.g., HSCs or progenitor cells) express one or more markers, and the administered agent (e.g., an antibody-toxin conjugate) selectively binds to the one or more markers or a fragment or epitope thereof. In certain aspects the methods disclosed herein specifically or discriminatorily target or are directed towards the subject's target tissues, while not affecting or minimally affecting the non-target tissues or off-target tissues (e.g., the thymus) of the subject. In certain embodiments, the methods and compositions disclosed herein do not deplete or ablate endogenous neutrophils or myeloid cells. In certain embodiments, the methods and compositions disclosed herein cause an increase in mature endogenous neutrophils. In certain aspects, the methods and compositions disclosed herein do not deplete or ablate endogenous platelets. In still other embodiments, the methods and compositions disclosed herein do not induce anemia in the subject.

In certain embodiments, the markers are internalizing. For example, upon binding of the agent to an internalizing marker (e.g., a cell surface receptor), the composition is internalized by the cell expressing such marker.

In some embodiments, the marker is not internalizing. For example, in such embodiments, a first marker may be used as a means of discriminately targeting a cell population, while a second marker may be targeted to effectuate the internalization of the immunotoxin composition intracellularly.

The immunotoxin compositions disclosed herein comprise an agent to facilitate the selective delivery of such compositions to a population of cells in the target tissues (e.g., hematopoietic stem cells of the bone marrow stem cell niche). In some embodiments, the agents disclosed herein comprise an antibody (e.g., a monoclonal antibody). In some embodiments the antibody is a blocking antibody or an antagonist antibody. In some embodiments the antibody is not a blocking antibody or an antagonist antibody. In certain embodiments, the agents disclosed comprise a ligand. In certain aspects, the agent selectively binds to CD45. In certain aspects, the agent is a CD45 antagonist. Alternatively, in certain embodiments the agent is not a CD45 antagonist. In some embodiments, the toxin is internalized by a cell expressing CD45 following binding of the agent to an epitope of the CD45 cell surface marker.

In some embodiments, the agents disclosed herein selectively bind to CD117. In certain aspects, the agent is a CD117 antagonist. Alternatively, in certain aspects the agent is not a CD117 antagonist. In some embodiments, the toxin is internalized by a cell expressing CD117 following binding of the agent to an epitope of the CD117 cell surface marker.

In certain aspects, the agent is antibody clone 104. In certain embodiments, the agent is antibody clone 30F11. In certain embodiments, the agent is antibody clone ACK2. In certain aspects, the agent is an antibody which is not clone ACK2. In certain aspects, the agent is antibody clone ACK2 and the toxin is not directly coupled to the antibody. In still other aspects, the agent is antibody clone 2B8. In some embodiments, the agent is an antibody which is not clone 2B8. In some embodiments, the agent is an antibody which is not clone 2B8 and the toxin is not directly coupled to the antibody. In certain aspects, the agent is antibody clone 3C11. In certain embodiments, the agent is antibody clone MEM-28. In certain embodiments, the agent is antibody clone HI130. In certain embodiments, the agent is antibody clone 581. In certain embodiments, the agent is antibody clone 4H11. In certain aspects, the agent is an antibody selected from the group consisting of clone L243, clone TS2/4, clone TS1/18, clone 581, clone 4H11, clone A2A9/6, clone CD43-10G7, clone BHPT-1, clone orb12060, clone 2D1, clone CC2C6, clone TS2/9, clone CY1G4, clone OKT9, clone CD84.1.21, clone VIM3b, clone A3C6E2, clone EMK08, clone TMP4, clone KPL-1, clone 3a6, clone HD83 and clone MEM-216. In certain embodiments, the agent is an antibody comprising a complementarity determining region that is the same as the complementarity determining region for one or more antibodies selected from the group consisting of L243, clone TS2/4, clone TS1/18, clone 581, clone 4H11, clone A2A9/6, clone CD43-10G7, clone BHPT-1, clone orb12060, clone 2D1, clone CC2C6, clone TS2/9, clone CY1G4, clone OKT9, clone CD84.1.21, clone VIM3b, clone A3C6E2, clone EMK08, clone TMP4, clone KPL-1, clone 3a6, clone HD83 and clone MEM-216. In certain embodiments, the agent is an antibody that binds to the same epitope as one or more antibodies selected from the group consisting of L243, clone TS2/4, clone TS1/18, clone 581, clone 4H11, clone A2A9/6, clone CD43-10G7, clone BHPT-1, clone orb12060, clone 2D1, clone CC2C6, clone TS2/9, clone CY1G4, clone OKT9, clone CD84.1.21, clone VIM3b, clone A3C6E2, clone EMK08, clone TMP4, clone KPL-1, clone 3a6, clone HD83 and clone MEM-216. In certain aspects, the agent comprises an antibody that selectively recognizes and/or binds to the CD34 marker (e.g., clone 581 or clone 4H11). In certain aspects, the agent comprises an antibody that selectively recognizes and/or binds to the CD45 marker (e.g., clone MEM-28 or clone HI130). In certain aspects, the agent is a humanized antibody.

In certain embodiments, the agent is a ligand. For example, in certain embodiments the ligand may be selected from the group of ligands consisting of Stem cell factor (SCF) or cKit ligand, CXCL12: Stromal derived factor 1 (SDF1), Angiopoietin 1 to 4 (Ang1, Ang2, Ang3, Ang4), TPO (thrombopoietin), Erythropoietin, FLT3L, VLA4, VLA6, IL-1, IL-3, IL-6, IL-18, G-CSF, Oncostatin M and LIF.

In certain embodiments, the agent is coupled to a toxin (e.g., saporin). In certain aspects, the agents (e.g., antibodies) disclosed herein are characterized as being internalizing. In certain aspects, such agents are internalized by a cell expressing a marker or moiety (e.g., a cell surface marker or antigen) to which the agent binds (including, but not limited to, CD45 and/or CD117) following binding of such agent (e.g., antibody or ligand).

In some embodiments, the toxin is internalized by receptor-mediated internalization. In certain aspects, the toxins disclosed herein are internalized by the endogenous stem cell population at a rate of at least about 10% (e.g., over about 24 hours). In certain aspects, the toxins disclosed herein are internalized by the endogenous stem cell population at a rate of at least about 50% (e.g., over about 24 hours). In yet other embodiments, the toxins disclosed herein are internalized by the endogenous stem cell population at a rate of at least about 90% (e.g., over about 24 hours).

The methods disclosed herein may be practiced using any suitable toxin. In certain aspects, the toxin is selected from the group of toxins consisting of saporin, diphtheria toxin, pseudomonas exotoxin A, Ricin A chain derivatives, small molecule toxins and combinations thereof. In certain aspects, the toxin is a saporin. In certain embodiments, the toxin inactivates ribosomes. In certain embodiments, the toxin inhibits protein synthesis. In certain aspects, the toxin is not a radioimmunotoxin. In certain embodiments, the toxin exerts its effects upon gaining entry into an intracellular compartment of one or more cells in the target tissue. In some embodiments, the methods and compositions disclosed herein do not induce cell death through DNA-damage. In some embodiments the toxin induces cell death regardless of the cell cycle stage of the cell.

In certain aspects, the toxin is selected from the group of toxins consisting of abrin toxin, modeccin toxin, gelonin toxin, momordin toxin, trichosanthin toxin, luffin toxin and combinations thereof.

In various embodiments of any aspect of the present inventions, the toxins useful in accordance with the immunotoxin compositions and methods of the present invention comprise one or more DNA-damaging molecules. For example, the selected toxin may comprise one or more anti-tubulin agents (e.g. maytansines) or tubulin inhibitors, DNA crosslinking agents, DNA alkylating agents and cell cycle or mitotic disrupters.

In certain embodiments of any aspect of the present inventions, the toxin inhibits RNA polymerase II and/or III (e.g., mammalian RNA polymerase II). In certain aspects such an RNA polymerase II and/or III inhibitor toxin is or comprises one or more amatoxins or a functional fragment, derivative or analog thereof. For example, contemplated toxins for use in accordance with any of the methods or compositions disclosed herein may include or comprise one or more amatoxins selected from the group consisting of α-amanitin, β-amanitin, γ-amanitin, £-amanitin, amanin, amaninamide, amanullin, amanullinic acid and any functional fragments, derivatives or analogs thereof.

Contemplated herein is the coupling or conjugation of an agent (e.g., an antibody) to a toxin (e.g., saporin) to facilitate the targeted delivery of such agents to cells of a target tissue. In certain aspects, the agent is directly coupled to the toxin, for example as a chimeric fusion protein. Alternatively, in certain aspects, the agent is indirectly coupled to the toxin (e.g., using a streptavidin chimera). In certain embodiments the coupling of the agent and toxin is facilitated by a streptavidin-biotin interaction (an example of an indirect linkage). In certain embodiments, the agent is biotinylated. In certain aspects, the toxin is biotinylated. In certain embodiments, the agent is coupled to a streptavidin-toxin chimera. In certain aspects, the toxin is coupled to a streptavidin-toxin chimera.

In certain aspects, the ratio of agent (e.g., antibody) to streptavidin-toxin is about 1:1, about 1:4, about 2:1 or about 4:1.

In certain aspects, the ratio of agent (e.g., antibody) to toxin is about 1:2, about 1:2.5, about 1:2.8, about 1:3, about 1:3.5, about 1:4, about 1:4.5, about 1:5, 1:6 or about 1:8.

In certain aspects, the methods disclosed herein further comprise a step of administering a stem cell population to the target tissues of the subject, wherein the administered stem cell population engrafts in the target tissues of the subject. In certain embodiments, the step of administering or transplanting a stem cell population is performed after the endogenous stem cells (e.g., hematopoietic stem cells) or progenitor cells are depleted or ablated from the target tissues either partially or fully. In a preferred embodiment, such administering step is performed after the subject's target tissue (e.g., bone marrow tissue) has been conditioned in accordance with the methods and compositions disclosed herein. In some embodiments, the stem cell population is administered to the target tissues of the subject after the immunotoxin (e.g., an anti-CD45-SAP or an anti-CD117-SAP immunotoxin) has cleared or dissipated from the subject's target tissues such that the level of immunotoxin remaining in the target tissue of the subject does not induce significant cell death in the transplanted cell population. For example, in some embodiments, the stem cell population is administered to the target tissue of the subject about two to about eighteen days after the administration of the immunotoxin. In some embodiments, the stem cell population is administered to the target tissue of the subject at least one, two, three, four, five, six, seven, eight, nine, ten, twelve, twelve, thirteen, fourteen, fifteen, eighteen, twenty one, thirty six, forty two, fifty six, sixty three, seventy, eighty, ninety, one hundred, one hundred and twenty days or more, after the immunotoxin has cleared or dissipated from the target tissues of the subject.

In some embodiments, such methods disclosed herein increase the efficiency of the engraftment of the administered stem cell population in the target tissue, as compared to a method performed using only the step of administering the stem cell population to the target tissue of the subject. For example, in certain embodiments, the efficiency of engraftment is increased by at least about 5-100%, e.g., 5, 10, 15, 20, 25, 50, 75, 100% or more.

The methods and compositions disclosed herein may be used to condition a subject's tissues (e.g., bone marrow) for engraftment or transplant and following such conditioning, a stem cell population is administered to the subject's target tissues. In certain aspects, the stem cell population comprises an exogenous stem cell population. In some embodiments, the stem cell population comprises the subject's endogenous stem cells (e.g., endogenous stem cells that have been genetically modified to correct a disease or genetic defect).

In certain embodiments, the methods and compositions disclosed herein cause an increase in granulocyte colony stimulating factor (GCSF). In certain aspects, the methods and compositions disclosed herein cause an increase in macrophage colony stimulating factor (MCSF). In certain embodiments, the methods and compositions disclosed herein cause an increase in endogenous myeloid cells. Without wishing to be bound by any particular theory or mechanism of action, the increase in endogenous myeloid cells that is observed following administration of the agents, toxins and related conjugates disclosed herein may occur as a result of an increase in the subject's endogenous GCSF and/or MCSF. Accordingly, in certain embodiments, such an increase in endogenous myeloid cells occurs as a result of an increase in granulocyte colony stimulating factor (GCSF) and/or macrophage colony stimulating factor (MCSF) that may occur secondary to the methods and compositions disclosed herein. In certain aspects, the methods and compositions disclosed herein do not deplete or ablate endogenous lymphoid cells.

In certain aspects, following conditioning of a subject's target tissues in accordance with the methods and compositions disclosed herein the subject's innate immunity is preserved. In certain aspects, following conditioning of a subject's tissues in accordance with the methods and compositions disclosed herein the subject's adaptive immunity is preserved. In certain embodiments, the methods and compositions disclosed herein preserve thymic integrity of the subject. Similarly, in some embodiments, the methods and compositions disclosed herein preserve vascular integrity of the subject.

In some embodiments, conditioning of a subject's target tissues in accordance with the methods and compositions disclosed herein achieves at least about 5-90% engraftment of the exogenous stem cell population. For example, conditioning of a subject's tissues in accordance with the methods and compositions disclosed herein achieves at least about 5%, 10%, 12.5%, 15%, 17.5%, 20%, 25%, 30%, 35%, 40%, 45%, 50%, 55%, 60%, 65%, 70%, 75%, 80%, 85%, 90%, 95%, 97.5%, 99% or more engraftment of the exogenous stem cell population.

In certain embodiments, conditioning of a subject's tissues in accordance with the methods and compositions disclosed herein achieves at least about 5-90% donor chimerism (e.g., 20% donor chimerism) in the subject's target tissue (e.g., bone marrow) four months post-administration of the exogenous stem cell population to the subject. For example, in certain embodiments, conditioning of a subject's tissues in accordance with the methods and compositions disclosed herein achieves at least about 5%, 10%, 12.5%, 15%, 17.5%, 20%, 25%, 30%, 35%, 40%, 45%, 50%, 55%, 60%, 65%, 70%, 75%, 80%, 85%, 90%, 95%, 97.5%, 99% or more donor chimerism in the target tissues of the subject four months post-administration of the exogenous stem cell population to the subject.

The methods and compositions disclosed herein may be used to condition bone marrow tissue. In certain aspects, the agents (e.g., an anti-CD45-toxin conjugate) disclosed herein are useful for non-myeloablative conditioning, for example, bone marrow conditioning in advance of hematopoietic stem cell transplantation.

The methods and compositions disclosed herein may be used to treat, cure or correct a number of diseases, including, for example, a disease selected from the group consisting of sickle cell anemia, thalassemias, Fanconi anemia, Wiskott-Aldrich syndrome, adenosine deaminase SCID (ADA SCID), HIV/AIDS, metachromatic leukodystrophy, Diamond-Blackfan anemia and Schwachman-Diamond syndrome. Preferably, such methods and compositions are useful for treating such diseases without causing the toxicities that are observed in response to traditional conditioning therapies, such as irradiation.

In certain aspects, the subject has a non-malignant hemoglobinopathy (e.g., a hemoglobinopathy selected from the group consisting of sickle cell anemia, thalassemia, Fanconi anemia, and Wiskott-Aldrich syndrome). In certain aspects, the subject has an immunodeficiency. For example, in certain embodiments, the subject has a congenital immunodeficiency. Alternatively, in other aspects, the subject has an acquired immunodeficiency (e.g., an acquired immunodeficiency selected from the group consisting of HIV and AIDS). In yet other embodiments, the subject has a stem cell disorder selected from the group of disorders consisting of a non-malignant hemoglobinopathy, an immunodeficiency and cancer. In some embodiments, the subject has, suffers from or is otherwise affected by a metabolic disorder (e.g., a metabolic disorder selected from the group consisting of glycogen storage diseases, mucopolysccharidoses, Gaucher's Disease, Hurlers Disease, sphingolipidoses and metachromatic leukodystrophy). In some embodiments, the subject has, suffers from or is otherwise affected by a malignancy. In some embodiments, the subject has, suffers from or is otherwise affected by a disease or condition selected from the group consisting of severe combined immunodeficiency, Wiscott-Aldrich syndrome, hyper IGM syndrome, Chédiak-Higashi disease, hereditary lymphohistiocytosis, osteopetrosis, osteogenesis imperfect, the storage diseases, thalassemia major, sickle cell disease, systemic sclerosis, systemic lupus erythematosus, multiple sclerosis, and juvenile rheumatoid arthritis. For example, in certain embodiments the subject suffers from a malignancy selected from the group consisting of hematologic cancers (e.g., leukemia, lymphoma, multiple myeloma and myelodysplastic syndrome) and neuroblastoma.

In certain aspects, the immunotoxin compositions disclosed herein may be used to induce solid organ transplant tolerance (e.g., inducing immunogenic tolerance in connection with kidney transplant). In such embodiments, the immunotoxin compositions and methods disclosed herein may be used to deplete or ablate a population of cells from a target tissue (e.g., to deplete HSCs from the bone marrow stem cell niche). Following such depletion of cells from the target tissues, a population of stem or progenitor cells from the organ donor (e.g., HSCs from the organ donor) may be administered to the transplant recipient and following the engraftment of such stem or progenitor cells, a temporary of stable mixed chimerism achieved, thereby enabling long-term transplant organ tolerance without the need for further immunosuppressive agents.

In certain aspects, the subject is a mammal (e.g., the subject is a human). In certain aspects, the subject is immunocompetent. Alternatively, in certain embodiments, the subject is immunocompromised.

Also disclosed herein are methods of identifying a candidate agent for selectively depleting or ablating an endogenous stem cell population, such methods comprising the steps of: (a) contacting a sample comprising the stem cell population with a test agent coupled (e.g., functionally coupled) to a toxin; and (b) detecting whether one or more cells of the stem cell population are depleted or ablated from the sample; wherein the depletion or ablation of one or more cells of the stem cell population following the contacting step identifies the test agent as a candidate agent. In some embodiments, the cell is contacted with the test agent for at least about 2-24 hours.

In some embodiments, the cell is a human cell. In some embodiments, the cell is a mouse cell. In certain embodiments, the cell is a stem cell. In certain aspects, such cells comprise hematopoietic stem cells or progenitor cells. In some embodiments, the hematopoietic stem cells or progenitor cells express one or more markers selected from the group of markers consisting of HLA-DR, CD11a, CD18, CD34, CD41/61, CD43, CD45, CD49d (VLA-4), CD49f (VLA-6), CD51, CD58, CD71, CD84, CD90, CD97, CD117

(c-kit), CD133, CD134, CD162, CD166, CD184 (CXCR4), CD205 and CD361. In some embodiments, the human hematopoietic stem cells or progenitor cells express CD34.

In certain embodiments, the targeted cells comprise human hematopoietic stem cells expressing one or more markers that may be targeted and to which the agents that comprise the immunotoxin selectively bind, such markers selected from the group consisting of CD7, CDw12, CD13, CD15, CD19, CD21, CD22, CD29, CD30, CD33, CD34, CD36, CD38, CD40, CD41, CD42a, CD42b, CD42c, CD42d, CD43, CD45, CD45RA, CD45RB, CD45RC, CD45RO, CD48, CD49b, CD49d, CD49e, CD49f, CD50, CD53, CD55, CD64a, CD68, CD71, CD72, CD73, CD81, CD82, CD85A, CD85K, CD90, CD99, CD104, CD105, CD109, CD110, CD111, CD112, CD114, CD115, CD117, CD123, CD124, CD126, CD127, CD130, CD131, CD133, CD135, CD138, CD151, CD157, CD162, CD164, CD168, CD172a, CD173, CD174, CD175, CD175s, CD176, CD183, CD191, CD200, CD201, CD205, CD217, CD220, CD221, CD222, CD223, CD224, CD225, CD226, CD227, CD228, CD229, CD230, CD235a, CD235b, CD236, CD236R, CD238, CD240, CD242, CD243, CD277, CD292, CDw293, CD295, CD298, CD309, CD318, CD324, CD325, CD338, CD344, CD349, and CD350.

In certain embodiments, the targeted cells comprise human hematopoietic stem cells expressing one or more markers that may be targeted and to which the agents that comprise the immunotoxin selectively bind, such markers selected from the group consisting of CD11a, CD18, CD37, CD47, CD52, CD58, CD62L, CD69, CD74, CD97, CD103, CD132, CD156a, CD179a, CD179b, CD184, CD232, CD244, CD252, CD302, CD305, CD317, and CD361.

In certain embodiments, the test agent is an antibody. In certain aspects, the test agent is a ligand. In some embodiments, the toxin is internalized by the one or more cells of the HSC or progenitor cell population. In some embodiments, the internalization comprises receptor-mediated internalization. In certain embodiments, the toxin is selected from the group of toxins consisting of saporin, diphtheria toxin, pseudomonas exotoxin A, Ricin A chain derivatives, a small molecule toxin and combinations thereof. In certain aspects, the toxin is selected from the group of toxins consisting of abrin toxin, modeccin toxin, gelonin toxin, momordin toxin, trichosanthin toxin, luffin toxin and combinations thereof. In some embodiments, the toxin is or comprises an amatoxin (e.g., α-amanitin).

While certain embodiments disclosed herein contemplate the use of, for example, an agent-toxin conjugate to deplete or condition a tissue (e.g., bone marrow tissue), or to receptor-mediated internalization of a toxin, the inventions disclosed herein are not limited to such embodiments. Rather, contemplated herein are any methods that may be used to selectively deliver a toxin intracellularly to the cells of a target tissue. For example, in certain embodiments, disclosed herein are methods of delivering toxins intracellularly using pore-mediated internalization.

In certain embodiments, disclosed herein are methods of conditioning a subject for engraftment, such methods comprising selectively depleting or ablating an endogenous stem cell population in a target tissue (e.g., bone marrow tissue) of the subject by: (a) administering to the subject an effective amount of a pore-forming chimera comprising a mutant protective antigen (mut-PA) coupled (e.g., functionally coupled) to an agent, and thereby forming one or more pores in the cell membrane of the endogenous stem cell population; and (b) administering to the subject an effective amount of a second chimera, wherein the second chimera comprises a factor (e.g., an enzymatic factor) coupled to a toxin, wherein the factor is selected from the group consisting of lethal factor N-terminus (LFN), edema factor N-terminus (EFN) or fragments thereof, and wherein the toxin is internalized by the endogenous stem cell population, thereby selectively depleting or ablating the endogenous stem cell population in the target tissue and conditioning the subject for engraftment.

In certain embodiments, the present inventions are directed to methods of engrafting stem cells in a subject, such methods comprising the steps of: (a) administering to the subject an effective amount (e.g., 1.5 mg/kg) of a pore-forming chimera comprising a mutant protective antigen (mut-PA) coupled to an agent, and thereby forming one or more pores in the cell membrane of the endogenous stem cell population; (b) administering to the subject an effective amount of a second chimera, wherein the second chimera comprises a factor (e.g., an enzymatic factor) coupled to a toxin, wherein the factor is selected from the group consisting of lethal factor N-terminus (LFN), edema factor N-terminus (EFN) or fragments thereof, and wherein the toxin is internalized by the endogenous stem cell population, thereby depleting or ablating the endogenous stem cell population in the target tissue (e.g., bone marrow tissue); and (c) administering a stem cell population to the target tissue of the subject, wherein the administered stem cell population engrafts in the target tissue of the subject. In some embodiments, the stem cell population is administered to the target tissues of the subject after the toxin (e.g., a diphtheria toxin A chain chimera fusion to LFN (LFN-DTA)) has cleared or dissipated from the subject's target tissues.

In some embodiments, the agent is selected from the group consisting of a scfv, a Fab, a discfv, a biscFv, a tri-scfv, a tandem scfv, an aptamer, an antibody and a ligand. In certain embodiments, the agent is a single-chain variable fragment (scFv). In certain aspects, the agent is a bispecific antibody.

In still other embodiments, the agent is a ligand. For example, such a ligand may be selected from the group of ligands consisting of stem cell factor (SCF), CXCL12: Stromal derived factor 1 (SDF1), Angiopoietin 1 to 4 (Ang1, Ang2, Ang3, Ang4), TPO (thrombopoietin), Erythropoietin, FLT3L, VLA4, VLA6, IL-1, IL-3, IL-6, IL-18, G-CSF, Oncostatin M, LIF and combinations thereof.

In certain embodiments of the methods disclosed herein, the toxin is internalized by a pore-mediated internalization. In certain embodiments, the toxin is saporin. In certain embodiments, the toxin inactivates ribosomes. In certain embodiments, the toxin inhibits protein synthesis. In certain aspects, the toxin is selected from the group of toxins consisting of saporin, diphtheria toxin, pseudomonas exotoxin A, Ricin A chain derivatives, small molecule toxins and combinations thereof. In some embodiments, the toxin is or comprises an amatoxin (e.g., α-amanitin). In some embodiments, the toxin is selected from the group consisting of abrin toxin, modeccin toxin, gelonin toxin, momordin toxin, trichosanthin toxin, luffin toxin and combinations thereof.

In certain embodiments, the endogenous stem cell population comprises hematopoietic stem cells. In certain embodiments, the hematopoietic stem cells or progenitor cells comprise or express one or more markers. For example, in certain embodiments the hematopoietic stem cells or progenitor cells express one or more markers selected from the group of markers consisting of: CD13, CD33, CD34, CD44, CD45, CD49d: VLA-4, CD49f: VLA-6, CD59, CD84: CD150 family, CD90: Thy1, CD93, CD105: Endoglin, CD117: cKit/SCF receptor, CD123: IL-3R, CD126: IL-6R, CD133, CD135: Flt3 receptor, CD166: ALCAM, CD184: CXCR4, Prominin 2, Erythropoietin R, Endothelial Cell-Selective Adhesion Molecule, CD244, Tie1, Tie2, MPL, G-CSFR or CSF3R, IL-1R, gp130, Leukemia inhibitory factor Receptor, Embigin and IL-18R. In certain embodiments, the hematopoietic stem cells or progenitor cells express one or more markers selected from the group consisting of HLA-DR, CD11a, CD18, CD34, CD41/61, CD43, CD45, CD47, CD58, CD71, CD84, CD97, CD117 (c-kit), CD133, CD162, CD166, CD205 and CD361. In certain aspects, the agent selectively binds to the marker. In certain aspects, upon binding of the agent to the marker, the immunotoxin is internalized by the cells expressing such marker.

In certain embodiments, the subject is a mammal. In certain embodiments, the mammal is a human. In certain embodiments, the methods and compositions disclosed herein may be used to treat, cure or otherwise ameliorate a disease or condition in a subject affected thereby. Accordingly, in certain aspects, the subject has a non-malignant hemoglobinopathy. For example, such a subject may be affected by a hemoglobinopathy selected from the group consisting of sickle cell anemia, thalassemia, Fanconi anemia, and Wiskott-Aldrich syndrome.

In certain aspects, the subject has an immunodeficiency. For example, in certain embodiments, the immunodeficiency is a congenital immunodeficiency. Alternatively, in certain aspects the immunodeficiency is an acquired immunodeficiency. For example, an acquired immunodeficiency selected from the group consisting of HIV and AIDS.

In still other embodiments, the subject has or is otherwise affected by the stem cell disorder selected from the group of disorders consisting of a non-malignant hemoglobinopathy, an immunodeficiency and cancer.

In various embodiments of any aspect of the present inventions, the compositions and methods disclosed herein further comprise administering to the subject one or more mobilizing agents (e.g., a combination of a CXCR2 agonist and a CXCR4 antagonist). For example, the compositions disclosed herein may be co-administered with one or more mobilizing agents and/or may be administered subsequent to the administration of the one or more mobilizing agents (e.g., 15 minutes post-administration of the mobilizing agent). In certain aspects, the mobilizing agent is or comprises filgrastim (GCSF). In certain aspects, the mobilizing agent is selected from the group consisting of a CXCR2 agonist (e.g., Gro-beta), a CXCR4 antagonist (e.g., plerixafor), and combinations thereof. In certain embodiments, the mobilizing agent comprises Gro-beta. In certain aspects, the mobilizing agent comprises Gro-betaΔ4. In certain embodiments, the mobilizing agent comprises plerixafor. In certain aspects, the mobilizing agents comprise Gro-beta and plerixafor. In certain aspects, the mobilizing agents comprise Gro-betaΔ4 and plerixafor. In certain aspects, the mobilizing agent comprises a heparan sulfate inhibitor.

The above discussed, and many other features and attendant advantages of the present inventions will become better understood by reference to the following detailed description of the invention.

BRIEF DESCRIPTION OF THE DRAWINGS

FIG. 1 illustrates the CD45 monoclonal antibody in conjunction with a streptavidin-saporin conjugate to create an immunotoxin to CD45 (CD45-SAP). Also depicted is the mechanism by which such CD45-SAP causes cell death of the hematopoietic stem cells (HSCs) or progenitor cells expressing CD45.

FIG. 2A illustrates the frequency of hematopoietic stem cells (HSCs) in bone marrow harvested 8 days post-conditioning and demonstrates 98% depletion of HSCs in the CD45-SAP group, but no depletion was observed in the non-biotin-labeled antibody plus saporin group. FIG. 2B shows short-term progenitor cell activity as assessed by colony forming counts of the bone marrow fraction harvested 8 days post-conditioning. FIG. 2C shows total bone marrow cellularity 8 days post conditioning. FIG. 2D illustrates a time course analysis of peripheral blood donor chimerism of transplanted mice. FIG. 2E illustrates donor chimerism at 2 months after transplantation performed at various days post-CD45-SAP administration. FIG. 2F depicts overall tri-lineage distribution at 8 months post-transplantation in non-conditioned control and in CD45-SAP conditioned mice. FIG. 2G illustrates donor chimerism within each of the 3 lineages at 8 months post-transplantation in both control non-conditioned mice and in CD45-SAP conditioned mice. * denotes p value <0.05; N.S. denotes statistically not significant.

FIG. 3A shows red blood cell counts, FIG. 3B shows neutrophil counts (counts within the gray box would represent neutropenia), FIG. 3C shows platelet counts (counts within the gray box would represent thrombocytopenia), and FIG. 3D shows lymphocyte counts (B- and T-cells), as assessed over a 100-day period in mice conditioned with CD45-SAP. The results presented demonstrate that CD45-SAP conditioning is characterized as being non-myeloablative. * denotes p value <0.05; N.S. denotes statistically not significant.

As shown in FIG. 4A, EL4 and EML cell death that was induced by the CD45-SAP group (triangles), while the same was not observed in the non-biotin-labeled antibody plus saporin group (circles). FIG. 4B illustrates the $IC_{50}$ observed with CD45-SAP relative to that observed in the non-biotin-labeled antibody plus saporin group. FIG. 4C illustrates the 24 hour internalization observed in an alexa-fluor 488 (AF488)-labeled CD45 antibody.

FIGS. 5A-5C illustrate the HSC frequency percentage (FIG. 5A), colonies per femur (FIG. 5B) and total cells per femur (FIG. 5C) in animals administered the CD45-SAP immunotoxin. As illustrated in FIG. 5D, at eight days post-treatment with a single i.v. dose of the CD45-SAP immunotoxin, the HSCs were depleted from the bone marrow tissue relative to the control. Similarly, FIG. 5E confirms functional HSC loss in completive transplant.

FIG. 6A generally illustrates one embodiment of the present invention wherein a CD45-SAP immunotoxin is administered to a mouse, followed by engraftment with a single dose of exogenous cells. FIG. 6B illustrates the percent chimerism 4 months following transplant. FIGS. 6C and 6D compare the percent donor chimerism in both conditioned and non-conditioned mice.

FIG. 11A shows the percent donor myeloid chimerism in each of the three conditions evaluated. As illustrated in FIGS. 11B-11D, red blood cell, hemoglobin and reticulocyte levels returned to normal.

FIG. 12A presents the results of a native PAGE gel analysis of sickle hemoglobin (Hbs) and normal hemoglobin (Hba) in animals that were conditioned with CD45-SAP followed by transplantation, and evidences the correction of sickle cell. FIG. 12B presents the results of a blood smear and staining in animals that were conditioned with CD45-SAP followed by transplantation, and further evidences the correction of sickle cell disease in the animals.

FIG. 14A depicts an experimental outline for assessing ability of immunotoxins to deplete HSCs in immunocompetent mice. FIG. 14B shows the dose-dependent effects of CD45-SAP on progenitor colony forming cell (CFC) and HSC depletion assessed 8 days post-administration. Data represent mean±SD (n=5 mice/group). FIG. 14C demonstrates that CD45-SAP depletes HSCs while non-biotinylated CD45 antibody in the presence of streptavidin-saporin does not deplete HSCs. Data represent mean±SD (n=5 mice/group). FIG. 14D shows that the CD45-SAP clone 104 kills EML progenitor cells in vitro while non-biotinylated antibody in presence of streptavidin-saporin does not affect viability. FIG. 14E shows quantification of CD45 receptor internalization in EL4 cells using clone 104. Data represents mean±SD of a representative experiment. * indicates p value <0.05;  indicates p value <0.01; * indicates p value <0.001; n.s. indicates not significant (p value >0.05).

FIG. 15A shows that HSC depletion activity of candidate immunotoxins assessed in bone marrow 6 days post-administration. Data represent mean±range (n=2 mice/group).

FIG. 15B depicts an investigation of various ratios of CD45 antibody to streptavidin-saporin on HSC depletion activity. Data represent mean±SD (n=4 mice/group). FIG. 15C shows peripheral chimerism 4 months after competitive transplantation of bone marrow harvested from control or CD45-SAP conditioned mice demonstrates depletion of functional HSCs by CD45-SAP. Data represent mean±SD (n=5 mice/group). FIG. 15D shows that CD45-SAP clone 104 does not deplete HSCs in CD45.1 mice. Data represent mean±SD (n=5 mice/group). FIG. 15E presents in vitro $IC_{50}$ values against EL4 and EML cell lines after 72 h incubation with CD45-SAP clones 104 and 30-F11. Data represent mean±SD of 3 independent experiments. FIG. 15F shows HSC depletion by CD45-SAP created from clones 104 and 30-F11. Data represent mean±SD (n=4 mice/group). FIG. 15G shows in vivo persistence of AF488-labelled CD45 antibody clones 104 and 30-F11 in peripheral white blood cells, splenocytes and LKS bone marrow progenitor cells 24 h post-administration. Data represent mean±SD (n=3 mice/group). * indicates p value <0.05;  indicates p value <0.01; * indicates p value <0.001; n.s. indicates not significant (p value >0.05).

FIG. 16A depicts an experimental outline for assessing transplantation window following CD45-SAP conditioning and transplantation of either CD45.1 or CD45.2-GFP whole bone marrow cells. FIG. 16B shows donor chimerism (4 months post-transplantation) of CD45.2 GFP or CD45.1 cells injected various days post CD45-SAP conditioning. Control represents non-conditioned mice receiving transplant. Data represent mean±SD (n=5 mice/group). FIG. 16C illustrates representative flow cytometry plots illustrating donor cells in peripheral blood post-transplantation in control or CD45-SAP conditioned mice. FIG. 16D shows Long term assessment of peripheral blood chimerism following CD45.2-GFP cell transplantation 8 days post CD45-SAP conditioning. Data represent mean±SD (n=5 mice/group). FIG. 16E depicts the contribution of donor cells to myeloid, B- and T-cells in CD45-SAP conditioned mice versus overall distribution in untreated control mice. Data represent mean±SD (n=5 mice/group). FIG. 16F illustrates donor myeloid chimerism 4 months after transplantation of 2,000 purified HSCs (LKS CD48−CD150+ or LKS CD34−CD150+) in non-conditioned control and CD45-SAP conditioned mice. Data represent mean±SD (n=5 mice/group). * indicates p value <0.05;  indicates p value <0.01; * indicates p value <0.001; n.s. indicates not significant (p value >0.05).

FIG. 17A demonstrate chimerism in peripheral blood and bone marrow HSC population 4 months post transplantation. Data represent mean±SD (n=5 mice/group). FIG. 17B shows long term assessment of peripheral blood chimerism following CD45.1 cell transplantation 8 days post CD45-SAP conditioning. Data represent mean±SD (n=5 mice/group). FIG. 17C shows blood chimerism 4-months post serial transplantation of marrow from CD45-SAP conditioned mice transplanted with either CD45.2-GFP or CD45.1 cells. Data represent mean±SD (n=5 mice/group). FIG. 17D compares CD45-SAP and 5Gy total body irradiation (TBI) achieve similar levels of chimerism (70-80%) 4 months following transplantation of CD45.1 cells while ACK2-conditioning fails to enable engraftment (<5%). Data represent mean±SD (n=5 mice/group), with the exception of ACK2 (n=2 mice). FIG. 17E shows four month chimerism following transplantation of low cell dose (1 million bone marrow cells) into mice conditioned with CD45-SAP, TBI (5Gy) or the combination. Data represent mean±SD (n=5 mice/group). * indicates p value <0.05;  indicates p value <0.01; * indicates p value <0.001; n.s. indicates not significant (p value >0.05).

FIG. 18A shows the relative bone marrow cellularity at various time points after CD45-SAP or 5Gy total body irradiation (TBI). Data represent mean percentage relative to untreated mice±SEM (n=4 mice/group). FIG. 18B shows the relative colony forming cell (CFC) activity of bone marrow cells harvested at various times post CD45-SAP or 5Gy total body irradiation (TBI). Data represent mean percentage relative to untreated mice±SEM (n=4 mice/group). FIG. 18C shows the relative immunophenotypic quantification of HSCs in bone marrow harvested at various times post CD45-SAP or 5Gy TBI. Data represent mean percentage relative to untreated mice±SEM (n=4 mice/group). FIG. 18D shows in vivo microscopy of calvarium bone to assess vascular integrity. Control mice, or mice treated with CD45-SAP or 5Gy TBI (2 days post-conditioning) were i.v. injected with high molecular weight (2 MDa) dextran-rhodamine to assess vascular integrity (red channel). Images were captured 20 minutes post-dextran administration and bone surface is shown in blue channel. * indicates p value <0.05;  indicates p value <0.01; * indicates p value <0.001; n.s. indicates not significant (p value >0.05).

FIG. 20A shows the relative levels of peripheral myeloid cells post CD45-SAP or 5Gy TBI. FIG. 20B shows Kaplan-Meier survival curve following systemic *Candida albicans* challenge 2 days post-conditioning and in non-conditioned control (n=10 mice/group). FIG. 20C shows relative levels of CD3+ T-cells post CD45-SAP or 5Gy TBI. Data in FIGS. 20A and 20C represent mean percentage relative to untreated control±SEM (n=4 mice/time point). FIG. 20D shows hematoxylin and eosin staining of thymus (500 micron scale bar) and thymic cortex (50 micron scale bar) from control, CD45-SAP or 5Gy TBI conditioned mice harvested 2 days post-conditioning. FIG. 20E shows the absolute number of T-cell receptor excision circles (TRECs) per mg of thymus tissue 3 days post-conditioning (n=4 mice/group). * indicates p value <0.05;  indicates p value <0.01; * indicates p value <0.001; n.s. indicates not significant (p value >0.05).

FIG. 21A shows Wright Giemsa staining and confirms presence of mature neutrophils (indicated by arrows) in peripheral blood of mice 6 days post CD45-SAP administration (20 micron scale bar). FIG. 21B shows relative levels of B-cells post CD45-SAP or 5Gy TBI (mean±SEM, n=4 mice/group). FIG. 21C shows thymus mass of control, CD45-SAP or 5Gy TBI conditioned mice harvested 3-days post treatment. Data represents mean±SD (n=4 mice/group). Relative levels of (FIG. 21D) red blood cells (RBCs), (FIG. 21E) hemoglobin, (FIG. 21F) hematocrit, and (FIG. 21G) platelets at various time points following CD45-SAP or 5Gy TBI. Data represent mean percentage relative to untreated control±SEM (n=4 mice/time point). * indicates p value <0.05;  indicates p value <0.01; * indicates p value <0.001; n.s. indicates not significant (p value >0.05).

FIG. 22A depicts an experimental outline for CD45-SAP conditioning and transplantation in sickle mice (6 mice/group, 3 groups). FIG. 22B shows donor myeloid chimerism 4 months post-transplantation in the three groups of sickle mice transplanted under the conditions in FIG. 22A. Data represent the mean±SD (n=6 mice/group). FIG. 22C shows an assessment of red blood cell (RBC), hemoglobin, hematocrit and reticulocyte numbers in wild type control, sickle control and Group A (corrected sickle mice) 4 months post-transplantation. Data represent the mean±SEM (n=6 mice/group). FIG. 22D shows results of a native-PAGE analysis of normal (Hba) and sickle (Hbs) hemoglobin protein in blood from wild type control, sickle and Group A mice (2 representative mice from each group). FIG. 22E shows representative peripheral blood smears of wild type, sickle and Group A mice with sickle cells indicated by arrows. FIG. 22F shows representative spleens from wild type control, sickle and Group A mice. * indicates p value <0.05;  indicates p value <0.01; * indicates p value <0.001; n.s. indicates not significant (p value >0.05).

FIG. 23A illustrates that HSC depletion in sickle mice 8 days post-administration of various doses of CD45-SAP. Data represent the mean±SEM (n=3 mice/group). FIG. 23B depicts a detailed experimental outline for CD45-SAP conditioning and transplantation in sickle mice (3 groups of n=6 mice/group) with doses of immunotoxin and numbers of whole bone marrow cells transplanted indicated. FIG. 23C shows red blood cell counts, (FIG. 23D) hemoglobin levels, (FIG. 23E) reticulocyte frequency for wild type control, sickle control and the 3 groups of CD45-SAP conditioned and transplanted sickle mice. Data in FIGS. 23C-23E represent the mean±SEM (n=6 mice/group). FIG. 23F shows spleen mass 4 months post transplantation for wild type control, sickle control and the 3 groups of CD45-SAP conditioned and transplanted sickle mice. Data represent the mean±SD (n=3 mice/group). * indicates p value <0.05;  indicates p value <0.01; * indicates p value <0.001; n.s. indicates not significant (p value >0.05).

FIG. 25A shows the number of phenotypic HSC 6 days post-administration of the antibody-toxin conjugate. FIG. 25B illustrates the depletion of HSCs in vivo by various antibody-toxin conjugates 6-8 days post-administration.

As shown in FIG. 32, the non-antagonist 2B8-SAP conjugate achieved efficient donor cell engraftment in fully immunocompetent animals, thus greatly expanding scope of diseases to include non-SCID conditions.

FIG. 35 depicts the mechanism of translocation using lethal factor (LF) and edema factor (EF) and protective antigen to deplete HSCs or progenitor cells.

FIG. 36 illustrates the in vitro activity of LFN-DTA against human hematopoietic stem cells (HSCs). Human mobilized peripheral blood CD34+ HSCs were treated in vitro with various concentrations of LFN-DTA immunotoxin in the presence of 10 nM WT-PA for 96 hours and cell viability was assessed using MTS assay (Promega). As illustrated, 100% cell death was observed at 1 femtomolar concentration of LFN-DTA, demonstrating LFN-DTA can be used to enable potent killing of human HSCs.

As illustrated in FIG. 40B, CD45-SAP and CD117-SAP enabled efficient donor cell engraftment in comparison to non-conditioned control mice (at least n=3 mice/group).

As illustrated in FIG. 41A, 8 week old immuno-compromised NSG mice were conditioned with 2 Gy irradiation, 3 mg/kg CD45.1-SAP or 1.5 mg/kg CD117-SAP and transplanted with human cord blood CD34+ donor cells 6-days post immunotoxin. Total human donor chimerism was assessed in the peripheral blood 16-weeks post-transplantation, (n=5 mice/group) and is depicted in FIG. 41B.

As shown in FIG. 42C, human donor cells in the bone marrow primarily consisted of B-cells with some myeloid cells and few T-cells.

DETAILED DESCRIPTION OF THE INVENTION

Figures 2A, 2B, 2C, 2D, 2E, 2F, 2G:
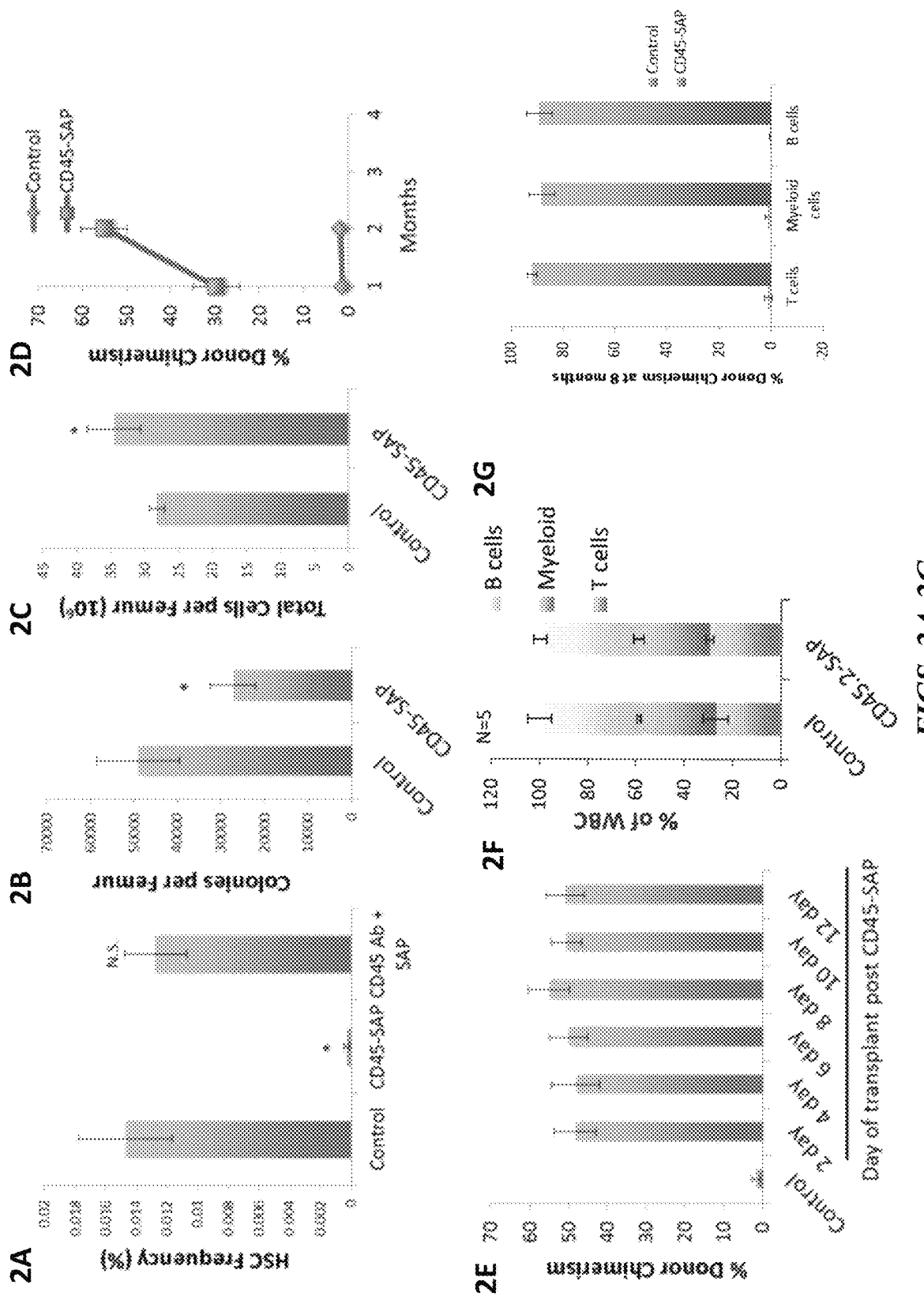
FIGS. 2A-2G demonstrate the results of several studies evaluating the effects of the anti-CD45 mouse monoclonal antibody in conjunction with a streptavidin-saporin conjugate to create an immunotoxin to CD45 (CD45-SAP).

The compositions and methods disclosed herein generally relate to compositions, methods, therapies and regimens that are useful for conditioning a subject's tissues for engraftment or transplant (e.g., hematopoietic stem cell transplant). In particular, such compositions and methods selectively target a marker (e.g., a cell surface marker such as the CD45 or CD117 receptor) and facilitate the intracellular delivery of an immunotoxin to one or more cells (e.g., CD45+ or CD117+ cells) of the target tissue, for example, hematopoietic stem cells (HSCs) and/or progenitor cells in the bone marrow tissue of a subject. By selectively targeting cells expressing a selected marker (e.g., CD45 or CD117), the compositions and methods disclosed herein are able to exert their cytotoxic effect on those targeted cells, while sparing, minimizing, and in certain instances eliminating, adverse effects on non-targeted cells and tissues. For example, in certain instances, the compositions and methods disclosed herein selectively ablate or deplete the endogenous stem cell niche of a target tissue (e.g., bone marrow tissue); however, in contrast to traditional conditioning regimens (e.g., the reduced conditioning regimen for sickle cell anemia disclosed by Bolanos-Meade, et al., *Blood* (2012), 120(22): 4286), such compositions and methods do not induce life-threatening neutropenia, thrombocytopenia and/or anemia in the subject.

In certain aspects, the compositions and methods disclosed herein relate to the targeting, ablation and/or depletion of hematopoietic stem or progenitor cells (HSPCs) residing in the target tissues of a subject, for example, hematopoietic stem or progenitor cells within a stem cell niche (e.g., a subject's bone marrow). As used herein, "hematopoietic stem cells" refers to stem cells that can differentiate into the hematopoietic lineage and give rise to all blood cell types such as white blood cells and red blood cells, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells). Stem cells are defined by their ability to form multiple cell types (multipotency) and their ability to self-renew. Human hematopoietic stem cells can be identified, for example by cell surface markers such as CD34+, CD90+, CD49f+, CD38− and CD45RA−. Murine hematopoietic stem cells can be identified, for example by cell surface markers such as CD34−, CD133+, CD48−, CD150+, CD244−, cKit+, Sca1+, and lack of lineage markers (negative for B220, CD3, CD4, CD8, Mac1, Gr1, and Ter119, among others). The compositions and methods described herein may be useful for the depletion or ablation any stem cell, including, but not limited to, peripheral blood stem cells, bone marrow stem cells, umbilical cord stem cells, genetically modified stem cells, etc.

As used herein, the term "hematopoietic progenitor cells" encompasses pluripotent cells which are committed to the hematopoietic cell lineage, generally do not self-renew, and are capable of differentiating into several cell types of the hematopoietic system, such as granulocytes, monocytes, erythrocytes, megakaryocytes, B-cells and T-cells, including, but not limited to, short term hematopoietic stem cells (ST-HSCs), multi-potent progenitor cells (MPPs), common myeloid progenitor cells (CMPs), granulocyte-monocyte progenitor cells (GMPs), megakaryocyte-erythrocyte progenitor cells (MEPs), and committed lymphoid progenitor cells (CLPs). The presence of hematopoietic progenitor cells can be determined functionally as colony forming unit cells (CFU-Cs) in complete methylcellulose assays, or phenotypically through the detection of cell surface markers (e.g., CD45, CD34+, Ter119−, CD16/32, CD127, cKit, Sca1) using assays known to those of skill in the art.

The present inventions contemplate ablating or depleting hematopoietic stem cells and/or progenitor cells for any purpose which would be desirable to the skilled artisan. In some embodiments, the hematopoietic stem cells and/or progenitor cells are ablated or depleted from the target tissues of a subject (e.g., the stem cell niche) to condition the subject for engraftment of transplanted hematopoietic stem cells and/or progenitors cells, for example by decreasing the number of or eliminating hematopoietic stem cells and/or progenitor cells in a stem cell niche (e.g., bone marrow) into which the transplanted cells can engraft.

While certain aspects of the present invention contemplate the ablation or depletion of, for example, hematopoietic stem cells from the stem cell niche, the present inventions may also be useful for ablating or depleting non-hematopoietic stem cells that are involved in maintaining the stem cell niche. For example, the compounds and methods disclosed herein may be used to target non-HSC, hematopoietic subsets that play a role in niche maintenance of hematopoietic stem cells. Such hematopoietic subsets that may be targeted, ablated or depleted using the compositions and methods disclosed herein include, for example, T-cells expressing CD4, CD3 or CD8; B-cells expressing B220 or CD19; and myeloid cells expressing Gr-1 or Mac-1 (CD11b).

As used herein the terms "ablate" and "ablation" generally refer to the partial or complete removal of a population of cells (e.g., hematopoietic stem cells or progenitor cells) from the target tissues (e.g., bone marrow tissues of a subject). In certain aspects, such ablation comprises a complete removal or depletion of such cells from the target tissue. Alternatively, in other aspects, such ablation is a partial removal or depletion of such cells (e.g., HSCs or progenitor cells) from the target tissue. For example, in certain aspects, the methods and compositions disclosed herein result in at least about 5%, 10%, 12.5%, 15%, 20%, 25%, 30%, 35%, 40%, 45%, 50%, 55%, 60%, 65%, 70%, 75%, 80%, 85%, 90%, 92.5%, 95%, 97.5%, 98% or 99% depletion of the cells (e.g., HSCs or progenitor cells) of the target tissue.

The CD45 receptor is a unique and ubiquitous membrane glycoprotein that is expressed on almost all hematopoietic cells. Similarly, CD117 is a cytokine receptor that is expressed on the surface of hematopoietic stem cells, progenitor cells, as well as other cell types. The inventions disclosed herein are based in-part upon the discovery that certain markers (e.g., cell surface markers such as CD45 and CD117) have internalizing properties that may be exploited to facilitate the intracellular delivery of a toxin (e.g., a toxin such as saporin) to the cells of a target tissue and thereby induce cell death, as generally illustrated in FIG. 1. Accordingly, in certain embodiments the agents (e.g., antibodies and/or ligands) and compositions disclosed herein are characterized as being internalizing and thus can cause or otherwise facilitate the intracellular delivery of one or more immunotoxins to cells of the target tissue that express a targeted marker (e.g., a targeted cell surface marker).

In certain aspects, the inventions disclosed herein contemplate the selection of one or more markers (e.g., a cell surface marker) to facilitate the selective targeting of the agents to the cells of a target tissue. As used herein, the term "selectively" means that the agent (e.g., an antibody) preferentially or discriminatorily recognizes and/or binds to a marker or a fragment or epitope of such marker (e.g., a cell surface marker). Exemplary antibody agents that selectively recognize and/or bind a cell surface marker (e.g., CD45, CD117 and CD34) and that may be used in accordance with the present inventions include, clone 104, clone 30F11, clone ACK2, clone 2B8, clone 3C11, clone MEM-28, clone HI130, clone 581 and clone 4H11. In certain aspects, the agent comprises an antibody that selectively recognizes and/or binds to the CD34 marker (e.g., clone 581 or clone 4H11). In certain aspects, the agent comprises an antibody that selectively recognizes and/or binds to the CD45 marker (e.g., clone MEM-28 or clone HI130). In certain aspects, the agent is an antibody selected from the group consisting of clone L243, clone TS2/4, clone TS1/18, clone 581, clone 4H11, clone A2A9/6, clone CD43-10G7, clone BHPT-1, clone orb12060, clone 2D1, clone CC2C6, clone TS2/9, clone CY1G4, clone OKT9, clone CD84.1.21, clone VIM3b, clone A3C6E2, clone EMK08, clone TMP4, clone KPL-1, clone 3a6, clone HD83 and clone MEM-216. By selectively targeting the cells of the target tissues, the methods and compositions disclosed herein may reduce, limit or otherwise avoid toxicities that have historically plagued traditional conditioning regimens and that result in life-threatening complications.

As used herein, the term "marker" generally refers to any protein, receptor, antigen, carbohydrates, lipids or other moieties that may be located or expressed on the surface of the cells of the target tissue and that can be used to discriminate a cell population. In particular, such markers may be used to selectively target the agents that comprise the immunotoxin compositions disclosed herein to the cells of the target tissue. While certain embodiments disclosed herein contemplate the selective targeting of a cell using, for example the CD34, CD45 and/or CD117 markers, the inventions are not limited to those markers. Rather, the present inventions contemplate the selection and use of any markers (e.g., cell surface markers) that may be useful or suitable for selectively targeting a cell population, inclusive of any yet to be discovered markers. Preferably, the selected marker is selectively expressed on the surface of the target cell population, thereby facilitating the selective or discriminatory targeting of such cell population using the agents (e.g., antibodies and/or ligands) disclosed herein. For example, in certain aspects, the selected marker is expressed on hematopoietic stem cells or progenitor cells. Exemplary markers may be selected from the group of markers consisting of HLA-DR, CD11a, CD18, CD34, CD41/61, CD43, CD45, CD49d (VLA-4), CD49f (VLA-6), CD51, CD58, CD71, CD84, CD90, CD97, CD117 (c-kit), CD133, CD134, CD162, CD166, CD184 (CXCR4), CD205 and CD361. In certain embodiments, the selected marker is only expressed on the targeted cell population (e.g., the target HSC population), thereby limiting or avoiding the "off-target" effects that have limited the utility of traditional conditioning regimens.

In certain embodiments, the selection of a marker may be made based upon comparing the detected expression of such a marker (e.g., a cell surface marker) on a target cell relative the expression of such marker on a control population of cells. For example, the expression of a marker on a HSC or progenitor cell can be compared to the mean expression of the same marker on other cells.

In certain embodiments, the marker is a receptor. Exemplary human receptors that may be used or selected as markers in accordance with the inventions disclosed herein may be selected from the group of markers consisting of CD13, CD33, CD34, CD44, CD45, CD49d: VLA-4, CD49f: VLA-6, CD59, CD84: CD150 family, CD90: Thy1, CD93, CD105: Endoglin, CD117: cKit/SCF receptor, CD123: IL-3R, CD126: IL-6R, CD133, CD135: Flt3 receptor, CD166: ALCAM, CD184: CXCR4, Prominin 2, Erythropoietin R, Endothelial Cell-Selective Adhesion Molecule, CD244, Tie1, Tie2, MPL, G-CSFR or CSF3R, IL-1R, gp130, Leukemia inhibitory factor Receptor, oncostatin M receptor, Embigin and IL-18R.

In certain aspects, exemplary markers that are expressed on human hematopoietic stem cells, that may be targeted and to which the agents that comprise the immunotoxin selectively bind may be selected from the group consisting of CD7, CDw12, CD13, CD15, CD19, CD21, CD22, CD29, CD30, CD33, CD34, CD36, CD38, CD40, CD41, CD42a, CD42b, CD42c, CD42d, CD43, CD45, CD45RA, CD45RB, CD45RC, CD45RO, CD48, CD49b, CD49d, CD49e, CD49f, CD50, CD53, CD55, CD64a, CD68, CD71, CD72, CD73, CD81, CD82, CD85A, CD85K, CD90, CD99, CD104, CD105, CD109, CD110, CD111, CD112, CD114, CD115, CD117, CD123, CD124, CD126, CD127, CD130, CD131, CD133, CD135, CD138, CD151, CD157, CD162, CD164, CD168, CD172a, CD173, CD174, CD175, CD175s, CD176, CD183, CD191, CD200, CD201, CD205, CD217, CD220, CD221, CD222, CD223, CD224, CD225, CD226, CD227, CD228, CD229, CD230, CD235a, CD235b, CD236, CD236R, CD238, CD240, CD242, CD243, CD277, CD292, CDw293, CD295, CD298, CD309, CD318, CD324, CD325, CD338, CD344, CD349, and CD350.

In some embodiments, exemplary markers that are expressed on human hematopoietic stem cells, that may be targets and to which the agents that comprise the immunotoxin selectively bind may be selected from the group consisting of CD11a, CD18, CD37, CD47, CD52, CD58, CD62L, CD69, CD74, CD97, CD103, CD132, CD156a, CD179a, CD179b, CD184, CD232, CD244, CD252, CD302, CD305, CD317, and CD361.

Exemplary mouse receptors that may be used of selected as markers in accordance with the inventions disclosed herein may be selected from the group consisting of Sca-1, CD150, CD27 and CD201.

Exemplary ligands that may be used or selected as markers in accordance with the inventions disclosed herein may be selected from the group of markers consisting of Stem cell factor (SCF) or cKit ligand, CXCL12: Stromal derived factor 1 (SDF1), Angiopoietin 1 to 4 (Ang1, Ang2, Ang3, Ang4), TPO (thrombopoietin), Erythropoietin, FLT3L, VLA-4, VLA-6, IL-1, IL-3, IL-6, IL-18, G-CSF, Oncostatin M and LIF.

The compositions disclosed herein comprise an agent to facilitating targeting of such composition to, for example, an endogenous hematopoietic stem cell or progenitor cell population in a target tissue of a subject. As used herein, the term "agent" refers to any substance, molecule, compound or moiety, such as an antibody or a ligand or an aptamer, that may be used for, or that otherwise facilitates the targeting or directing of a moiety, such as a toxin coupled to such agent, to one or more cells (e.g., one or more hematopoietic stem cells or progenitor cells in the target tissue of a subject). In certain aspects, the agent selectively targets the cells in a target tissue (e.g., bone marrow tissue), causing the moiety (e.g., a toxin) coupled thereto to be internalized by such cells and thereby ablate or deplete such cells from the target tissue. In certain embodiments, the agent selectively recognizes and/or binds to a marker or to a fragment or epitope of such marker (e.g., a cell surface marker, such as a receptor).

The agents disclosed herein include, without limitation, any agents that can selectively target, bind to or recognize a marker or epitope that may be differentially expressed on the cell surface of the cells of the target tissue. In some embodiments, such agents direct or target the immunotoxins disclosed herein to the cells of the target tissue (e.g., cancer stem cells), thereby depleting or ablating such cells from the target tissue and conditioning such target tissue. In some embodiments, the agent is or comprises a ligand (e.g., a ligand such as stem cell factor). In some embodiments, the agent is or comprises an aptamer. The agents of the present invention are not limited to the foregoing illustrative examples; rather any agent that can selectively target, bind to or recognize a marker or epitope expressed on the cell surface of the cells of target tissues may be used. In certain embodiments, the agent is recombinantly prepared.

In certain aspects, the agent is or comprises an antibody (e.g., a monoclonal or polyclonal antibody). The antibodies of the present invention can be polyclonal or monoclonal, and the term "antibody" is intended to encompass both polyclonal and monoclonal antibodies. For example, in certain aspects the antibody is selected from the group consisting of clone 104, clone 30F11, clone ACK2, clone 2B8, clone 3C11, clone MEM-28, clone HI130, clone 581 and clone 4H11. In certain embodiments, the agent is an antibody comprising a complementarity determining region that is the same as the complementarity determining region for one or more antibodies selected from the group consisting of clone 104, clone 30F11, clone ACK2, clone 2B8, clone 3C11, clone MEM-28, clone HI130, clone 581 and clone 4H11. In certain embodiments, the agent is an antibody that binds to the same epitope as one or more antibodies selected from the group consisting of 104, clone 30F11, clone ACK2, clone 2B8, clone 3C11, clone MEM-28, clone HI130, clone 581 and clone 4H11.

In certain aspects the antibody is selected from the group consisting of clone L243, clone TS2/4, clone TS1/18, clone 581, clone 4H11, clone A2A9/6, clone CD43-10G7, clone BHPT-1, clone orb12060, clone 2D1, clone CC2C6, clone TS2/9, clone CY1G4, clone OKT9, clone CD84.1.21, clone VIM3b, clone A3C6E2, clone EMK08, clone TMP4, clone KPL-1, clone 3a6, clone HD83 and clone MEM-216. In certain embodiments, the agent is an antibody comprising a complementarity determining region that is the same as the complementarity determining region for one or more antibodies selected from the group consisting of L243, clone TS2/4, clone TS1/18, clone 581, clone 4H11, clone A2A9/6, clone CD43-10G7, clone BHPT-1, clone orb12060, clone 2D1, clone CC2C6, clone TS2/9, clone CY1G4, clone OKT9, clone CD84.1.21, clone VIM3b, clone A3C6E2, clone EMK08, clone TMP4, clone KPL-1, clone 3a6, clone HD83 and clone MEM-216. In certain embodiments, the agent is an antibody that binds to the same epitope as one or more antibodies selected from the group consisting of L243, clone TS2/4, clone TS1/18, clone 581, clone 4H11, clone A2A9/6, clone CD43-10G7, clone BHPT-1, clone orb12060, clone 2D1, clone CC2C6, clone TS2/9, clone CY1G4, clone OKT9, clone CD84.1.21, clone VIM3b, clone A3C6E2, clone EMK08, clone TMP4, clone KPL-1, clone 3a6, clone HD83 and clone MEM-216. Furthermore, it is understood that the methods described herein which utilize antibodies as the agent to facilitate delivery of the immunotoxin to the cells of the target tissue can also utilize functional fragments (e.g., antigen-binding fragments) of such antibodies.

Antibodies of the present invention can be raised against an appropriate marker or antigen, such as, for example, isolated and/or recombinant mammalian CD34, CD45, or CD117: cKit/SCF receptor or portions or epitopes thereof. Antibodies can be raised against a selected marker (e.g., a cell surface marker) or antigen by methods known to those skilled in the art. Such methods for raising polyclonal antibodies are well known in the art and are described in detail, for example, in Harlow et al., 1988 in: Antibodies, A Laboratory Manual, Cold Spring Harbor, N.Y.

Typically, such antibodies are raised by immunizing an animal (e.g. a rabbit, rat, mouse, donkey, etc.) by multiple subcutaneous or intraperitoneal injections of the relevant antigen (e.g., CD34, CD45, or CD117: cKit/SCF receptor) optionally conjugated to keyhole limpet hemocyanin (KLH), serum albumin, other immunogenic carrier, diluted in sterile saline and combined with an adjuvant (e.g. Complete or Incomplete Freund's Adjuvant) to form a stable emulsion. The polyclonal antibody is then recovered from blood or ascites of the immunized animal. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc. Polyclonal antiserum can also be rendered monospecific using standard procedures (see, e.g., Agaton et al., "Selective Enrichment of Monospecific Polyclonal Antibodies for Antibody-Based Proteomics Efforts," *J Chromatography A* 1043(1):33-40 (2004), which is hereby incorporated by reference in its entirety).

In some embodiments, monoclonal antibodies can be prepared using hybridoma methods, such as those described by Kohler and Milstein, "Continuous Cultures of Fused Cells Secreting Antibody of Predefined Specificity," *Nature* 256:495-7 (1975), which is hereby incorporated by reference in its entirety. Using the hybridoma method, a mouse, hamster, or other appropriate host animal, is immunized to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against for example, a cell surface marker such as CD34, CD45, or CD117: cKit/SCF receptor, as determined by immunoprecipitation, immunoblotting, or by an in vitro binding assay such as radioimmunoassay (RIA) or enzyme-linked immunosorbent assay (ELISA) can then be propagated either in vitro culture using standard methods (James Goding, Monoclonal Antibodies: Principles and Practice (1986) which is hereby incorporated by reference in its entirety) or in vivo as ascites tumors in an animal. The monoclonal antibodies can then be purified from the culture medium or ascites fluid as described for polyclonal antibodies above.

In some embodiments, monoclonal antibodies can be made using recombinant DNA methods as described in U.S. Pat. No. 4,816,567 to Cabilly et al., which is hereby incorporated by reference in its entirety. The polynucleotides encoding a monoclonal antibody are isolated, such as from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, and monoclonal antibodies are generated by the host cells. Recombinant monoclonal antibodies or fragments thereof of the desired species can also be isolated from phage display libraries as described (McCafferty et al., "Phage Antibodies: Filamentous Phage Displaying Antibody Variable Domains," Nature 348:552-554 (1990); Clackson et al., "Making Antibody Fragments using Phage Display Libraries," Nature 352:624-628 (1991); and Marks et al., "By-Passing Immunization. Human Antibodies from V-Gene Libraries Displayed on Phage," J. Mol. Biol. 222: 581-597 (1991), which are hereby incorporated by reference in their entirety).

The polynucleotides encoding a monoclonal antibody can further be modified in a number of different ways using recombinant DNA technology to generate alternative antibodies. In one embodiment, the constant domains of the light and heavy chains of, for example, a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

In some embodiments, the monoclonal antibody against a cell surface marker or antigen, such as CD34, CD45, or CD117: cKit/SCF receptor, is a humanized antibody. In certain embodiments, the monoclonal antibody against a cell surface marker or antigen, such as HLA-DR, CD11a, CD18, CD34, CD41/61, CD43, CD45, CD47, CD58, CD71, CD84, CD97, CD117, CD133, CD162, CD166, CD205 and/or CD361, is a humanized antibody. Humanized antibodies are antibodies that contain minimal sequences from non-human (e.g. murine) antibodies within the variable regions. Such antibodies are used therapeutically to reduce antigenicity and human anti-mouse antibody responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the complementarity determining region (CDR) of a human antibody with that of a non-human antibody (e.g. mouse, rat, rabbit, hamster, etc.) having the desired specificity, affinity, and capability (Jones et al., "Replacing the Complementarity-Determining Regions in a Human Antibody With Those From a Mouse," Nature 321: 522-525 (1986); Riechmann et al., "Reshaping Human Antibodies for Therapy," Nature 332:323-327 (1988); Verhoeyen et al., "Reshaping Human Antibodies: Grafting an Antilysozyme Activity," Science 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produces an antibody directed against a target antigen can be generated (see, e.g. Reisfeld et al., Monoclonal Antibodies and Cancer Therapy 77 (Alan R. Liss 1985) and U.S. Pat. No. 5,750,373 to Garrard, which are hereby incorporated by reference in their entirety). Also, the human antibody can be selected from a phage library, where that phage library expresses human antibodies (Vaughan et al., "Human Antibodies with Sub-Nanomolar Affinities Isolated from a Large Non-immunized Phage Display Library," Nature Biotechnology, 14:309-314 (1996); Sheets et al., "Efficient Construction of a Large Nonimmune Phage Antibody Library: The Production of High-Affinity Human Single-Chain Antibodies to Protein Antigens," Proc Nat'l Acad Sci USA 95:6157-6162 (1998); Hoogenboom et al., "By-passing Immunisation. Human Antibodies From Synthetic Repertoires of Germline VH Gene Segments Rearranged In Vitro," J Mol. Biol, 227:381-8 (1992); Marks et al., "By-passing Immunization. Human Antibodies from V-gene Libraries Displayed on Phage," J. Mol. Biol, 222: 581-97 (1991), which are hereby incorporated by reference in their entirety). Humanized antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety.

In some embodiments, the agents that comprise the immunotoxin compositions of the present invention include bispecific antibodies that specifically recognize one or more cell surface markers. Bispecific antibodies are antibodies that are capable of specifically recognizing and binding at least two different epitopes. Bispecific antibodies can be intact antibodies or antibody fragments. Techniques for making bispecific antibodies are common in the art (Brennan et al., "Preparation of Bispecific Antibodies by Chemical Recombination of Monoclonal Immunoglobulin G1 Fragments," Science 229:81-3 (1985); Suresh et al., "Bispecific Monoclonal Antibodies From Hybrid Hybridomas," Methods in Enzymol. 121:210-28 (1986); Traunecker et al., "Bispecific Single Chain Molecules (Janusins) Target Cytotoxic Lymphocytes on HIV Infected Cells," EMBO J. 10:3655-3659 (1991); Shalaby et al., "Development of Humanized Bispecific Antibodies Reactive with Cytotoxic Lymphocytes and Tumor Cells Overexpressing the HER2 Protooncogene," J. Exp. Med. 175:217-225 (1992); Kostelny et al., "Formation of a Bispecific Antibody by the Use of Leucine Zippers," J. Immunol. 148: 1547-1553 (1992); Gruber et al., "Efficient Tumor Cell Lysis Mediated by a Bispecific Single Chain Antibody Expressed in *Escherichia coli*," J. Immunol. 152:5368-74 (1994); and U.S. Pat. No. 5,731,168 to Carter et al., which are hereby incorporated by reference in their entirety).

In some embodiments, the use of such bispecific antibodies may facilitate the targeting of the immunotoxin compositions disclosed herein to a first cell surface marker expressed by cells of the target tissues, as well as a second marker capable of facilitating the internalization of such immunotoxin composition. Similarly, such bispecific antibodies may be used to increase the targeting precision of the immunotoxin compositions disclosed herein. In some aspects, bispecific antibodies may be useful for binding a cell surface marker of a particular cell (e.g., myeloid cells), while a second cell surface marker may also be targeted to internalize the immunotoxin composition. For example, in certain embodiments, the bispecific antibodies disclosed herein bind a cell surface marker having internalizing properties that may be exploited to facilitate the intracellular delivery of a toxin (e.g., a toxin such as saporin) to the cells of a target tissue and thereby induce cell death.

Bispecific antibodies that bind, for example, both CD34 and CD45, may be prepared by any technique known in the art. For example, in certain aspects the bispecific antibodies disclosed herein may be prepared using chemical linkage. Alternatively, such bispecific antibodies can be prepared recombinantly using a co-expression of two immunoglobulin heavy chain/light chain pairs. In some aspects, bispecific antibodies may be prepared by disulfide exchange, production of hybrid-hybridomas, by transcription and translation to produce a single polypeptide chain embodying a bispecific antibody, or transcription and translation to produce more than one polypeptide chain that can associate covalently to produce a bispecific antibody.

In some embodiments, the bispecific agents or antibodies disclosed herein binds to one or more markers selected from the group consisting of CD13, CD33, CD34, CD44, CD45, CD49d: VLA-4, CD49f: VLA-6, CD59, CD84: CD150 family, CD90: Thy1, CD93, CD105: Endoglin, CD117: cKit/SCF receptor, CD123: IL-3R, CD126: IL-6R, CD133, CD135: Flt3 receptor, CD166: ALCAM, CD184: CXCR4, Prominin 2, Erythropoietin R, Endothelial Cell-Selective Adhesion Molecule, CD244, Tie1, Tie2, MPL, G-CSFR or CSF3R, IL-1R, gp130, Leukemia inhibitory factor Receptor, oncostatin M receptor, Embigin and IL-18R. In certain embodiments, the bispecific agent or antibody disclosed herein binds to one or more markers selected from the group consisting of HLA-DR, CD11a, CD18, CD34, CD41/61, CD43, CD45, CD47, CD58, CD71, CD84, CD97, CD117, CD133, CD162, CD166, CD205 and CD361.

In some embodiments, the bispecific agents or antibodies disclosed herein bind to two or more markers selected from the group consisting of CD13, CD33, CD34, CD44, CD45, CD49d: VLA-4, CD49f: VLA-6, CD59, CD84: CD150 family, CD90: Thy1, CD93, CD105: Endoglin, CD117: cKit/SCF receptor, CD123: IL-3R, CD126: IL-6R, CD133, CD135: Flt3 receptor, CD166: ALCAM, CD184: CXCR4, Prominin 2, Erythropoietin R, Endothelial Cell-Selective Adhesion Molecule, CD244, Tie1, Tie2, MPL, G-CSFR or CSF3R, IL-1R, gp130, Leukemia inhibitory factor Receptor, oncostatin M receptor, Embigin and IL-18R. In certain embodiments, the bispecific agent or antibody disclosed herein binds to two or more markers selected from the group consisting of HLA-DR, CD11a, CD18, CD34, CD41/61, CD43, CD45, CD47, CD58, CD71, CD84, CD97, CD117, CD133, CD162, CD166, CD205 and CD361.

In certain embodiments, the bispecific agent or antibody disclosed herein binds to two or more markers expressed on human hematopoietic stem cells and selected from the group consisting of CD7, CDw12, CD13, CD15, CD19, CD21, CD22, CD29, CD30, CD33, CD34, CD36, CD38, CD40, CD41, CD42a, CD42b, CD42c, CD42d, CD43, CD45, CD45RA, CD45RB, CD45RC, CD45RO, CD48, CD49b, CD49d, CD49e, CD49f, CD50, CD53, CD55, CD64a, CD68, CD71, CD72, CD73, CD81, CD82, CD85A, CD85K, CD90, CD99, CD104, CD105, CD109, CD110, CD111, CD112, CD114, CD115, CD117, CD123, CD124, CD126, CD127, CD130, CD131, CD133, CD135, CD138, CD151, CD157, CD162, CD164, CD168, CD172a, CD173, CD174, CD175, CD175s, CD176, CD183, CD191, CD200, CD201, CD205, CD217, CD220, CD221, CD222, CD223, CD224, CD225, CD226, CD227, CD228, CD229, CD230, CD235a, CD235b, CD236, CD236R, CD238, CD240, CD242, CD243, CD277, CD292, CDw293, CD295, CD298, CD309, CD318, CD324, CD325, CD338, CD344, CD349, and CD350.

In certain embodiments, the bispecific agent or antibody disclosed herein binds to two or more markers expressed on human hematopoietic stem cells and selected from the group consisting of CD11a, CD18, CD37, CD47, CD52, CD58, CD62L, CD69, CD74, CD97, CD103, CD132, CD156a, CD179a, CD179b, CD184, CD232, CD244, CD252, CD302, CD305, CD317, and CD361.

In some embodiments, the bispecific antibodies disclosed herein binds to CD34 and CD117: cKit/SCF receptor. In some embodiments, the bispecific antibodies disclosed herein binds to CD45 and CD117: cKit/SCF receptor. In some embodiments, the bispecific antibodies disclosed herein binds to CD34 and CD45.

In certain embodiments, it may be desirable to use an antibody fragment, rather than an intact antibody. Various techniques are known for the production of antibody fragments. Traditionally, these fragments are derived via proteolytic digestion of intact antibodies (e.g. Morimoto et al., "Single-step Purification of F(ab')2 Fragments of Mouse Monoclonal Antibodies (immunoglobulins G1) by Hydrophobic Interaction High Performance Liquid Chromatography Using TSKgel Phenyl-5PW," Journal of Biochemical and Biophysical Methods 24:107-117 (1992) and Brennan et al., "Preparation of Bispecific Antibodies by Chemical Recombination of Monoclonal Immunoglobulin G1 Fragments," Science 229:81-3 (1985), which are hereby incorporated by reference in their entirety). However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870 to Rinderknecht et al., which is hereby incorporated by reference, and can be monospecific or bispecific. Other techniques for the production of antibody fragments will be apparent to the skilled practitioner.

The present invention further encompasses variants and equivalents which are substantially homologous to the chimeric, humanized and human antibodies, or antibody fragments thereof. These can contain, for example, conservative substitution mutations, (e.g., the substitution of one or more amino acids by similar amino acids, which maintain or improve the binding activity of the antibody or antibody fragment).

In a preferred embodiment, cells which express the marker can be used as an immunogen or in a screen for antibody which binds the marker. In one embodiment, the antibody has specificity for the marker, epitope or a portion thereof. In those embodiments where the agent is or comprises an antibody, upon identifying and selecting a marker that is expressed on the surface of the cells of the target tissue (e.g., CD45, CD117 or portions or epitopes thereof), an antibody may be raised against such marker using art-recognized techniques and methods.

In certain aspects, the agent is or comprises a ligand. For example, in certain embodiments the agent is or comprises a ligand, such as stem cell factor, and that interacts or binds to a cell surface receptor, such as CD117.

In certain embodiments, the agent is used to deliver, or to facilitate the delivery of a toxin to the cells of a target tissue and, following the delivery of such toxin to the cells of the target tissue, such toxin is internalized by such cells and thereby exerts a cytotoxic effect on such cells of the target tissue. In certain embodiments, the agent is used to deliver, or to facilitate the delivery of a pore-forming moiety, such as the mutant protective antigen (mut-PA) to the cells of the target tissue. In certain embodiments, upon delivery of an agent coupled to a toxin (e.g., CD117-SAP) to the cells of a target tissue, both the agent and toxin are co-localized to an intracellular compartment of one or more cells of the target tissue, thereby ablating or depleting such cells.

In certain embodiments, the compositions and methods disclosed herein may be administered or otherwise practiced alone or in combination with other available therapies. For example, the methods, conjugates and compositions disclosed herein may be administered to a subject as a primary therapy or as an adjunct therapy.

In certain embodiments, the methods and compositions disclosed herein are practiced or administered in combination with (e.g., co-administered with) one or more mobilizing agents that are capable of inducing the migration of, for example, hematopoietic stem cells and/or progenitor cells from a first compartment (e.g., a target tissue, such as the stem cell niche or the bone marrow compartment) into a second compartment (e.g., the peripheral blood or an organ, such as the spleen), as described in International Publication No. WO2014/134539, the contents of which are incorporated herein by reference in their entirety. In such embodiments, the subject may undergo mobilization therapy, and the agents disclosed herein may be co-administered or subsequently administered to the subject such that the mobilized cells contact the administered composition in the compartment into which such cells were mobilized (e.g., in the peripheral compartment).

In certain aspects, the co-administration of the compositions disclosed herein with one or more mobilizing agents provides a means of increasing or enhancing the activity and/or efficacy of such compositions by increasing the likelihood that the compositions contact, for example, hematopoietic stem cells and/or progenitor cells that have been mobilized into a peripheral compartment. Exemplary, mobilizing agents include, for example one or more of a CXCR2 agonists (e.g., Gro-beta or Gro-betaΔ4) and a CXCR4 antagonist (e.g., Plerixafor or Mozobil®). In certain aspects, the mobilizing agent comprises, G-CSF alone, or in combination with Plerixafor. In certain aspects, the mobilizing agent comprises at least one heparan sulfate inhibitor. In certain aspects, the mobilizing agent is or comprises filgrastim (GCSF).

In certain embodiments, the cytotoxicity of the methods, compositions and toxins disclosed herein are internalization dependent and thus require the translocation of the toxin into an intracellular compartment of the cells of the target tissue. Such internalization dependent toxicity is distinguishable from previous approaches of targeting using an anti-CD45 radioimmunotoxin (RIT). In particular, by causing such a CD45-RIT to bind specifically to hematopoietic cells, death is not internalization dependent, but rather occurs in nearby cells exposed to irradiation, including undesired irradiation to the spleen and liver. In contrast, the compositions and methods disclosed herein enable CD45 receptor internalization-mediated death using, for example an anti-CD45-SAP immunotoxin (see, for example, FIGS. 4A-4C and FIGS. 5A-5E illustrating the cell killing activity of a CD45-SAP immunotoxin in vitro and in vivo and confirming that by targeting CD45, the immunotoxins disclosed herein may be internalized). In some embodiments, the methods and compositions disclosed herein do not induce cell death through DNA-damage.

As used herein the terms "internalized" and "internalization" generally mean that the agent and/or toxin are introduced into or otherwise reach the intracellular compartment of one or more cells (e.g., HSCs or progenitor cells) of the target tissue (e.g., bone marrow). For example, an agent and/or toxin may reach the intracellular compartment of a cell via a receptor-mediated process (e.g., an endocytic process) in which the cell will only take in an extracellular agent and/or toxin upon binding to a specific receptor. In certain aspects, the agents and/or toxins disclosed herein are internalized by the endogenous stem cell (e.g., HSCs) or progenitor cell population at a rate of at least about 10%, at least about 15%, at least about 20%, at least about 25%, at least about 30%, at least about 40%, at least about 50%, at least about 60%, at least about 70%, at least about 80%, at least about 90%, at least about 95%, or least about 99%.

In certain aspects, the compositions disclosed herein (e.g., antibody-toxin conjugates) are internalized by a cell expressing a marker (e.g., a CD34, CD45 or CD117 cell surface marker) upon binding of such agent (e.g., an antibody) to an epitope of the marker (e.g., CD34, CD45 or CD117).

In certain embodiments, the compositions and methods disclosed herein induce cytotoxicity or cell death upon internalization of a toxin or an immunotoxin by a targeted cell (e.g., a hematopoietic stem cell). As used herein, the term "toxin" is used generally to refer to any chemical or biological compound, composition or moiety that can induce a cytotoxic or deleterious effect on a targeted cell. In certain embodiments, the cytotoxic or deleterious effects that are induced by the toxin or immunotoxin occur following its internalization into an intracellular compartment of a cell (e.g., a CD45+ or CD117+ cell). For example, in certain aspects, upon internalization of the agent coupled to the toxin, the toxin is cleaved from the agent (e.g., the toxin and agent are uncoupled) and the toxin inhibits protein synthesis, thereby causing cellular death. Similarly, in certain aspects, upon internalization of the agent coupled to the toxin, the toxin is cleaved from the agent (e.g., the toxin and agent are uncoupled) and the toxin inhibits ribosomal activity, thereby causing cellular death.

Preferably, the toxin must gain cellular entry or otherwise be internalized to exert its cytotoxic or deleterious effect. Accordingly, preferred are toxins that only exert a cytotoxic or deleterious effect following their internalization by one or more cells of the target tissue. Saporin, a catalytic N-glycosidase ribosome-inactivating protein (RIP) that halts protein synthesis, represents an exemplary toxin for use in accordance with the methods and compositions disclosed herein. Unlike other ricin family members, saporin lacks a general cell entry domain and is non-toxic unless coupled to a targeting antibody or ligand (e.g., the 2B8 clone) that is capable of receptor-mediated internalization. This is illustrated in FIG. 2A, which demonstrates that the co-administration of an antibody plus saporin failed to result in a depletion of hematopoietic stem cells due to the inability of such saporin to gain cellular entry. In contrast, as also illustrated in FIG. 2A, when a saporin toxin was coupled to an anti-CD45 antibody, that CD45-SAP conjugate demonstrated 98% depletion of hematopoietic stem cells in bone marrow harvested 8 days post-conditioning. In certain aspects the toxin is coupled to an agent (e.g., a humanized antibody) to facilitate the targeted delivery of such toxin to one or more target cells (e.g., CD45+ and/or CD117+ cells).

In certain aspects, the toxin is a protein-based toxin, and may include, for example, modified ricin and Ricin A chain derivatives (e.g., Ricin A chain, deglycosylated Ricin A chain), saporin, diphtheria toxin, pseudomonas toxins and variants (e.g. PE38 and others) and small molecule toxins. A toxin can be a protein-based toxin including, for example, biologically-active toxins of bacterial, fungal, plant or animal origin and fragments thereof. In some embodiments, the toxin may be recombinantly-prepared. In certain aspects, a toxin may be a synthetic toxin.

While certain embodiments disclosed herein relate to the use of saporin as the selected toxin, it should be understood that the inventions disclosed herein are not limited to saporin or to protein-based toxins. Rather, several alternative toxins may be used in accordance with the teachings of the present inventions. For example, diphtheria toxin (DT) and pseudomonas exotoxin A (PE) both halt protein synthesis at the elongation step. Ricin family toxins (e.g. saporin) have N-glycosidase activity resulting in the depurination of a critical adenine in the 28S ribosomal RNA (rRNA). All of these toxins inhibit protein synthesis and have the common property of being effective against dividing and non-dividing cells if internalized; this is in contrast to antibody-drug conjugates (ADCs), in which the drugs specifically affect dividing cells by covalently modifying DNA or disrupting microtubule dynamics. As hematopoietic stem cells are normally in a non-proliferating quiescent state, the use of protein toxins capable of inducing cell death regardless of cell-cycle status is preferred for effective hematopoietic stem cell depletion and conditioning. In certain embodiments, the toxin is selected from the group of toxins consisting of saporin, diphtheria toxin, pseudomonas exotoxin A, modified ricin analogs and Ricin A chain derivatives, small molecule toxins and combinations thereof. In certain aspects, the toxin is a modified ricin analogs or Ricin A chain derivatives, for example the ricin A chain. In certain aspects, the toxin (e.g., the ricin A chain) has been modified, for example, to delete a cellular entry domain.

In certain aspects, the toxin is selected from the group of toxins consisting of abrin toxin, modeccin toxin, gelonin toxin, momordin toxin, trichosanthin toxin, luffin toxin and combinations thereof.

While in certain aspects, the toxin may be a protein-based toxin, it should be understood that the contemplated toxins are not limited to protein-based toxins. Rather, contemplated toxins for use in accordance with any aspects of the present inventions broadly include any compounds or agents (e.g., cytotoxic compounds or agents) that selectively result in the death of one or more cells in the target tissue (e.g., the bone marrow stem cell niche) or that otherwise decrease cell viability. In various embodiments of any aspect of the present inventions, the toxins useful in accordance with the compositions and methods of the present invention comprise one or more DNA-damaging molecules. For example, the selected toxin may comprise one or more anti-tubulin agents (e.g. maytansines) or tubulin inhibitors, DNA crosslinking agents, DNA alkylating agents and cell cycle or mitotic disrupters. In certain aspects, the selected toxin is or comprises a mitotic disruptor or inhibitor, such as maytansine or a functional fragment, derivative or analog thereof.

In certain embodiments, the toxin (e.g., a toxin of fungal origin) inhibits RNA polymerase II and/or III (e.g., an inhibitor of mammalian RNA polymerase II and/or III). In certain aspects such an RNA polymerase II inhibitor toxin is or comprises one or more amatoxins or a functional fragment, derivative or analog thereof. Amatoxins are potent and selective inhibitors of RNA polymerase II, and include all cyclic peptides composed of eight amino acids as isolated from the genus *Amanita*, most notably *Amanita phalloides*. Such amatoxins may be isolated from a variety of mushroom species (e.g., *Amanita phalloides, Galerina marginata* and *Lepiota brunneo-incarnata*) or in certain aspects may be prepared synthetically. Exemplary toxins suitable for use in accordance with any of the methods or compositions disclosed herein may include or comprise one or more amatoxins selected from the group consisting of α-amanitin, β-amanitin, γ-amanitin, £-amanitin, amanin, amaninamide, amanullin, amanullinic acid and any functional derivatives or analogs thereof. In certain embodiments, the toxin is or comprises α-amanitin, which is an inhibitor of RNA polymerase II and III, or a functional fragment, derivative or analog thereof.

In certain embodiments, the toxin is a small molecule toxin. Such small molecule toxins may be coupled to an agent (e.g., a monoclonal antibody) to form an antibody-drug conjugate (ADC) that may be used, for example, to condition a subject's tissues for engraftment. In certain embodiments, the toxin is derived from bacteria. In some embodiments, the toxin is derived from an insect. In some embodiments, the toxin comprises or is derived from a virus. In some embodiments, the toxin is derived from a plant or a fungus. In some embodiments, the toxin is a naturally-occurring toxin or a fragment thereof. In some embodiments, such a naturally-occurring toxin may be modified relative to its naturally-occurring counterpart, for example, to remove any domains or regions that would facilitate cellular entry or to substitute one or more amino acids.

In certain embodiments, the toxin may be directly coupled or otherwise bound to an agent (e.g., an antibody that specifically or selectively binds CD34, CD45 or CD117). For example, the agent is directly coupled to one or more toxins (e.g., as a chimeric fusion protein). As used herein, the terms "couple" and "coupling" broadly refer to any physical, biological or chemical linking or joining of two or more moieties or components together. Such a coupling may be direct or indirect. For example, disclosed herein are agents (e.g., bispecific agents) that may be directly or indirectly coupled to toxins. Similarly, also disclosed are mutant protective antigens (mut-PA) that may be coupled to an agent. Also disclosed is a factor (e.g., lethal factor N-terminus (LFN) and/or edema factor N-terminus (EFN)) that may be coupled to a toxin. In certain embodiments, the factor is or comprises an enzymatic factor.

In certain aspects, the term coupling refers to a functional coupling. For example, contemplated herein are any couplings of two or more moieties that functions to facilitate the co-delivery of such coupled moieties intracellularly. In certain aspects, such a coupling may be direct coupling or an indirect coupling. In certain embodiments, such a coupling may be permanent or temporary. For example, in certain aspects, upon internalization of an agent (e.g., a bispecific agent) coupled to a toxin, the coupling is cleaved, thereby releasing the toxin intracellularly and exerting a cytotoxic effect on the cell.

The agents and the toxin are covalently or non-covalently coupled or linked to each other. Such a coupling may be direct or indirect. For example, a toxin selected from the group of toxins consisting of saporin, diphtheria toxin, pseudomonas exotoxin A, modified ricin analogs and combinations thereof may be directly or indirectly coupled to an antibody that selectively binds CD45 to form an immunotoxin. In some embodiments, the toxins disclosed herein may be indirectly coupled to an antibody, as illustrated for example, in FIG. 1. As illustrated in FIG. 1, such antibodies may be biotinylated and coupled to a streptavidin-toxin moiety. Alternatively, in certain embodiments, the toxin may be biotinylated, which may be indirectly coupled to an anti-CD34, anti-CD45 or anti-CD117 antibody that may be bound to or labeled with one or more of streptavidin, avidin, neutravidin and any other variants thereof. In certain aspects, the antibodies disclosed herein are humanized.

In certain aspects, the ratio of agent (e.g., antibody):toxin is about 0.1:1, about 0.25:1, about 0.5:1, about 1:1, about 2:1, about 3:1, about 4:1, about 5:1, about 6:1, about 7:1, about 8:1, about 9:1 or about 10:1. In any of the foregoing embodiments, such ratios are expressed as a ratio of a streptavidin tetramer-toxin chemical conjugate (e.g., a streptavidin tetramer-saporin chemical conjugate). For example, such a streptavidin tetramer may comprise an average of 2.8 toxin (e.g., saporin) molecules and may be expressed as a 1:1 ratio of agent to tetramer-toxin, or alternatively as a 1:2.8 ratio of agent to toxin. In certain embodiments, the ratio of agent (e.g., antibody) to toxin is about 1:2, about 1:2.5, about 1:2.8, about 1:3, about, about 1:3.5, about 1:4, about 1:4.5, about 1:5, about 1:6, about 1:7, about 1:8, about 1:9 or about 1:10. Also contemplated are chimeras, where an antibody and toxin are expressed recombinantly as a single protein. Also contemplated are regions or fragments of antibodies, for example, scFv-toxin conjugate, scFv-toxin chimeras, scFv-toxin multivalent forms that may promote internalization by CD45 receptor cross-linking (e.g., diabodies, tandem di-scFv, tandem tri-scFv, triabodies and/or tetrabodies). Also contemplated are antibody drug conjugates (e.g., CD45-ADCs), which may also be useful for hematological malignancies as an alternative to transplant and, based on the present disclosures concerning the internalizing activity of a cell surface marker (e.g., the CD45 receptor). In certain embodiments, such agents or antibodies are bispecific and bind two cell surface markers.

In certain embodiments, the inventions disclosed herein relate to internalizing (antibody fragment) Fab-toxin conjugates. In certain embodiments, the inventions disclosed herein relate to internalizing (single chain fragment) scFv-toxin conjugates. In certain embodiments, the inventions disclosed herein relate to diabody: non-covalent dimer of single-chain Fv (scFv): targeting one or multiple receptors. In certain embodiments, the inventions disclosed herein relate to bivalent (or bispecific) (scFv)$_2$. In certain embodiments, the inventions disclosed herein relate to tandem scFv. Also contemplated are internalizing aptamer-toxin conjugates and internalizing ligand-toxin conjugates, or any chimeric or non-covalent combination of the above (e.g. scFv-ligand-toxin), as well as all non-covalent formulations (e.g., biotin-streptavidin and including the streptavidin analogs neutravidin and avidin), and chimeric molecules that may be created by recombinant expression of fusion proteins, native chemical ligation, enzyme catalyzed conjugation (e.g. sortase and others) or other conjugation methods (e.g., click chemistry using unnatural amino acids, NHS-ester agents to modify lysines, maleimide agents to modify cysteine, disulfide bridges). Also contemplated is the incorporation of peptide sequences (e.g., natural, unnatural and cyclic peptides) that facilitate internalization (e.g., HIV-TAT, penetratin, RGD peptide, poly arginine and variants) of the agents and/or toxins disclosed herein.

The methods disclosed herein are not limited to receptor-mediated internalization of a toxin, but rather contemplate any available means of selectively delivering a toxin to an intracellular compartment of the cells of a target tissue. For example, in certain embodiments, disclosed herein are methods of delivering toxins intracellularly using pore-mediated internalization.

Disclosed herein are methods of conditioning a subject for engraftment or methods of selectively depleting or ablating an endogenous stem cell population in a target tissue (e.g., bone marrow tissue) of the subject by administering to the subject an effective amount of a pore-forming chimera comprising a mutant protective antigen (mut-PA) coupled to an agent (e.g., a ligand such as stem cell factor). Protective antigen (PA) is secreted by Bacillus anthracis as water-soluble precursor form PA83 (83 kDa) that undergoes proteolytic activation by furin-type proteases to cleave a 20 kDa fragment off the N-terminus and thereby form the activated PA monomer is able to form pre-pore heptamers. Such a pore-forming chimera forms one or more pores in the cell membrane of the endogenous stem cell population and thereby facilitates the delivery of a subsequently-administered or co-administered toxin to such stem cell population. For example, an effective amount of a second chimera comprising a factor (e.g., an enzymatic factor such as lethal factor N-terminus and/or edema factor N-terminus, or fragments thereof) coupled to a toxin may be administered to the subject, following which the toxin is internalized by the endogenous stem cell population, thereby selectively depleting or ablating the endogenous stem cell population in the target tissue and conditioning the subject for engraftment. In certain embodiments, the factor is lethal factor N-terminus (LFN), or a fragment thereof. In certain embodiments, the factor is edema factor N-terminus (EFN), or a fragment thereof. Both lethal factor (LF) and edema factor (EF) need the binding component protective antigen (PA) for delivery into the cytosol of the cells, where they exhibit enzymatic activities. The 63 kDa C-terminal part of PA forms heptameric channels that inserts in endosomal membranes at low pH, necessary to translocate EF and LF into the cytosol of target cells.

In certain embodiments, a pore-forming moiety, such as the mutant protective antigen (mut-PA), is coupled to an agent that is useful for selectively targeting or directing such pore-forming moiety to the cells of the target tissues (e.g., hematopoietic stem cells or progenitor cells) (Janowiak, B. E., et al., *Protein Sci.* 18(2): 348-358 (2009); Mourez M. et al., *PNAS* 100(24): 13803-08 (2003); Ming, Y & R Collier, *J. Mol Med.* 9(1-2): 46-51 (2003); Rogers M. S., et al., *Cancer Res.* 15; 67(20):9980-5 (2007)). For example, mutant protective antigens (mut-PA) may be coupled or otherwise fused to agents (e.g., ligands or scFv) to create chimeras that enable the cell-specific forming of cell surface pores. Similarly, in certain embodiments, mutant protective antigens (mut-PA) may be coupled or otherwise fused to a bispecific agent (e.g., a bispecific antibody) to create chimeras that enable the cell-specific forming of cell surface pores. Such cell surface pores may in turn be used or exploited to import or internalize an administered (e.g., co-administered or subsequently-administered) lethal factor N-terminus-toxin chimera (LFN-toxin) and thereby ablate or deplete the cells of the target tissue.

Figure 27:
FIG. 27 depicts the results of a pilot enhanced HSC engraftment study. As illustrated, ACK2-SAP is better than ACK2 only, but 2B8-SAP is considerably more efficient than either, and comparable to CD45-SAP.

Accordingly, in certain embodiments of the present inventions, the selected toxin may comprise one or more lethal factors coupled (e.g., functionally coupled) to the toxin (e.g., LFN-SAP). Various toxins can be coupled to LFN, including diptheria toxin and/or saporin toxin (e.g., LFN-DTA, LFN-SAP, etc.) The internalization mechanism is intrinsic to PA and LFN and is generally depicted in FIG. 27. In contrast to certain embodiments disclosed herein, the foregoing embodiments advantageously do not require an internalizing marker, receptor or internalizing properties of antibody/ligand, but rather rely on the interaction of PA and LFN to facilitate the delivery of the toxin intracellularly. In some embodiments, the agent is selected from the group consisting of a scfv, a Fab, a discFv, a biscFv, a tri-scfv, a tandem scfv, an aptamer, an antibody and a ligand.

The methods and compositions disclosed herein may be used to condition any number of target tissues of a subject, including, for example bone marrow tissue. As used herein, the term "target tissue" generally refers to any tissues of a subject to which the compositions and methods disclosed herein may be selectively targeted. In certain embodiments, such target tissues comprise an endogenous population of HSCs or progenitor cells (e.g., the stem cell niche of the bone marrow tissue). In certain embodiments, the target tissue is or comprises a subject's bone marrow tissue.

In certain aspects, the compositions and methods of the present inventions are useful for non-myeloablative conditioning in a subject, for example, bone marrow conditioning in advance of hematopoietic stem cell or progenitor cell transplantation. By selectively targeting a marker (e.g., a CD45 cell surface marker) with a toxin (e.g., saporin) that requires cellular entry to exert its cytotoxic effect, the present inventions minimize the incidence and severity of adverse effects. For example, the incidence and severity of adverse effects commonly associated with traditional conditioning regimens, such as mucositis, which may be minimized or in certain instances eliminated. Similarly, the present inventors have demonstrated that conditioning a subject using the methods and compositions (e.g., CD45-SAP immunotoxins) disclosed herein minimizes the incidence of life-threatening thrombocytopenia, neutropenia and red blood cell loss, all of which are commonly associated with traditional conditioning methods, which often require both irradiation and cytotoxic drugs. Accordingly, in certain aspects the compositions and methods disclosed herein are characterized as being non-myeloablative.

Figures 3A, 3B, 3C, 3D:
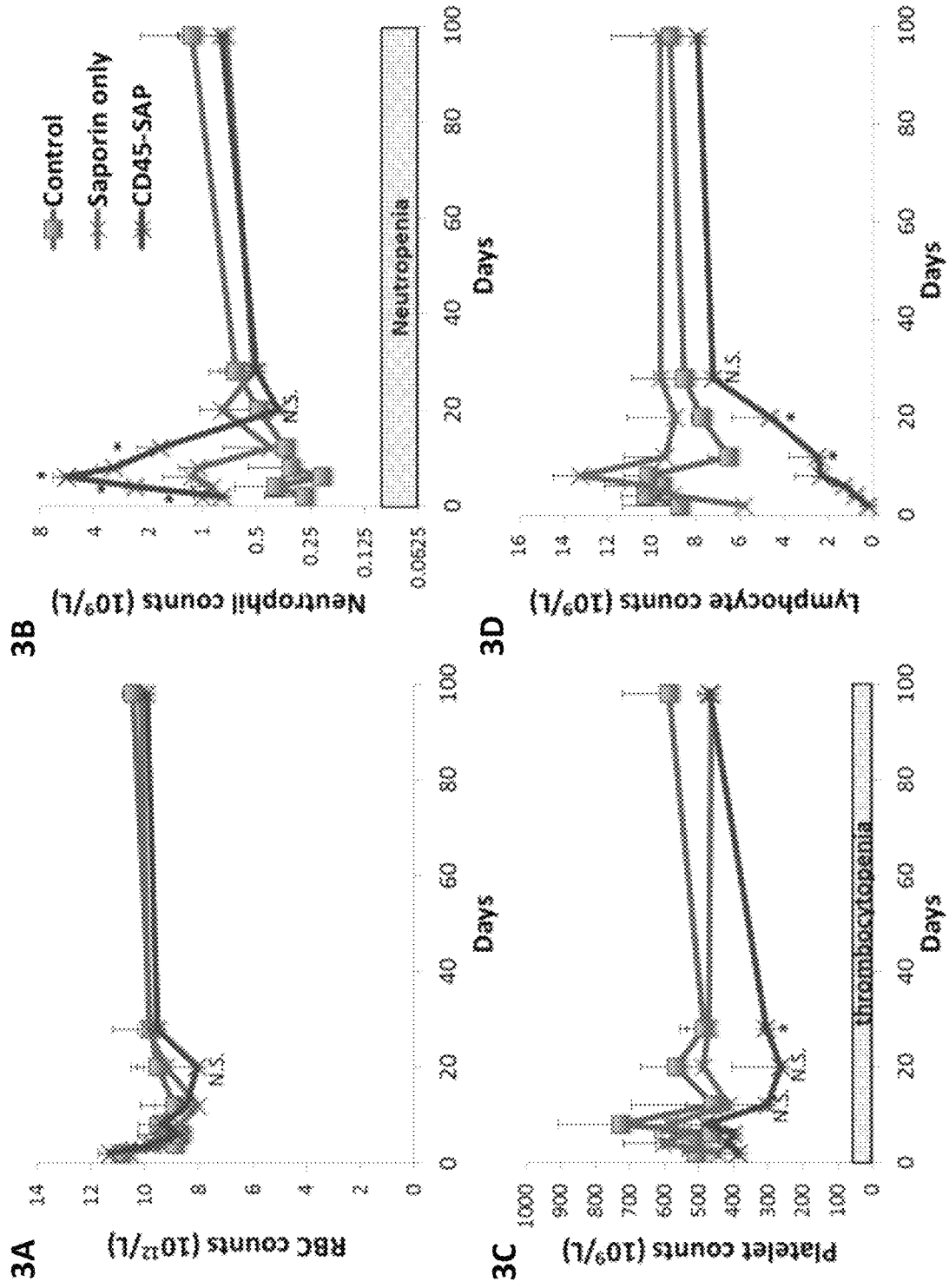
FIGS. 3A-3D illustrate the recovery of several hematological parameters, as assessed over a 100-day period in mice conditioned with CD45-SAP and that did not receive donor cell transplant. In particular.
Figures 4A, 4B, 4C:
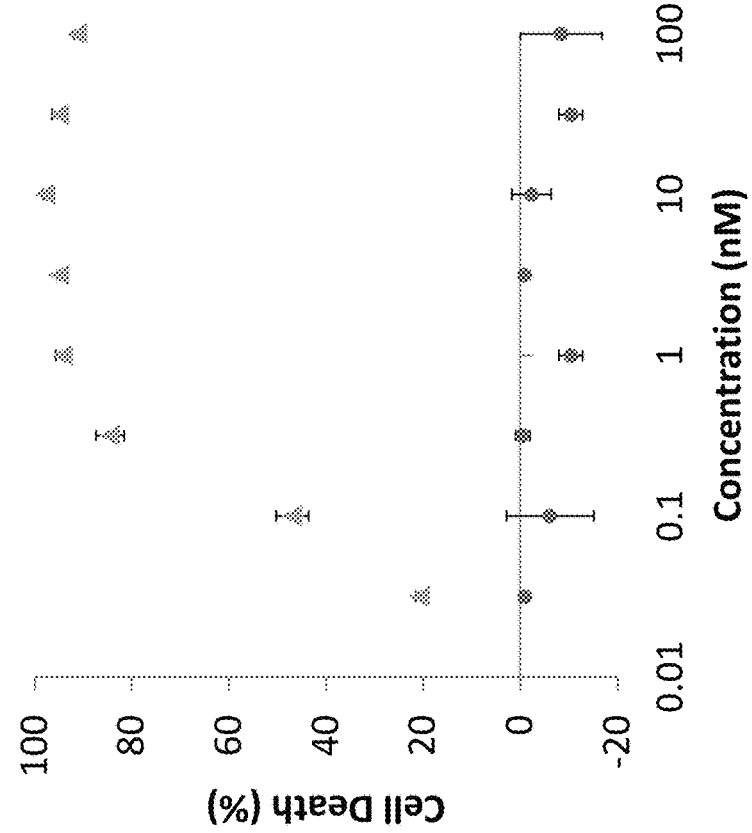
FIGS. 4A-4C illustrate the cell killing activity of a CD45-SAP immunotoxin in vitro and confirm that by targeting CD45, the immunotoxins disclosed herein may be internalized.
Figures 5A, 5B, 5C, 5D, 5E:
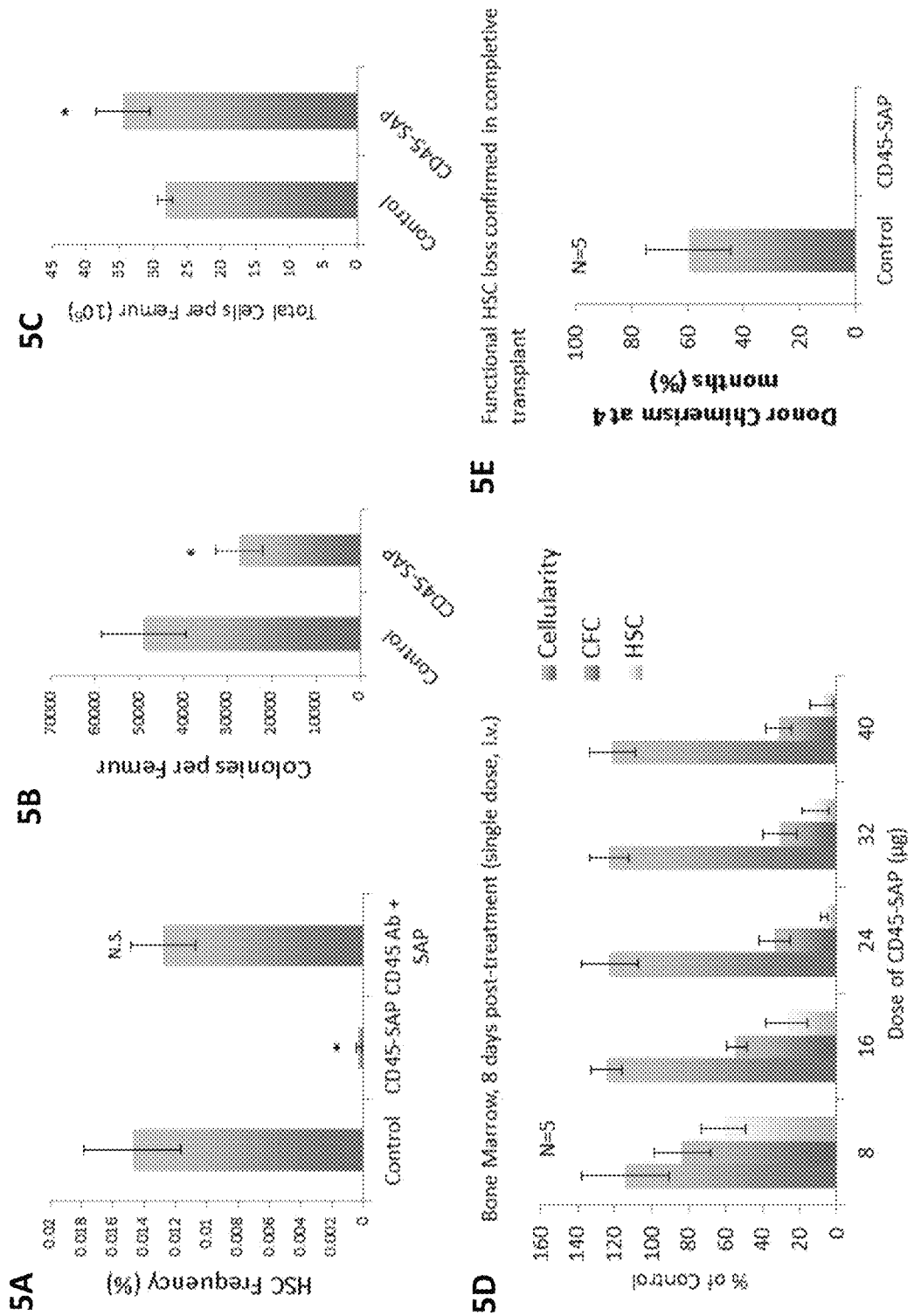
FIGS. 5A-5E illustrate that the CD45-SAP immunotoxin depletes hematopoietic stem cells (HSCs) in vivo.
Figures 6A, 6B, 6C, 6D:
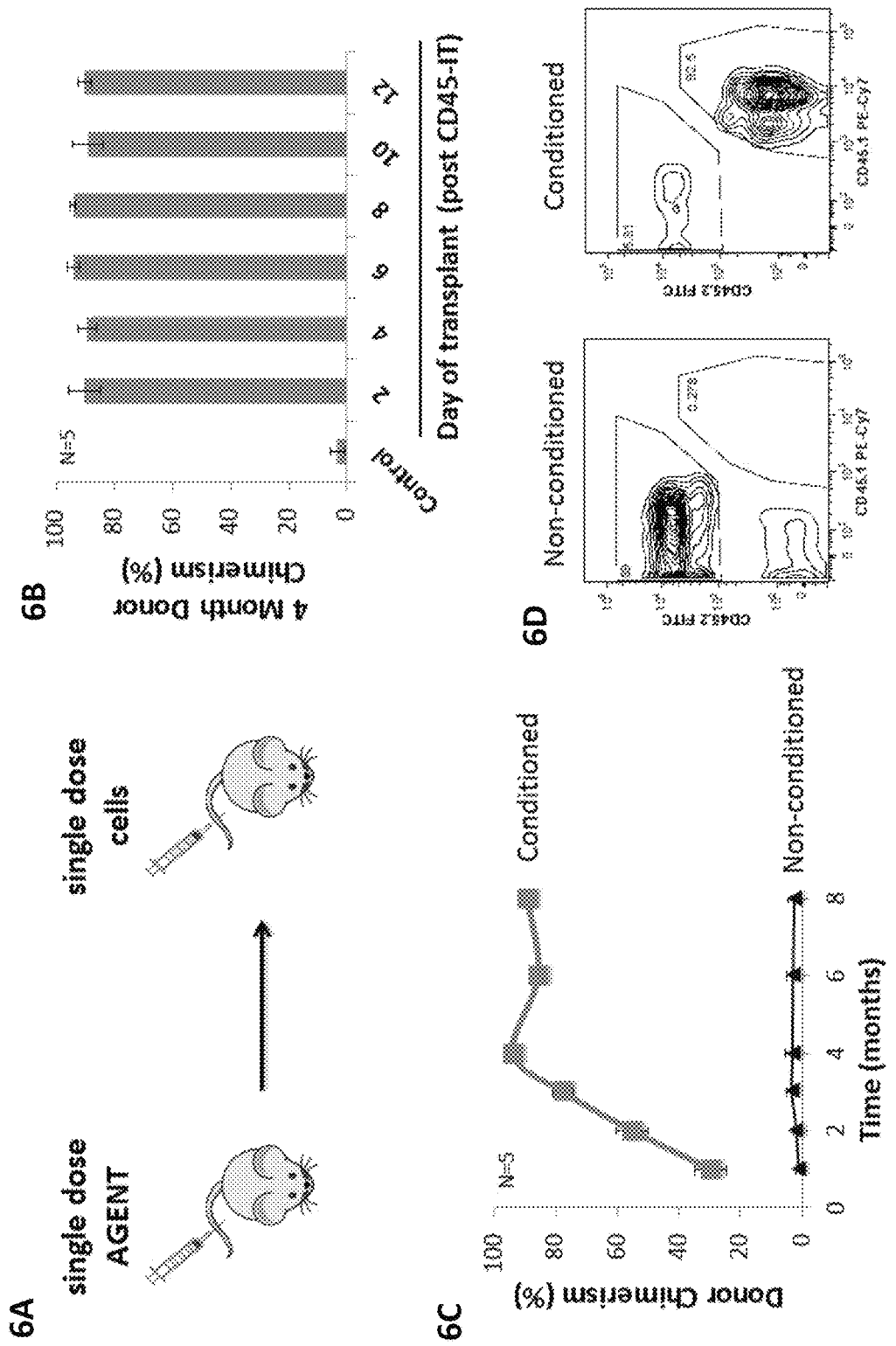
FIGS. 6A-6D show the engraftment results following the administration of the CD45-SAP in mice.

The lack of neutropenia observed following conditioning with CD45-SAP (as illustrated in FIG. 3B) and the observed expansion of neutrophils was a surprising result considering neutrophils express CD45. Without wishing to be bound by any particular theory, it may be possible that neutrophils, unlike other blood cells, do not internalize the CD45-SAP or, because of their short life-span (12 hours), that this effect is not visible due to quick turnover of the cell population. It is conceivable that the rapid expansion of neutrophils observed may be a response to CD45+ cell death, as neutrophils are responsible for clearance of apoptotic cells. It is not anticipated that the transient expansion of neutrophils will be an adverse effect, as neutrophils play a prominent role in fighting bacterial infections and their expansion will therefore limit the incidence of bacterial infection, a major cause of traditional conditioning-related mortality.

Although transient lymphopenia in B- and T-cells was observed, it may be that this is necessary (but perhaps not sufficient in itself) for engraftment to occur, as suggested by the ineffectiveness of ACK2 in immunocompetent animals and studies in our lab demonstrating regulatory T-cells directly interact with HSCs in the bone marrow and are necessary for HSC persistence (Fujisaki, J., et al., *Nature* (2011) 474, 216-219). While T-cell depletion may be an area of concern for HIV subjects, the transient nature of depletion may be acceptable on a case-by-case assessment of individual patients (especially prior to development of full-blown AIDS). Also, depletion of recipient T-cells may be advantageous as it would enable clearance of CCR5 positive T-cells which serve as viral reservoirs of HIV. The present inventors do not anticipate the transient T-cell depletion to be an issue for the treatment of other hemoglobinopathies, and it is important to note that current conditioning regimens fully ablate T-cell and B-cell populations.

The lack of anemia following CD45-SAP conditioning as evidenced by no decreases in red blood cells, hematocrit or hemoglobin levels, suggests that conditioning in accordance with the methods disclosed herein will be relevant to enabling transplantation in anemic conditions (e.g. sickle cell, Diamond-Blackfan anemia and thalassemias).

The compositions and methods disclosed herein may be used to treat or cure a subject having a disease (e.g., a stem cell disorder) that may benefit from hematopoietic stem cell or progenitor cell transplantation (e.g., sickle cell disease), including, for example autologous, allogeneic, gene-modified and gene-therapy methods. As used herein, the phrase "stem cell disorder" broadly refers to any disease, disorder or condition that may be treated or cured by conditioning a subject's target tissues, and/or by ablating an endogenous stem cell population in a target tissue (e.g., ablating an endogenous HSC or progenitor cell population from a subject's bone marrow tissue) and/or by engrafting or transplanting stem cells in a subject's target tissues. For example, Type I diabetes has been shown to be cured by hematopoietic stem cell transplant and may benefit from conditioning in accordance with the present inventions. Similarly, in certain aspects, the compositions and methods disclosed herein may be used for conditioning a subject undergoing treatment for a hematological malignancy. In certain aspects, the methods and compositions disclosed herein may be used to treat, cure or correct diseases selected from the group consisting of the following diseases: sickle cell anemia, thalassemias, Fanconi anemia, Wiskott-Aldrich syndrome, adenosine deaminase SCID (ADA SCID), HIV, metachromatic leukodystrophy, Diamond-Blackfan anemia and Schwachman-Diamond syndrome. In some embodiments, the subject has or is affected by an inherited blood disorder (e.g., sickle cell anemia) or an autoimmune disorder. In some embodiments, the subject has or is affected by a malignancy. For example, a malignancy selected from the group consisting of hematologic cancers (e.g., leukemia, lymphoma, multiple myeloma, or myelodysplastic syndrome) and neuroblastoma. In some embodiments, the subject has or is otherwise affected by a metabolic disorder. For example, in certain aspects the subject may suffer or otherwise be affected by a metabolic disorder selected from the group consisting of glycogen storage diseases, mucopolysccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper IGM syndrome, Chédiak-Higashi disease, hereditary lymphohistiocytosis, osteopetrosis, osteogenesis imperfect, the storage diseases, thalassemia major, sickle cell disease, systemic sclerosis, systemic lupus erythematosus, multiple sclerosis, juvenile rheumatoid arthritis and those diseases or disorders described in "Bone Marrow Transplantation for Non-Malignant Disease," *ASH Education Book,* 2000 (1) 319-338, the contents of which are incorporated herein by reference in their entirety.

In certain aspects, the immunotoxin compositions disclosed herein may be used to induce solid organ transplant tolerance. In such embodiments, the immunotoxin compositions and methods disclosed herein may be used to deplete or ablate a population of cells from a target tissue (e.g., to deplete HSCs from the bone marrow stem cell niche).

Following such depletion of cells from the target tissues, a population of stem or progenitor cells from the organ donor (e.g., HSCs from the organ donor) may be administered to the transplant recipient and following the engraftment of such stem or progenitor cells, a temporary of stable mixed chimerism achieved, thereby enabling long-term transplant organ tolerance without the need for further immunosuppressive agents. For example, the immunotoxins and methods disclosed herein may be used to induce transplant tolerance in a solid organ transplant recipient (e.g., a kidney transplant, lung transplant, liver transplant and heart transplant). The immunotoxins and methods disclosed herein are well-suited for use in connection the induction of solid organ transplant tolerance, particularly because a low percentage temporary or stable donor engraftment is sufficient to induce long-term tolerance of the transplanted organ.

The methods and compositions disclosed herein are characterized by their enhanced or improved engraftment efficiency. As used herein, the phrases "engraftment efficiency" and "efficiency of engraftment" generally refer to the efficiency with which an administered stem cell population (e.g., HSCs) engrafts in the conditioned target tissue of the subject. In certain embodiments, the efficiency of engraftment is increased by at least about 5%, 7.5%, 10%, 12.5%, 15%, 20%, 25%, 30%, 35%, 40%, 50%, 60%, 70%, 75%, 80%, 90%, 95%, 100% or more. In certain aspects, the determination of engraftment efficiency is assessed relative to the engraftment efficiency of a method in which the engraftment is performed without the conditioning methods disclosed herein.

In some embodiments, the stem cell population (e.g., an exogenous stem cell population) is administered to the target tissues of the subject after the toxin or immunotoxin (e.g., an anti-CD45-SAP immunotoxin) has cleared or dissipated from the subject's target tissues. By allowing the toxin or immunotoxin to clear or to otherwise be reduced to undetectable levels in the subject's target tissues, the ability of any lingering toxin or immunotoxin to exert a cytotoxic effect on the administered stem cell population may be reduced or otherwise eliminated, thereby further increasing the engraftment efficiency of the methods and compositions disclosed herein. Accordingly, in some embodiments, the stem cell population is administered to the subject after the concentration of the immunotoxin in the subject's target tissue has been reduced to an undetectable concentration. The period of time necessary to clear the toxin or immunotoxin from the subject's target tissue may be determined using routine means available to one of skill in the art, for example, by detecting the concentration of the agent, toxin or immunotoxin in the subject's targeted tissue. In addition, the period of time necessary to clear the toxin or immunotoxin from the target tissue be influenced by, or otherwise determined with reference to, among other things, the properties of the agent, toxin or immunotoxin, the administered does of the agent, toxin or immunotoxin, the subject's condition and/or co-morbidities (e.g., renal insufficiency) and the subject's target tissue. For example, in some embodiments, the stem cell population is administered to the target tissue of the subject at least one, two, three, four, five, six, seven, ten, twelve, fourteen, twenty one, thirty six, forty two, fifty six, sixty three, seventy, eighty, ninety, one hundred, one hundred and twenty days, six months, nine months, twelve months, or more, after the immunotoxin has cleared or dissipated from the target tissues of the subject.

As used herein, the term "subject" refers to an animal, for example, a mammal or a human to whom the treatments disclosed herein may be provided. For treatment of those disease states which are specific for a specific animal such as a human subject, the term subject refers to that specific animal. In certain embodiments, the subject is a human (e.g., an adolescent, adult or an elderly human).

The compositions of the present invention may be prepared and pharmaceutically acceptable carriers and excipients selected, as described in detail in, for example, L. William, Remington: The Science and Practice of Pharmacy. 22nd ed. Pharmaceutical Press (2012), the entire contents of which are incorporated herein by reference. In certain aspects, the compositions disclosed herein (e.g., a CD45-SAP conjugate) are formulated for parenteral administration to a subject.

As used herein, the term "effective amount" means an amount sufficient to achieve a meaningful benefit to the subject (e.g., condition the subject's target tissue for transplant). For example, an effective amount of the agents that are the subject of the present inventions may be generally determined based on the activity of such agents and the amount of such agents that are necessary to ablate or deplete the stem cell niche. An effective amount of the compositions (e.g., antibody-toxin conjugates) necessary to condition the subject or to ablate the subject's hematopoietic stem cells or progenitor cells can be readily determined depending on the subject's disease and other related characteristics. Such characteristics include the condition, general health, age, subjective symptoms, objective appearance, sex and body weight of the subject.

In some embodiments, an effective amount of the immunotoxin compositions disclosed herein achieves maximal stem cell depletion (e.g., about 90%, 91%, 92%, 93%, 94%, 95%, 96%, 97%, 97.5%, 98%, 99%, 99.5% or more depletion of hematopoietic or progenitor stem cells from the target tissues of the subject). In some embodiments, an effective amount of the compositions disclosed herein is determined on the basis of a subject's weight. For example, in certain aspects, such an effective amount of the compositions disclosed herein is or comprises one or more doses of ranging between about 10-0.01 mg/kg. In certain aspects, an effective amount of the compositions disclosed herein (e.g., a CD45-toxin or CD117-toxin conjugate) is or comprises one or more doses of 4.0 mg/kg. In some aspects, an effective amount of the compositions disclosed herein is or comprises one or more doses of 3.0 mg/kg. In certain aspects, an effective amount of the compositions disclosed herein is or comprises one or more doses of 2.0 mg/kg. In some aspects, an effective amount of the compositions disclosed herein is or comprises one or more doses of 2.5 mg/kg. In certain aspects, an effective amount of the compositions disclosed herein is or comprises one or more doses of 2.0 mg/kg. In certain embodiments, an effective amount of the compositions disclosed herein (e.g., a CD45-toxin or CD117-toxin conjugate) is or comprises one or more doses of 1.5 mg/kg. In certain aspects, an effective amount of the compositions disclosed herein (e.g., a CD45-SAP conjugate) is or comprises one or more doses of 1.0 mg/kg.

Also disclosed herein are methods and assays for identifying candidate agents that may be useful for selectively depleting or ablating an endogenous stem cell population in accordance with the methods disclosed herein. In certain embodiments, such methods comprise a step of contacting a sample (e.g., a sample obtained from a subject) comprising the stem cell population with a test agent coupled to a toxin. Following such a contacting step, a determination is made as to whether one or more cells of the stem cell population are depleted or ablated from the sample, wherein the depletion or ablation of one or more cells of the HSC or progenitor cell population following the contacting step identifies the test agent as a candidate agent which may be useful for selectively depleting or ablating an endogenous stem cell population. In some embodiments, the cell is contacted with the test agent for at least about 2-24 hours or more. As used herein, the terms "contact" and "contacting" refer to bringing two or more moieties (e.g., a cell and an agent) together, or within close proximity of one another such that the moieties may react. For example, in one embodiment the assays of the present invention comprise a step of contacting a stem cell population with a test agent.

It is to be understood that the invention is not limited in its application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

While certain agents, compounds, compositions and methods of the present invention have been described with specificity in accordance with certain embodiments, the following examples serve only to illustrate the methods and compositions of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

The present inventors have developed and investigated the use of a biotin-labeled anti-CD45 mouse monoclonal antibody in conjunction with a streptavidin-saporin conjugate to create an immunotoxin to CD45 (CD45-SAP). Saporin is a member of the ricin family of toxins that catalytically inactivates ribosomes halting protein synthesis thereby leading to cell death. However, unlike ricin, saporin lacks an internalization domain and only induces death when coupled to a ligand or antibody that is internalized (Bergamaschi, G., et al., *Br J Haematol* (1996), 93, 789-794). This allows the present inventors to selectively target which cells to kill, while sparing other tissues, reducing overall toxicities.

Whole bone marrow cells were treated with CD45-SAP ex vivo and a colony forming assay was performed to assess short-term stem cell and progenitor activity. Potent inhibition of colony forming activity by CD45-SAP was observed in a dose dependent manner ($IC_{50}$ of 1 nM) while free saporin exhibited no growth inhibition at 100 nM.

The present inventors next investigated whether in vivo administration of CD45-SAP as a single injection could deplete stem cells in the bone marrow, as assessed by flow cytometry of the bone marrow harvested 8 days post-injection. This time point was selected as previous reports suggested sustained depletion of hematopoietic stem cells (HSCs) or progenitor cells from the bone marrow is required for efficient donor cell engraftment to occur (Xue, X., et al. *Blood* (2010), 116, 5419-5422). Using the optimal ratio of antibody:toxin, which was determined to be 1:1 in previous experiment (4 mice per group), a dose-response study was conducted to determine that 24 µg of CD45-SAP achieves maximal depletion of HSCs (approximately 98% depleted, 4 mice per group, as illustrated in FIG. 2A. This dose utilizes a low amount of saporin (approximately 14% of the $LD_{50}$ of free saporin). HSC depletion was specific to CD45-SAP as the present inventors failed to observe HSC depletion in a control group co-injected with non-biotinylated anti-CD45 antibody and streptavidin-saporin (CD45 Ab+SAP, FIG. 2A). Short-term progenitor activity (colony assay) of the bone marrow post-conditioning was also tested and the present inventors observed a 50% decrease in colony forming activity, despite the 98% depletion in stem cells, as shown in FIG. 2B. Interestingly, the overall cellularity (number of live cells in a femur) of the bone marrow fraction is actually increased in CD45-SAP treated animals relative to the control, likely due to hematopoietic recovery (FIG. 2C). This observed result is in stark contrast to low-dose irradiation which decreases bone marrow cellularity by 66% at the same time point (Andrade, J. et al., *Biol Blood Marrow Transplant* (2011), 17, 608-619). The foregoing therefore demonstrate that the CD45-SAP agents disclosed herein can be used to efficiently clear hematopoietic stem cells or progenitor cells from the bone marrow.

The present inventors next investigated whether our single-dose regimen of CD45-SAP would enable long-term engraftment of donor cells. Whole bone marrow cells from GFP+ donor mice were transplanted so that we could track engraftment in the GFP-null recipient background. The transplants consisted of injecting $1 \times 10^7$ whole bone marrow cells (which contain approximately 500 long-term stem cells, <5% of total stem cells in mouse), a standard dose in murine transplantation studies investigating conditioning. Whole bone marrow was used, rather than purified stem cells, as this more closely mimics transplantation procedures in the clinic. To characterize the window for transplantation the GFP+ cells were transplanted at various time points post CD45-SAP (2, 4, 6, 8, 10 or 12 days, 5 mice per group). Thus far, we have tracked chimerism in the peripheral blood for 2 months, which revealed high levels of donor engraftment (55% for CD45-SAP versus 1% for control unconditioned mice, 55-fold increase, as illustrated in FIG. 2D). The present inventors have determined in previous pilot studies that the engraftment and mixed-chimerism is long-term (monitored for 4 months). Surprisingly no difference in engraftment was observed between time points, indicating a large transplantation window, as illustrated in FIG. 2E. This is in contrast to irradiation-based conditioning in mice, where transplantation 24 hours post-irradiation is optimal. Tri-lineage analysis of the overall distribution of B-, T- and myeloid cells in transplanted mice did not reveal a bias (FIG. 2F). Analysis within each of the lineages, confirmed that donor cells contribute to all 3 lineages, indicating true stem cell engraftment, as illustrated in FIG. 2G. As myeloid cells have the quickest lineage turnover (Tak, T., et al. *J Leukoc Biol* (2013), 94, 595-601) due to their short lifespan (12 hours), chimerism of the myeloid fraction is often used as an indicator of the level of donor engraftment at early time points (<4 months) (Valcarcel, D., et al. *Bone Marrow Transplant* (2003), 31, 387-392). As shown in FIG. 2G, 88% donor chimerism was observed in the myeloid lineage at 8 months, a period considered to represent long-term reconstitution.

To characterize CD45-SAP as "non-myeloablative" conditioning we next sought to determine whether mice conditioned by the agent but do not receive donor cell transplant were able to survive. Our conditioning regimen was found to be non-lethal as all mice (n=4) survived as assessed for 100 days, at which time the study was terminated. In contrast, mice receiving total body irradiation (TBI) conditioning will die within 15-18 days if donor cells are not transplanted. The present inventors also performed serial blood analysis in the mice over the 100 day period to determine loss and recovery of various blood cells (FIGS. 3A-3D). As illustrated in FIG. 3A, CD45-SAP did not induce any red blood cell loss, and more importantly, no neutropenia (FIG. 3B) or thrombocytopenia was observed (FIG. 3C; only a 30% drop in platelets was observed at day 20; a 90% drop would be considered thrombocytopenic). While, CD45-SAP displayed potent depletion of B- and T-lymphocytes, recovery was rapid, with 20% recovery within 6 days and complete recovery by 30 days, as shown in FIG. 2D.

Example 2

The present inventors next assessed the toxicity of the CD45-SAP immunotoxin relative to the toxicity of irradiation in non-transplanted mice. Time course experiments were performed in mice to compare the toxicity of CD45-SAP conditioning relative to an equivalent sub-lethal 5Gy dose of total body irradiation. Two days post-conditioning, the mice were euthanized and submitted to a rodent pathologist for femur and thymus mounting, sectioning and staining with hematoxylin and eosin. Complete blood counts and flow cytometry analyses were also performed. Non-conditioned mice represent the control.

Figures 7A, 7B, 7C, 7D, 7E, 7F:
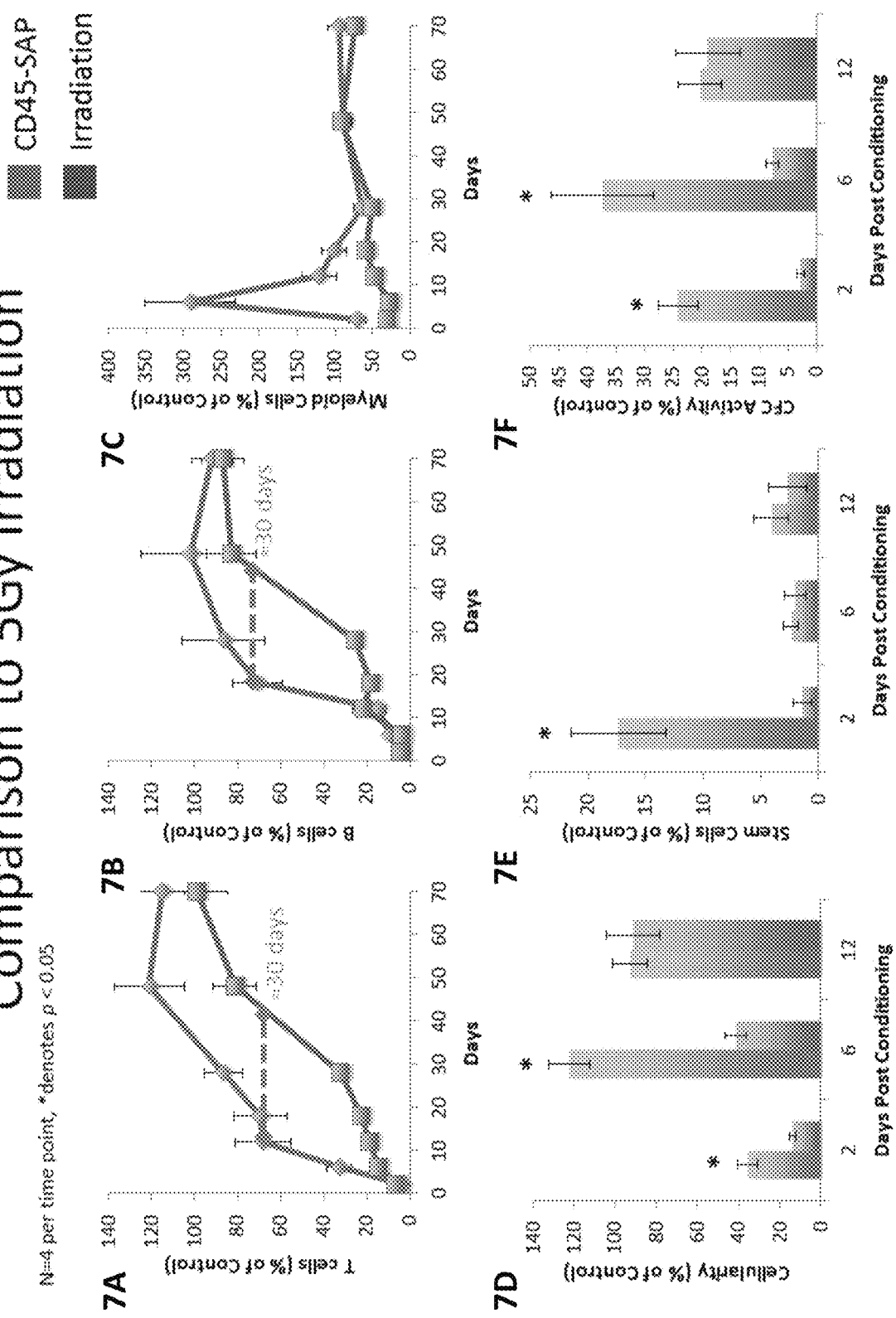
FIGS. 7A-7F compare the toxicity of the CD45-SAP immunotoxin agent relative to a traditional irradiation (5Gy) conditioning regimen. In particular, depicted are the comparisons of such CD45-SAP immunotoxin relative to traditional irradiation in T-cells (FIG. 7A), B-cells (FIG. 7B), myeloid cells (FIG. 7C), cellularity (FIG. 7D), stem cells (FIG. 7E) and CFC activity (FIG. 7F).

As illustrated in FIGS. 7A and 7B, a much quicker recovery of B- and T-cell populations was observed in the CD45-SAP group, relative to irradiation. As shown in FIGS. 7D and 7F, bone marrow cellularity and colony forming counts (progenitor activity assay) were also less adversely affected with CD45-SAP relative to irradiation.

Figure 8:
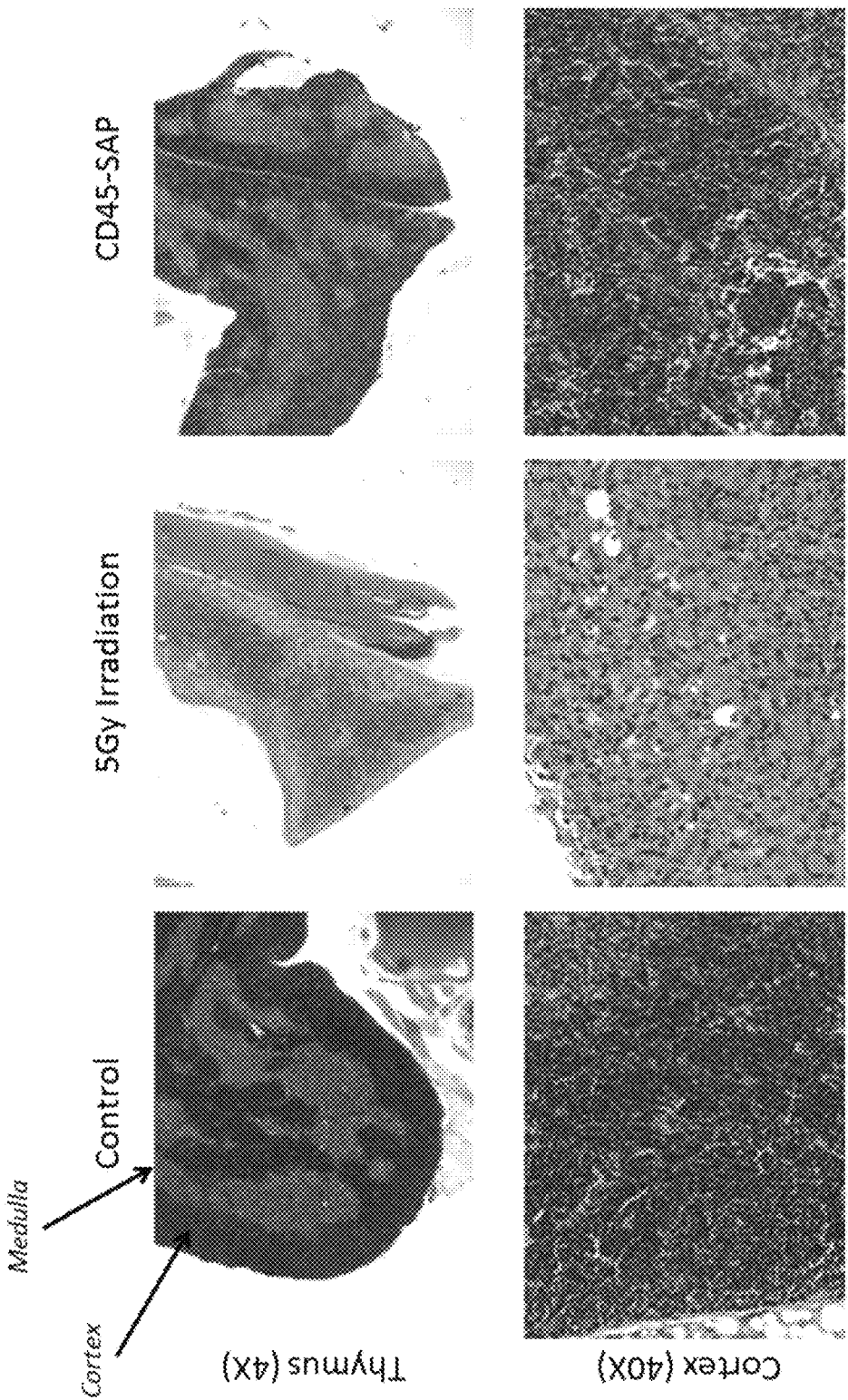
FIG. 8 demonstrates that no damage to the thymus was observed in mice administered the CD45-SAP immunotoxin relative to irradiation 2 days post-conditioning. In contrast, thymic atrophy was observed in mice following conditioning with irradiation.

Two days post-conditioning, live mice (under anesthesia) were mounted on to a custom-made 2-photon confocal live imaging microscope. High molecular weight rhodamine-dextran conjugate was injected intravenously and images of the calvarium (skull cap) bone were taken 30 minutes post-administration to assess vascular integrity. Non-conditioned mice represent the control. As depicted in FIG. 8 and unlike irradiation, no damage to the thymus was observed following conditioning with CD45-SAP relative to irradiation.

Figure 9:
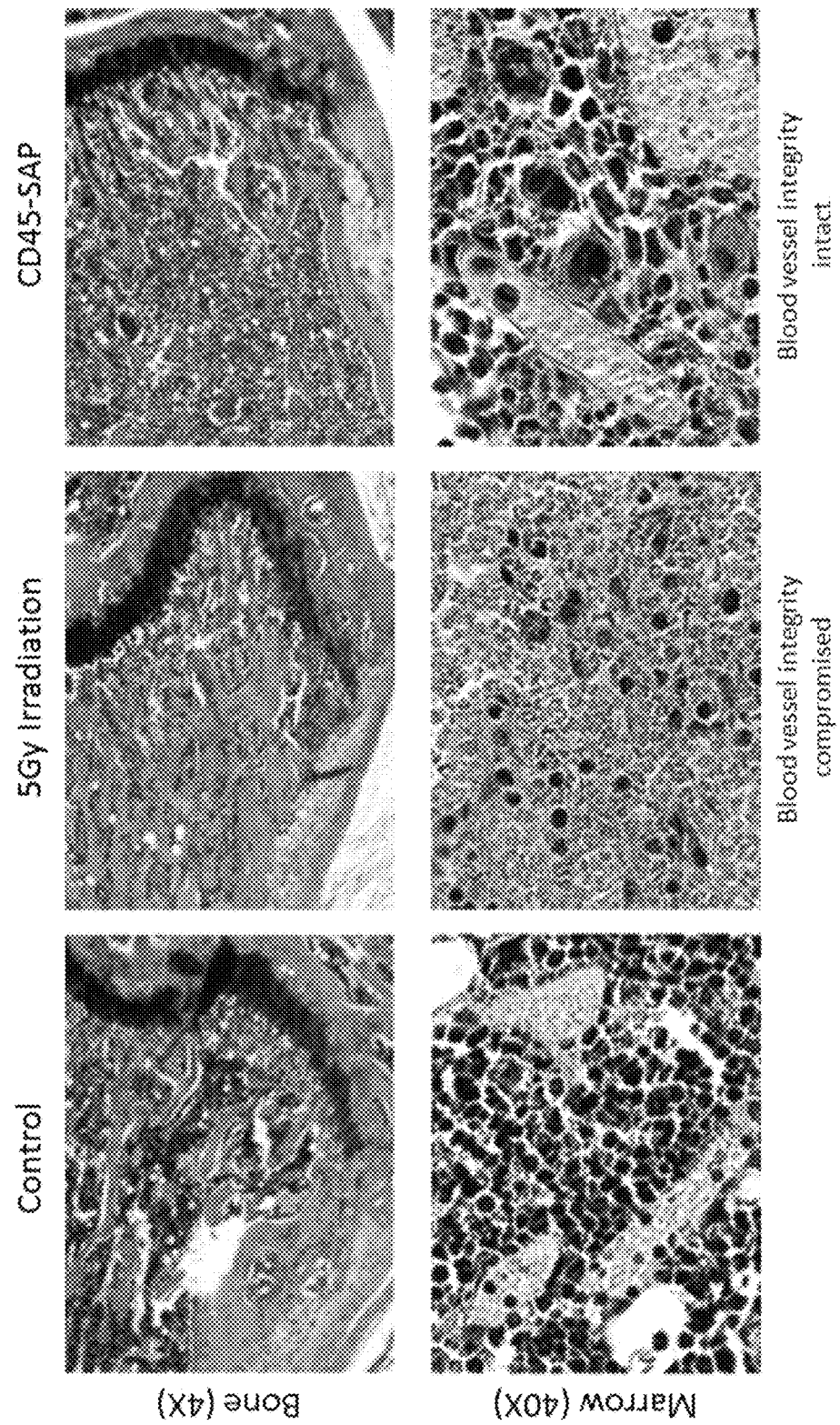
FIG. 9 shows bone marrow histology and confirms that blood vessel integrity remained intact in mice with CD45-SAP 2 days post-conditioning. In contrast, blood vessel integrity was compromised in mice following irradiation 2 days post-conditioning.
Figure 10:
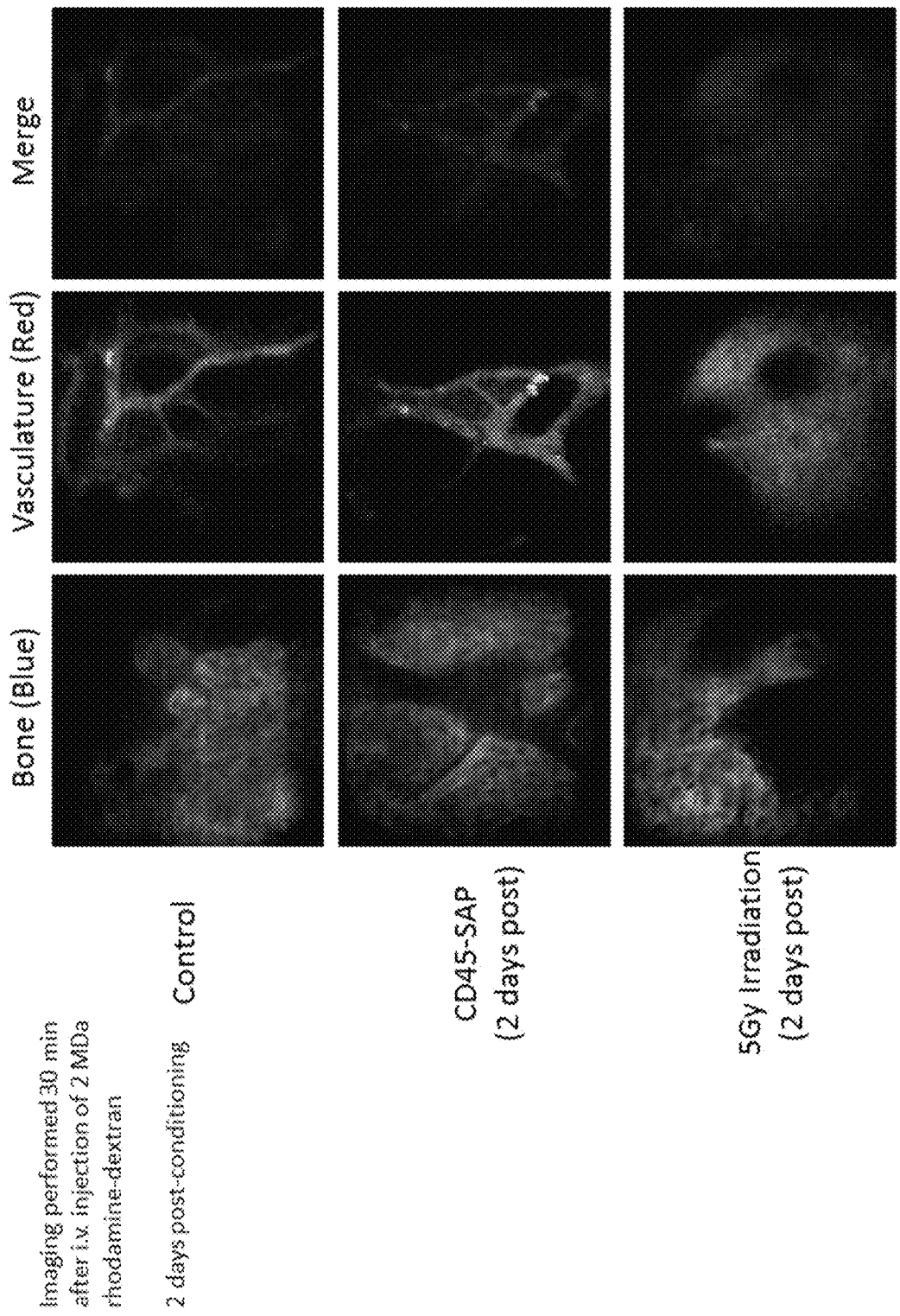
FIG. 10 depicts that vascular integrity was preserved 2 days post-conditioning with the CD45-SAP agent. In contrast, blood vessel integrity was compromised in mice following irradiation 2 days post-conditioning.

As shown in FIG. 9, bone marrow histology confirms that blood vessel integrity remained intact with CD45-SAP relative to irradiation. FIG. 10 further depicts that 2 days post-conditioning with the CD45-SAP immunotoxin, vascular integrity was preserved.

The foregoing results therefore demonstrate that a conditioning regimen using CD45-SAP is associated with reduced toxicity relative to total body irradiation.

Example 3

To investigate the utility of the CD45-SAP immunotoxin in correcting an animal model of sickle cell disease, the present inventors created sickle cell mice chimeras by myeloablative conditioning of wild-type recipients, followed by transplantation with bone marrow cells from human sickle hemoglobin knock-in mice (Townes mice). Two months post-transplantation, the sickle cell mice were conditioned with CD45-SAP and transplanted with whole bone marrow cells from wild-type CD45.1 donor mice.

Figures 11A, 11B, 11C, 11D:
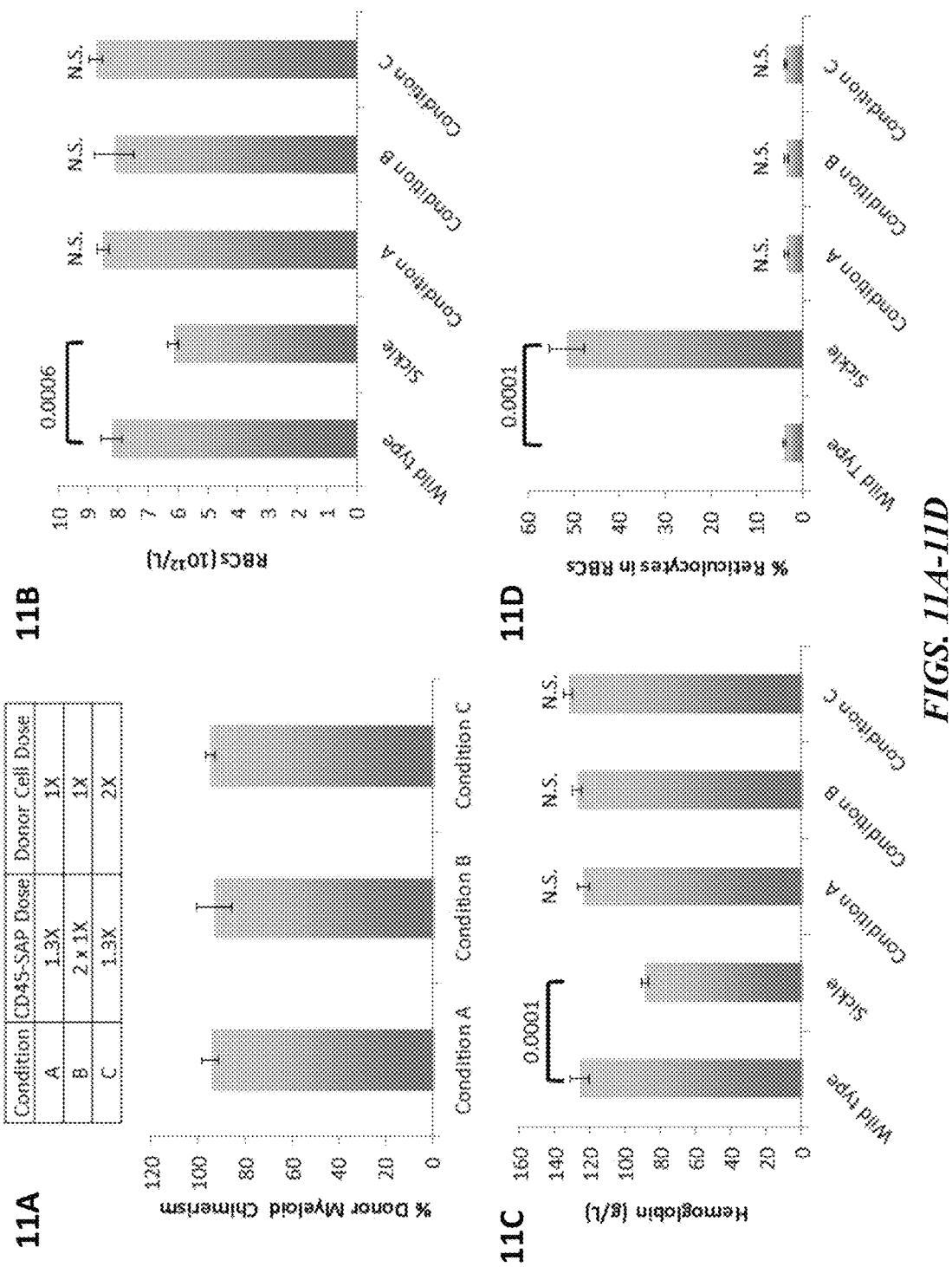
FIGS. 11A-11D illustrate that engraftment using CD45-SAP conditioning is capable of correcting sickle cell anemia in a mouse model.

Three different transplantation conditions were investigated (outlined in FIG. 11A) with n=6 mice per condition. Mice in the condition A group received 1.3× the standard dose of CD45-SAP used previously in wild-type mice at Day 0, followed by transplantation with $1 \times 10^7$ donor whole bone marrow cells at Day 3 (1× cell dose). Mice in the condition B group received injections of 1× CD45-SAP at day 0 and Day 3, followed by transplantation with $1 \times 10^7$ whole bone marrow cells at Day 6 (1× cell dose). Mice in the condition C group received 1.3× CD45-SAP at Day 0, and were transplanted with $1 \times 10^7$ wild-type whole bone marrow cells at days 3 and 6 (2× cell dose). Donor cell engraftment and disease correction was assessed 4 months post-transplantation and compared to age- and sex-matched non-transplanted sickle chimeras or wild-type mice.

Figure 12A:
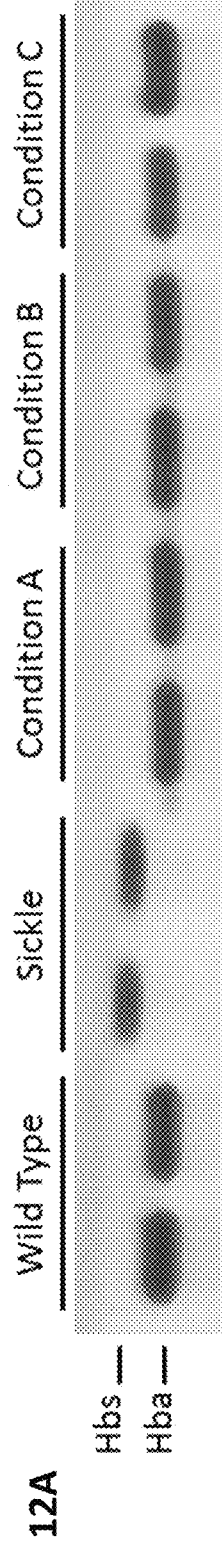
FIGS. 12A-12B illustrates correction of sickle cell in the mouse model and shows that sickle hemoglobin protein was no longer observed in the blood of conditioned mice.
Figure 12B:
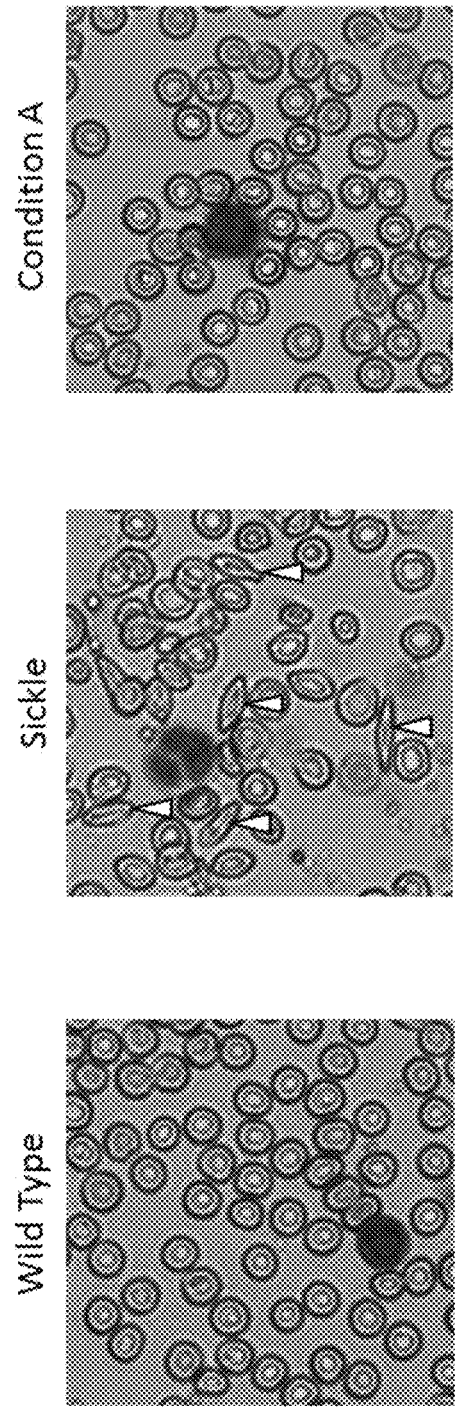
Figures 13A, 13B:
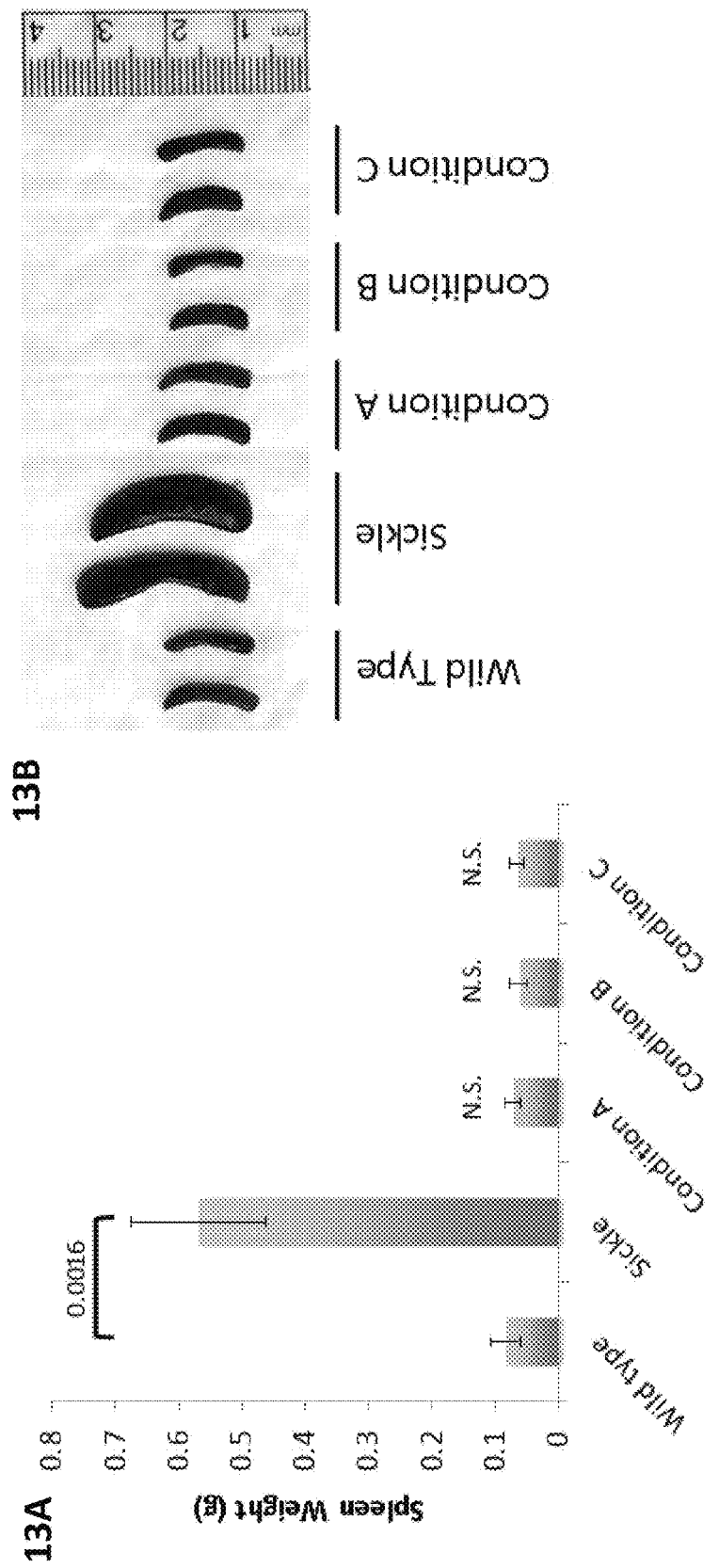
FIGS. 13A-13B demonstrate correction of spleen sizes in animals that were conditioned with CD45-SAP followed by transplantation. In particular, FIGS. 13A and 13B respectively illustrate that spleen weights and spleen sizes in the sickle cell mice model were corrected in those mice that were conditioned with CD45-SAP. N.S. denotes statistically not significant.

As illustrated in FIGS. 11A-11D, red blood cell, reticulocyte, hematocrit and hemoglobin levels return to normal. Additionally, as shown in FIGS. 12A-12B, sickle hemoglobin protein was no longer observed in blood. Pathology on spleen and liver was also performed and, as illustrated in FIGS. 13A-13B, spleen size was restored to normal in the CD45-SAP conditioned mice. The foregoing results therefore demonstrate the correction of sickle cell disease in a mouse model.

Example 4

In order to further evaluate immunotoxins as a conditioning strategy to vacate endogenous HSCs from their niches, the present inventors targeted cell surface antigens present on HSCs (mouse and human) using saporin-based immunotoxins and conducted our experiments in fully immunocompetent C57Bl/6 mice; a background that has proven to be challenging for antibody-based conditioning.

Figures 14A, 14B, 14C, 14D, 14E:
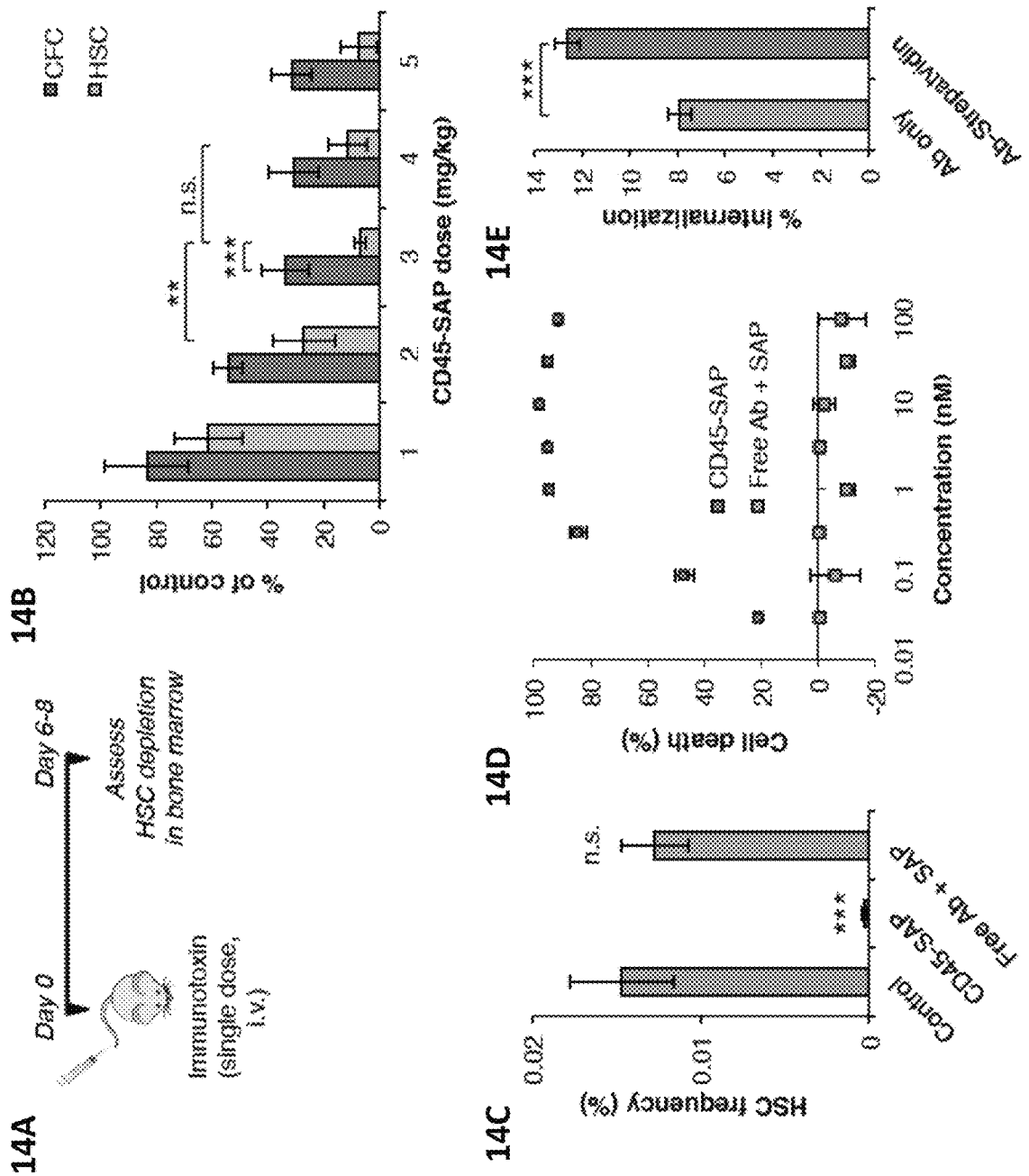
FIGS. 14A-14E demonstrate that CD45-SAP exhibits potent cell depletion activity.
Figures 15A, 15B, 15C, 15D, 15E, 15F, 15G:
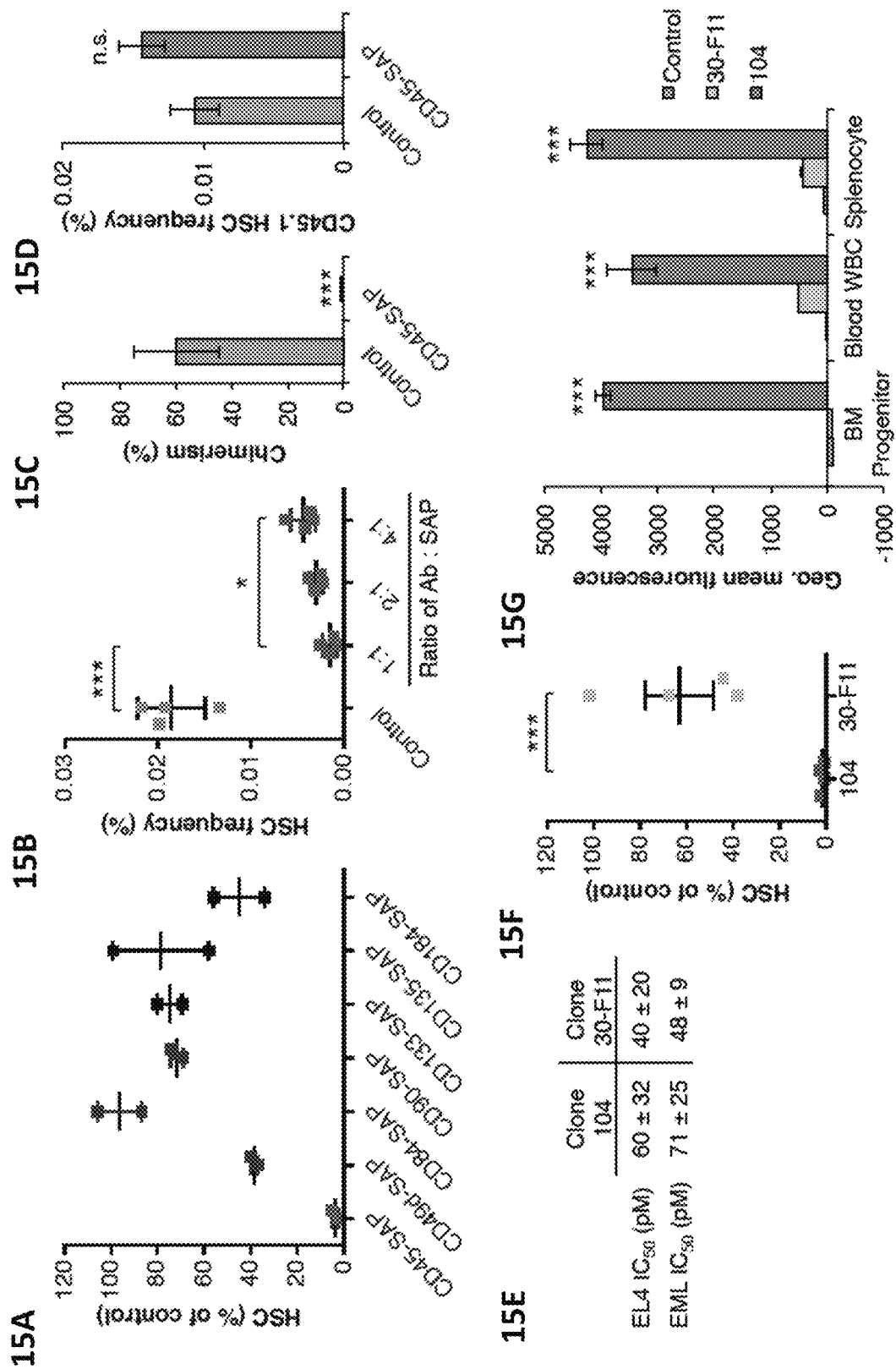
FIGS. 15A-15G illustrate the cell depletion activity of immunotoxins.

Immunotoxins were prepared by combining appropriate biotinylated monoclonal antibodies with streptavidin-saporin conjugate and HSC depletion was assessed by the experimental scheme in FIG. 14A. Among the candidate antigen targets evaluated (CD45, CD49d, CD84, CD90, CD133, CD135 and CD184) in our in vivo screen, a saporin-based immunotoxin targeting CD45 (CD45-SAP) was found to efficiently deplete bone marrow HSCs (FIG. 15A). Ratio and dose optimization studies (FIG. 14B and FIG. 15B) identified a single CD45-SAP dose (by i.v. injection) of 3 mg/kg of 1:1 antibody to streptavidin-saporin ratio achieved maximal immunophenotypic HSC depletion (98% by flow cytometry). In addition to HSC depletion, the colony forming activity of bone marrow progenitors decreased in a dose-dependent manner, but was less-adversely affected than HSCs (FIG. 14B). Competitive bone marrow transplantation confirmed the depletion of functional HSCs by CD45-SAP (FIG. 15C). As expected, non-biotinylated CD45 antibody plus streptavidin-saporin was unable to deplete HSCs in vivo (FIG. 14C). Furthermore, as the CD45 monoclonal antibody employed (clone 104) selectively recognizes CD45.2 isoform of murine CD45, the immunotoxin was unable to deplete HSCs in CD45.1 congenic mice (FIG. 15D). Together, these results are consistent with antigen-specific depletion of HSCs by CD45-SAP.

To characterize CD45-SAP immunotoxin, the inventors performed a series of in vitro experiments using the murine hematopoietic cell lines, EML (a multi-potent progenitor line) and EL4 (a T-cell lymphoma line). EML cells are akin to hematopoietic stem and progenitor cells as they are dependent on stem cell factor (SCF) for growth and undergo multi-lineage differentiation upon cytokine stimulation. In addition to the CD45 antibody clone 104, the present inventors also investigated clone 30-F11 (another anti-CD45 antibody) and both clones potently induced EML and EL4 cell death with similar $IC_{50}$ values ranging between 40-71 pM (FIG. 14D and FIG. 15E). Non-biotinylated antibody in the presence of streptavidin-saporin failed to induce cell death in vitro (FIG. 14D), demonstrating targeted-saporin specificity. Quantification of CD45 receptor internalization in EL4 cells using clone 104, showed 7% internalization of the antibody alone and 12% internalization of antibody-streptavidin complex over a 24 hour period (FIG. 14E). Surprisingly, despite equivalent activity of both cones in vitro, only clone 104 was capable of efficient HSC depletion in vivo (FIG. 15F). Assessment of in vivo persistence (24 hours post-administration) revealed clone 104 prominently bound to peripheral white blood cells, splenocytes and HSC-containing bone marrow LKS (Lin− cKit+ Sca1+) cells whereas clone 30-F11 displayed poor persistence in vivo (FIG. 15G).

Taken together, the foregoing results suggest that in vivo binding and internalization of CD45-SAP immunotoxin efficiently depletes HSCs from the bone marrow.

Example 5

The inventors next investigated whether HSC depletion by CD45-SAP could enable donor cell engraftment. As the donor graft may be negatively affected by unbound CD45-SAP in vivo, the present inventors varied the time of transplantation to identify the optimal transplantation window (FIG. 16A) and explored transplantation of 2 donor cell types (in different cohorts): congenic CD45.1 cells, which cannot be targeted by the CD45-SAP, or syngeneic CD45.2-GFP cells which can potentially be targeted. A dose of ten million whole bone marrow donor cells was used for transplantation, consistent with prior murine reduced conditioning studies and corresponds to approximately 2% of total murine marrow, thereby mimicking human transplantation where approximately 5% of donor marrow is harvested.

Figures 16A, 16B, 16C, 16D, 16E, 16F:
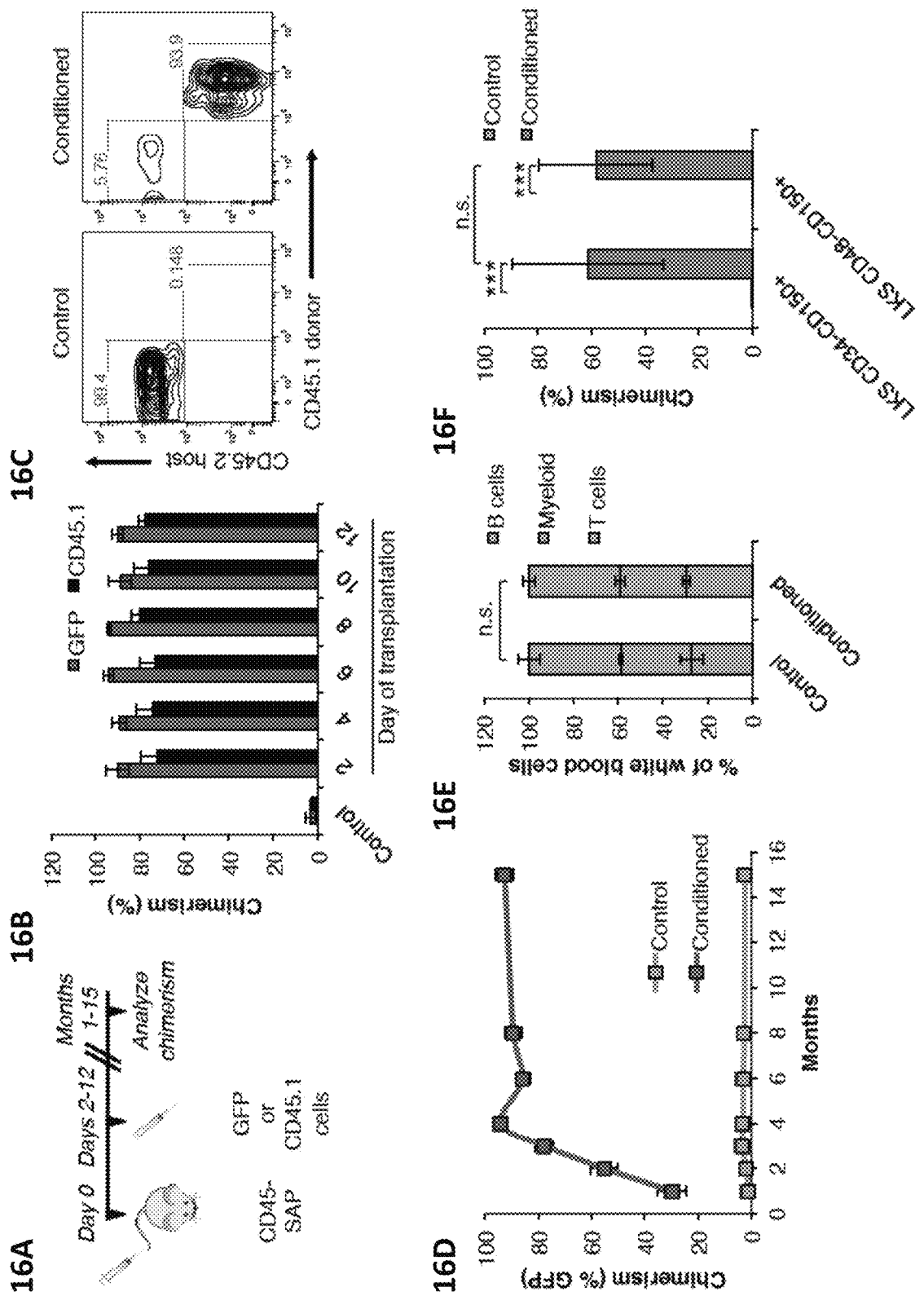
FIGS. 16A-16F show that CD45-SAP enables efficient donor cell engraftment.
Figures 17A, 17B, 17C, 17D, 17E:
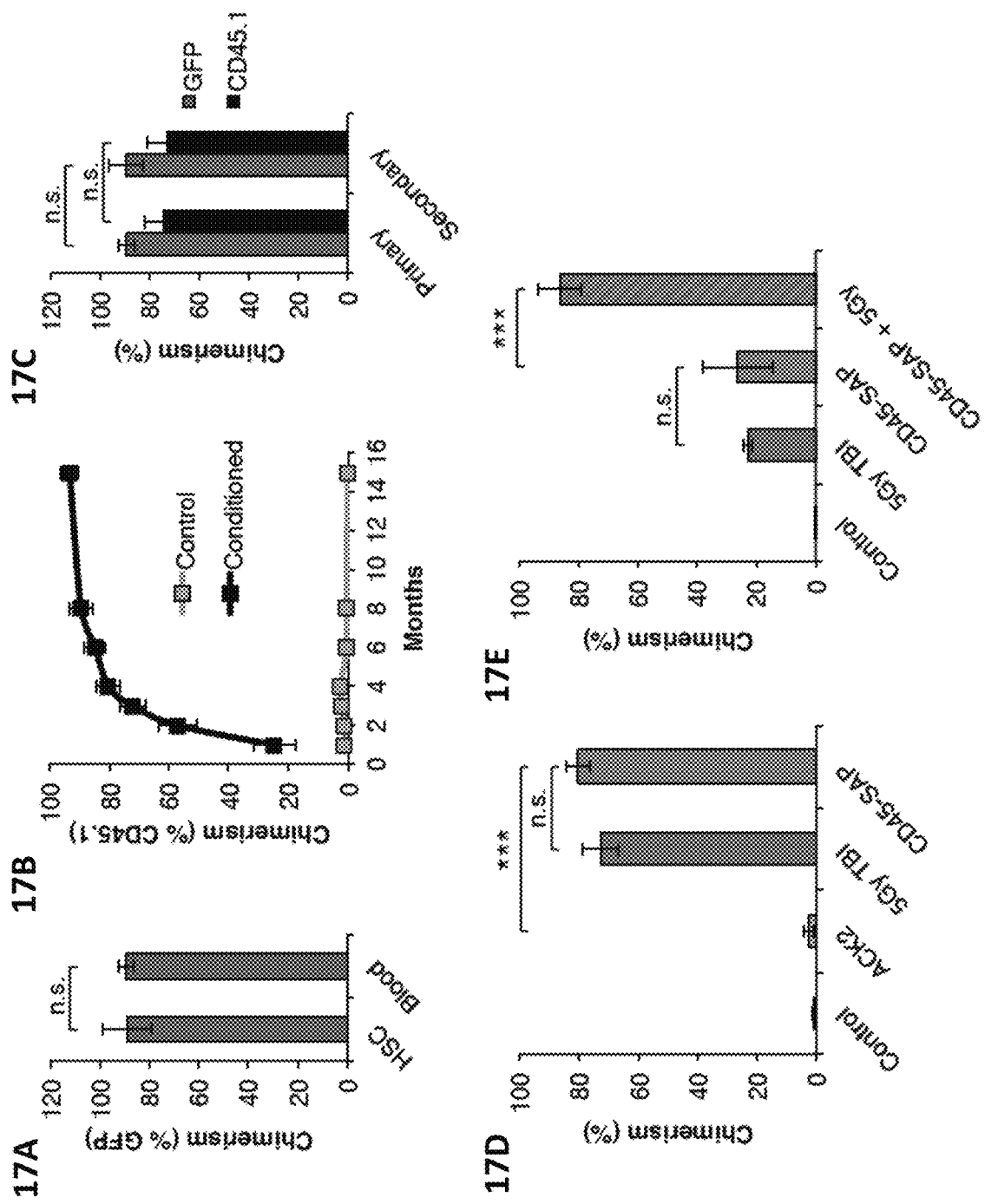
FIGS. 17A-17E illustrate donor engraftment post-administration of CD45-SAP.

Four months post-transplantation the present investigators observed 75-90% donor cell engraftment in the peripheral blood for both donor cell types in animals conditioned with CD45-SAP (FIGS. 16B and 16C). Strikingly, equivalent levels of engraftment were observed for cells transplanted anywhere between 2-12 days post CD45-SAP administration (FIG. 16B), demonstrating creation of a wide transplantation window. Unconditioned control animals failed to demonstrate meaningful donor engraftment, with chimerism levels <2% (FIGS. 16B and 16C). Similar to peripheral blood chimerism, 90% donor chimerism was also observed in bone marrow HSCs 4 months post-transplantation in CD45-SAP conditioned animals (FIG. 17A). Time course assessment revealed peripheral chimerism was stable and reached 93-94% at 15 months for both donor cell types (FIGS. 16D and 17B). Peripheral blood analysis of the graft 8 months post-transplantation revealed normal distribution of the myeloid, B- and T-cell lineages, indicative of true non-biased, stem cell engraftment (FIG. 16E) that was further confirmed by serial transplantation into lethally irradiated secondary recipients (FIG. 17C). CD45-SAP conditioning also enabled engraftment of purified stem cells as injection of 2,000 LKS CD34−CD150+ or LKS CD48−CD150+ HSCs yielded 60% chimerism at four months (FIG. 16F), whereas non-conditioned control animals failed to demonstrate meaningful engraftment (0-0.03% chimerism).

To compare CD45-SAP with other conditioning methods, further investigations were conducted comparing conventional TBI and experimental CD117− antagonist antibody-based conditioning using the ACK2 monoclonal antibody clone. As shown in FIG. 17D, the chimerism achieved 4 months post-transplantation by CD45-SAP in wild type mice matched 5Gy TBI (50% of lethal TBI dose) conditioning. ACK2-conditioning failed to enable significant engraftment (<3% engraftment) in this immunocompetent background. Injection of one-tenth the cell dose (one million bone marrow cells) confirmed CD45-SAP and 5Gy TBI achieve equivalent engraftment (approximately 20% chimerism) at this lower cell dose with significant synergy (approximately 90% chimerism) when the conditioning methods were combined (FIG. 17E).

Example 6

Figure 18A:
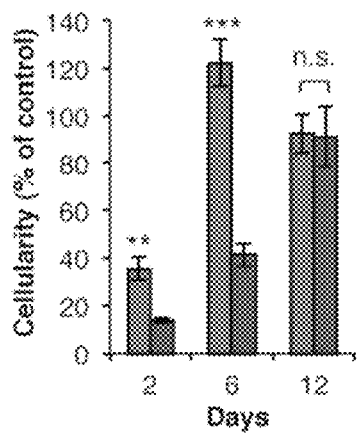
FIGS. 18A-18D depict the differential effects of CD45-SAP versus irradiation on bone marrow.
Figure 18B:
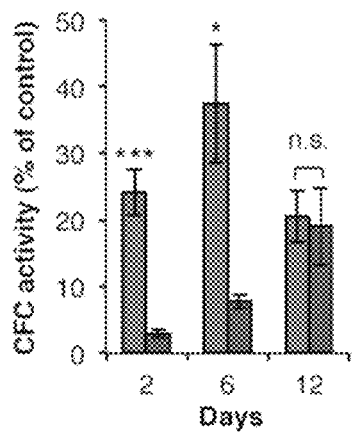
Figure 18C:
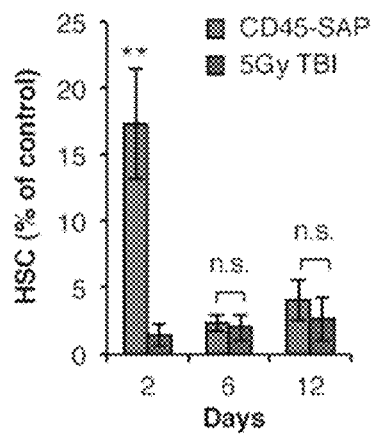

As CD45-SAP and 5Gy TBI yielded equivalent levels of chimerism, the present inventors determined the inherent toxicities of these two conditioning approaches by measuring various blood and bone marrow parameters in conditioned mice that did not undergo post-conditioning transplantation. Both CD45-SAP and 5Gy TBI were non-myeloablative as they permitted long-term survival (>6 months) without stem cell transplantation (n=12 mice/group, data not shown). Time course assessment post-conditioning revealed CD45-SAP had significantly less adverse immediate effects on bone marrow cellularity (FIG. 18A) with quicker recovery to normal levels than irradiation (6 vs. 12 days for CD45-SAP vs. irradiation, respectively). Similarly, the effect of CD45-SAP on bone marrow progenitor cells was less profound than that exerted by irradiation as measured by vitro colony forming cell (CFC) activity assays (FIG. 18B). Despite the overall reduced toxicity of CD45-SAP towards bone marrow cellularity and short-term progenitors, CD45-SAP depleted HSCs as efficiently as irradiation (about 98% depletion, FIG. 18C), although HSC depletion by irradiation was more immediate.

Figure 18D:
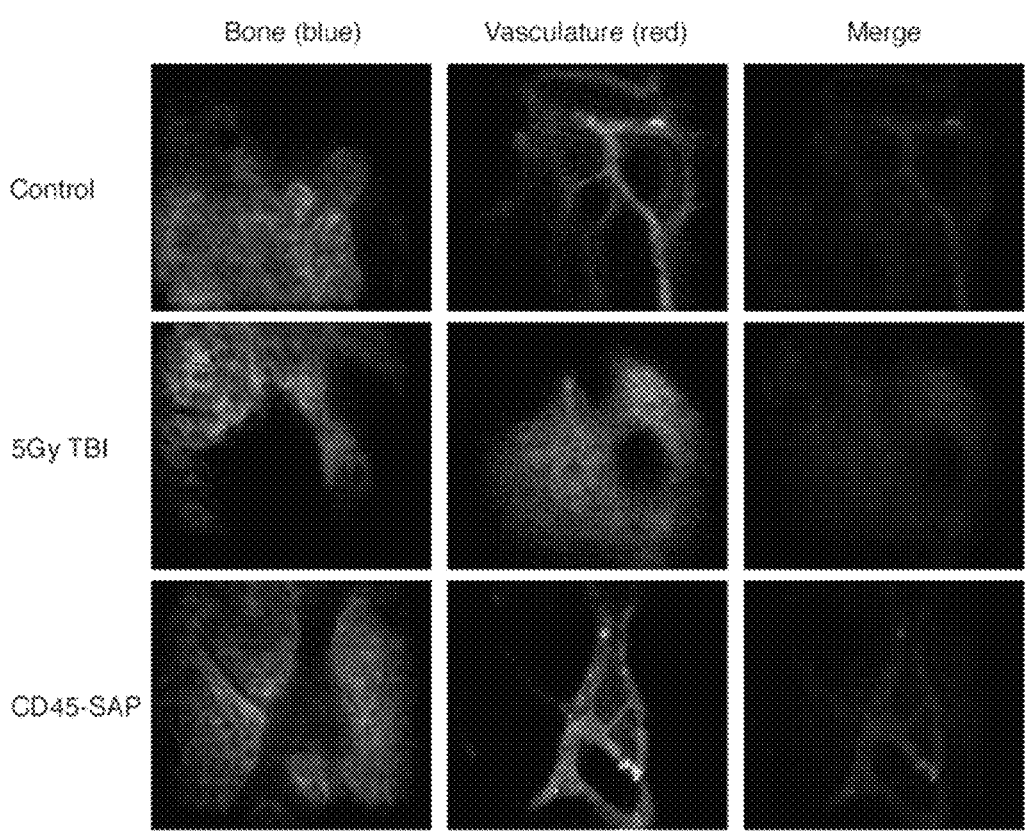
Figure 19:
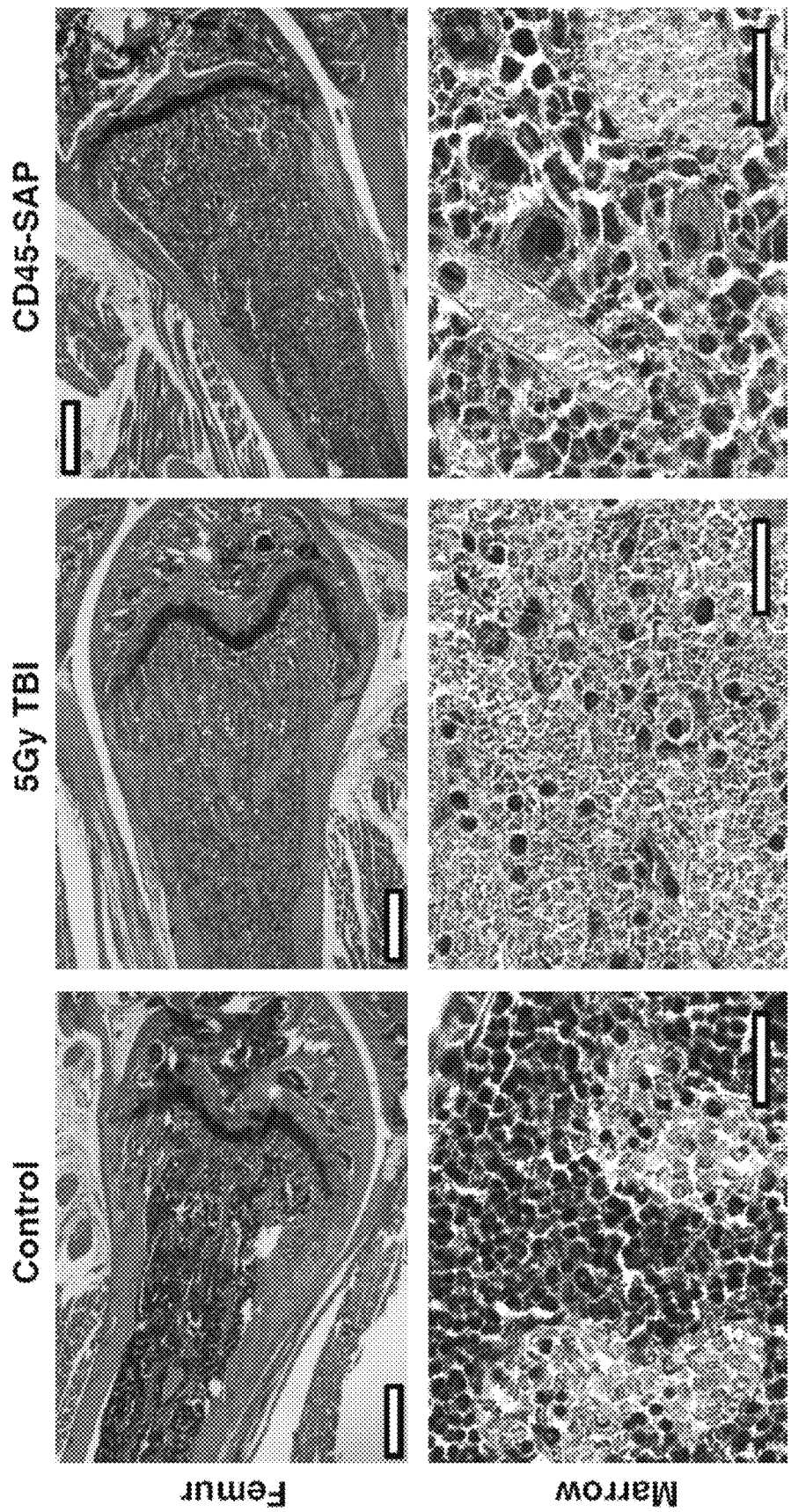
FIG. 19 shows the effects of CD45-SAP and irradiation on bone marrow histology. Representative hematoxylin and eosin staining of femur marrow of control, CD45-SAP or 5Gy TBI conditioned mice 2 days post-conditioning. Scale bars in top and bottom images represent 500 and 20 microns, respectively.

Femur histology performed 2 days post-conditioning suggested CD45-SAP not only preserves bone marrow cellularity to a greater extent than irradiation, but also maintains vascular integrity within the marrow, as RBCs remained within blood vessels, similar to untreated control mice (FIG. 19). In contrast, 5Gy irradiated mice exhibited lower levels of nucleated cells within the marrow with dispersion of red blood cells throughout, indicating gross-disruption of the vasculature. To confirm these differences, the inventors performed a functional assay to assess vascular integrity. High molecular weight (2 MDa) rhodamine-dextran was injected intravenously 2 days post-conditioning and intravital imaging of the calvarium bone marrow was performed. As shown in FIG. 18D, rhodamine-dextran was effectively retained within the blood vessels of mice conditioned with CD45-SAP (similar to unconditioned control), suggesting maintenance of vascular integrity. Irradiated recipients, however, exhibited diffuse dextran throughout the marrow, indicative of compromised vascular integrity.

Together, these results indicate CD45-SAP is less detrimental to bone marrow cellularity, hematopoietic progenitors and vascular integrity than 5Gy irradiation while achieving efficient HSC depletion and allowing comparable levels of engraftment.

Example 7

Figure 20A:
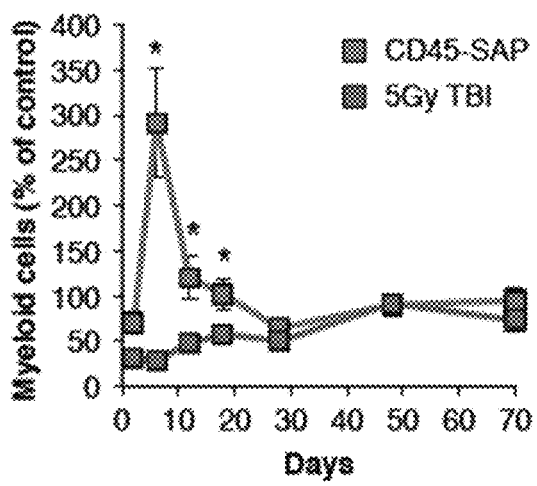
FIGS. 20A-20E show the differential effects of CD45-SAP versus irradiation on blood and thymus.
Figure 20B:
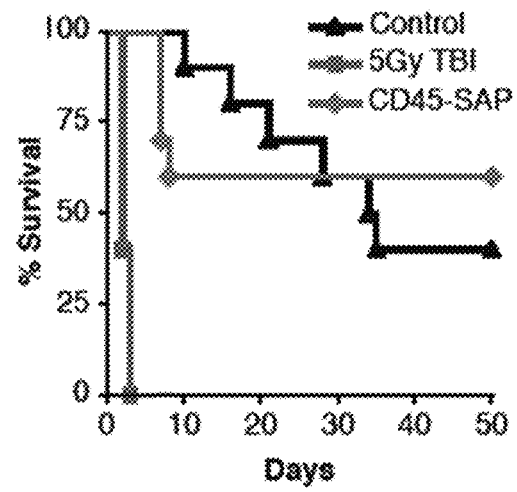

Adaptive and innate immunity recovery is of paramount importance for survival after HSCT and its failure post-conditioning contributes to the morbidity and mortality associated with transplantation. Analysis of the peripheral blood following conditioning (without transplantation) revealed significant differences between CD45-SAP and 5Gy TBI conditioning. In contrast to irradiation, which suppressed myeloid (Mac1+, Gr1+) cells for 28 days, CD45-SAP conditioned mice showed an immediate and sizable increase (3-fold) in circulating myeloid cells that returned to normal levels at 12 days (FIG. 20A). To test innate immunity, conditioned mice were challenged with a systemic infection of *Candida albicans* (2-days post-conditioning), a clinically relevant fungal strain that infects immunocompromised HSCT patients post-conditioning. Mice conditioned with 5Gy TBI were highly susceptible to *Candida* challenge with 100% lethality occurring within 3 days post-infection, (FIG. 20B, p value vs. control <0.0001). In contrast, mice conditioned with CD45-SAP were considerably more resilient (p value vs. irradiation <0.0002) with overall survival over 50 days similar to naïve control (p value of control vs. CD45-SAP=0.57).

Figure 20C:
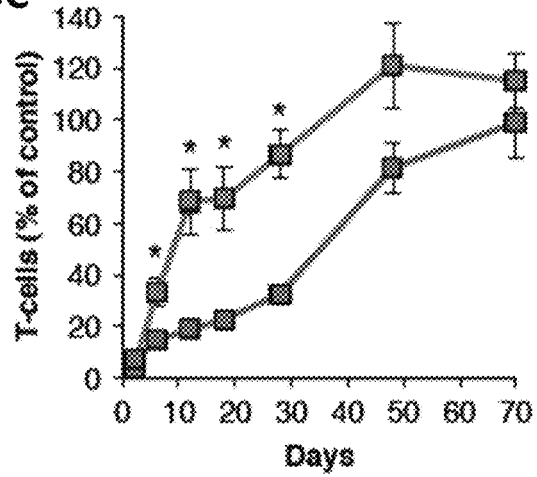
Figure 20D:
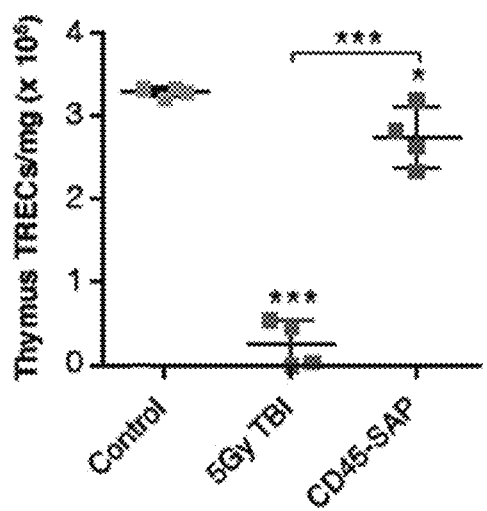
Figure 20E:
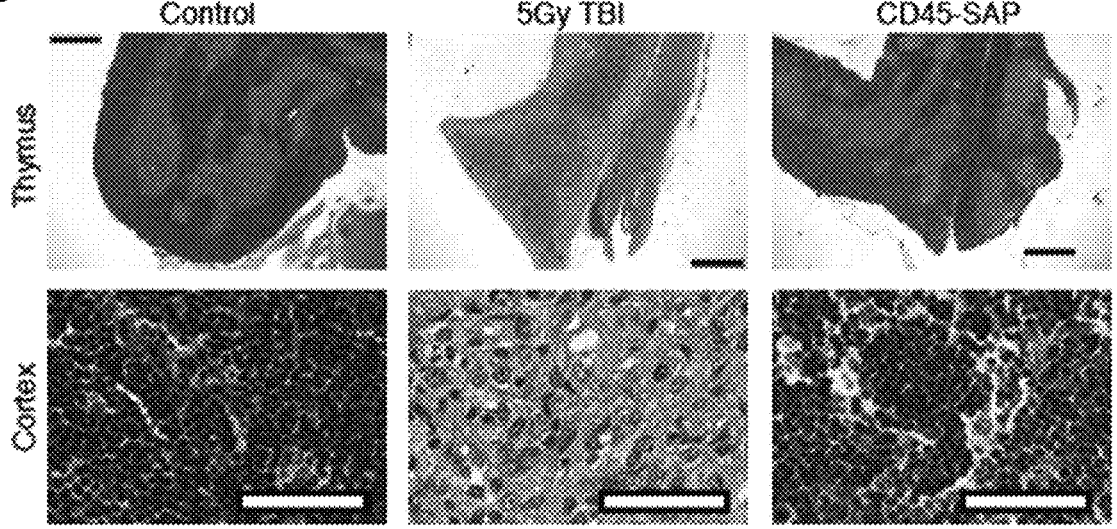
Figures 21A, 21B, 21C, 21D, 21E, 21F, 21G:
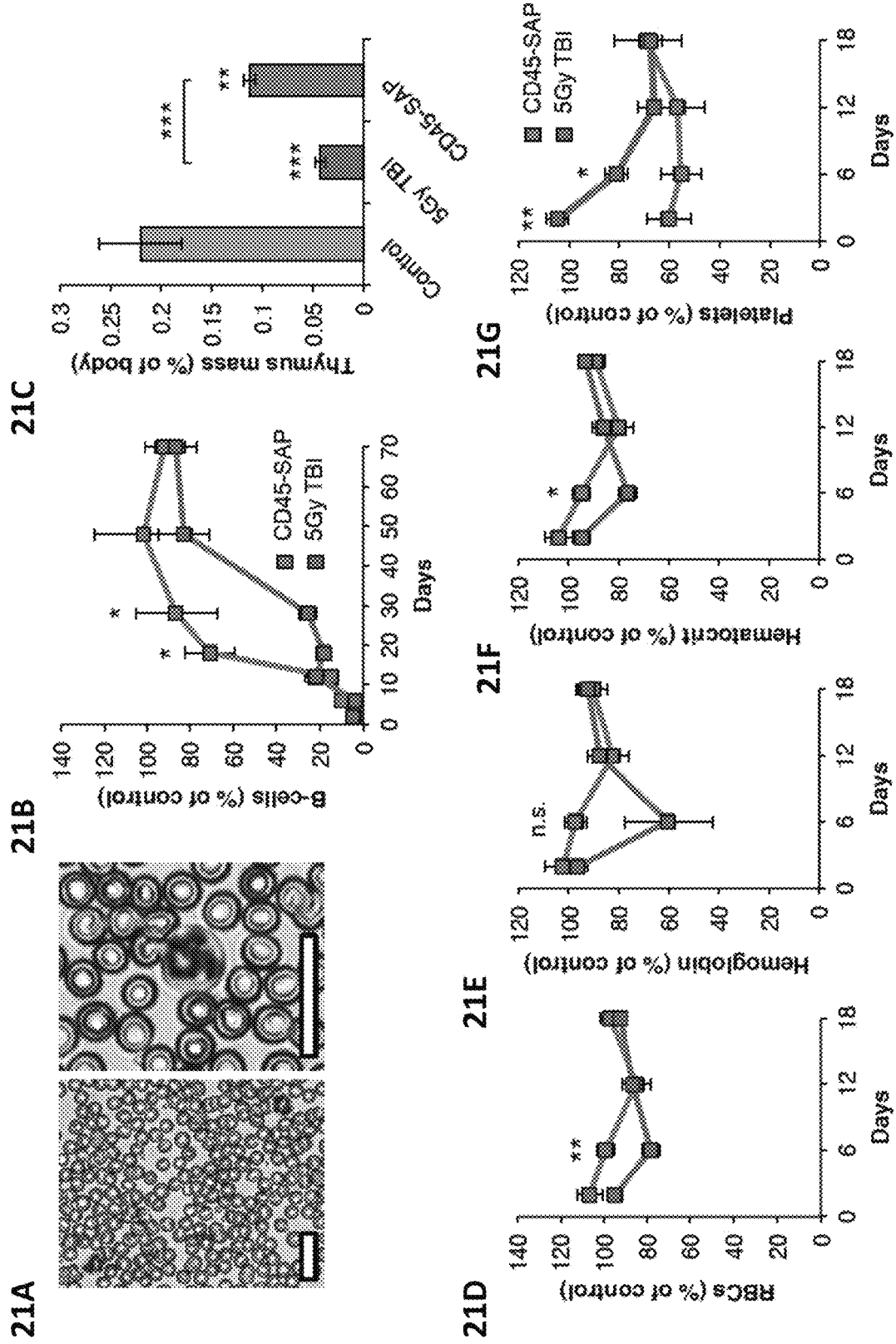
FIGS. 21A-21G depict the effects of CD45-SAP and irradiation on blood and thymus.

Both B- and T-cells were equally and potently depleted 2 days post-conditioning by CD45-SAP and 5Gy (FIGS. 20C and 21B). However, recovery of lymphocytes was considerably more rapid in CD45-SAP treated mice. B-cells recovered to 80% within 18 days (FIG. 21B), and T-cells recovered to 70% within 12 days (FIG. 20C). In contrast, irradiated mice required a striking extra 30-36 days for B- and T-cells to recover to comparable levels (FIGS. 20C and 21B). The faster T-cell recovery observed post CD45-SAP may be due to differential effects on the thymus, an organ critical for the generation of new T-cells that is known to be damaged by TBI-conditioning. Histology of thymi 2 days post-conditioning demonstrated that irradiation induced visible thymic atrophy with considerable reduction of thymocyte cellularity in the cortex; whereas no thymic atrophy was evident following CD45-SAP (FIG. 20D). The inventors tested preservation of thymic function by measuring the presence of T-cell receptor excision circles (TRECs), the molecular signature of T cell receptor rearrangement that does not replicate with genomic DNA and therefore marks newly generated T cells. Quantification of TRECs per mg of thymus tissue 3 days post-conditioning (FIG. 20E) revealed de novo T-cell output following CD45-SAP treatment was 84% of normal (p value vs. control=0.025) whereas 5Gy TBI decreased T-cell output to 8% (p value vs. control <0.0001). Irradiation also reduced thymic mass by 80% whereas CD45-SAP decreased thymic mass by 50% (FIG. 21C).

CD45-SAP did not induce anemia, as red blood cell, hematocrit and hemoglobin levels remained normal, whereas irradiation induced mild anemia 6 days post-conditioning (FIGS. 21D-21F). Platelets were mildly affected by both conditioning regimens with a decrease to 40% of normal levels (FIG. 21G). No observable toxicity was observed in the gastrointestinal tract, liver and ovaries for either CD45-SAP or irradiation as assessed by necropsy and histology (data not shown).

Taken together, the foregoing results suggest CD45-SAP conditioning preserves myeloid innate immunity, avoids anemia and facilitates rapid B- and T-lymphocyte recovery versus the equivalent conditioning-dose of irradiation.

Example 8

To investigate whether CD45-SAP conditioning could enable curative transplantation in a relevant non-malignant hemoglobinopathy model, the present investigators used knock-in mice bearing the human sickle hemoglobin gene which mimic human sickle cell disease. These mice exhibit decreased red blood cell counts, hematocrit and hemoglobin levels with elevated numbers of immature red blood (reticulocytes) and abnormally large spleens. Previous transplantation studies in sickle mice have shown 25% myeloid chimerism returns blood parameters to 90% of normal, while 70% myeloid chimerism is needed to completely correct organ pathophysiology.

Figures 22A, 22B, 22C, 22D, 22E, 22F:
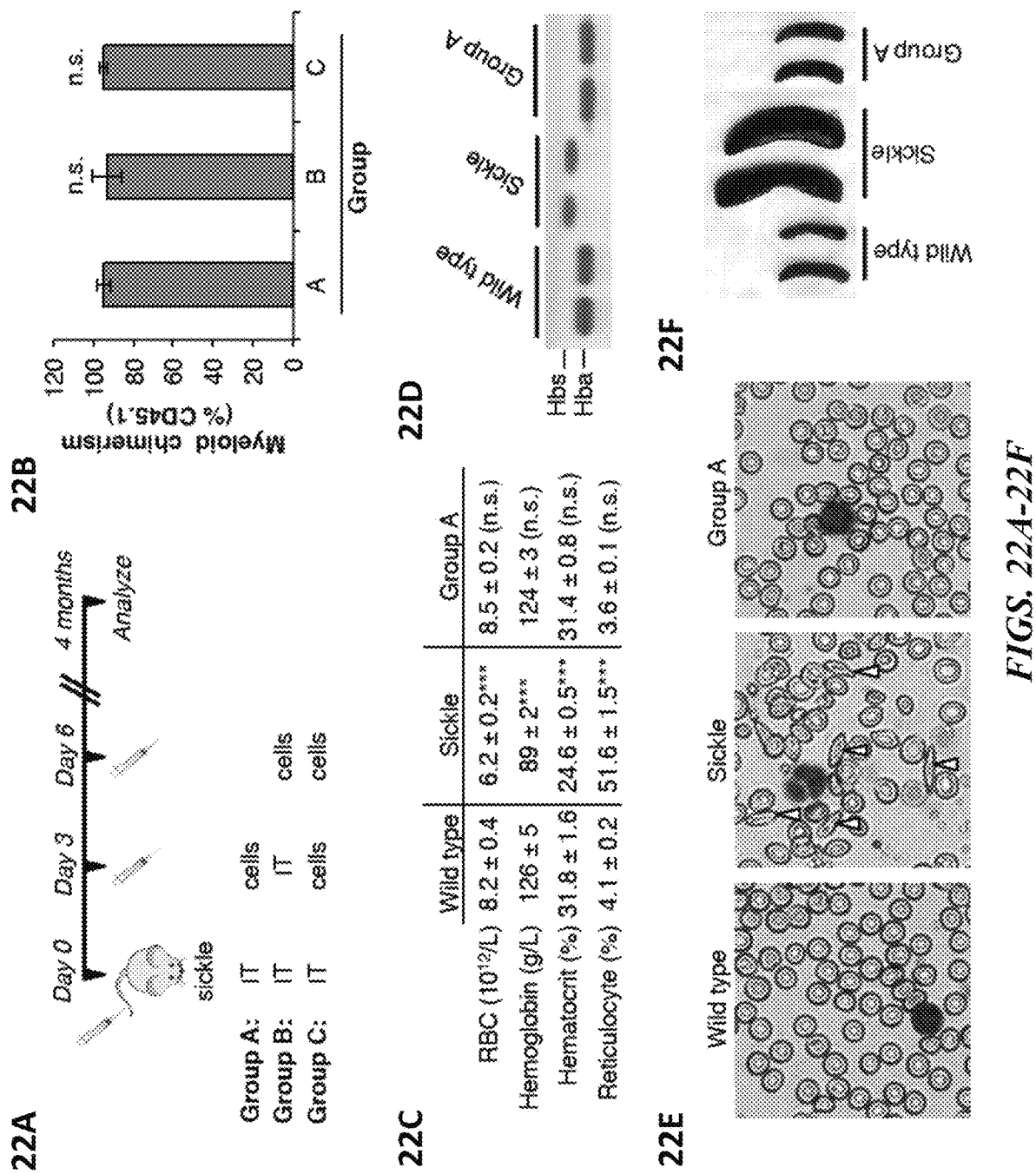
FIGS. 22A-22F demonstrate the correction of sickle cell disease.
Figures 23A, 23B, 23C, 23D, 23E, 23F:
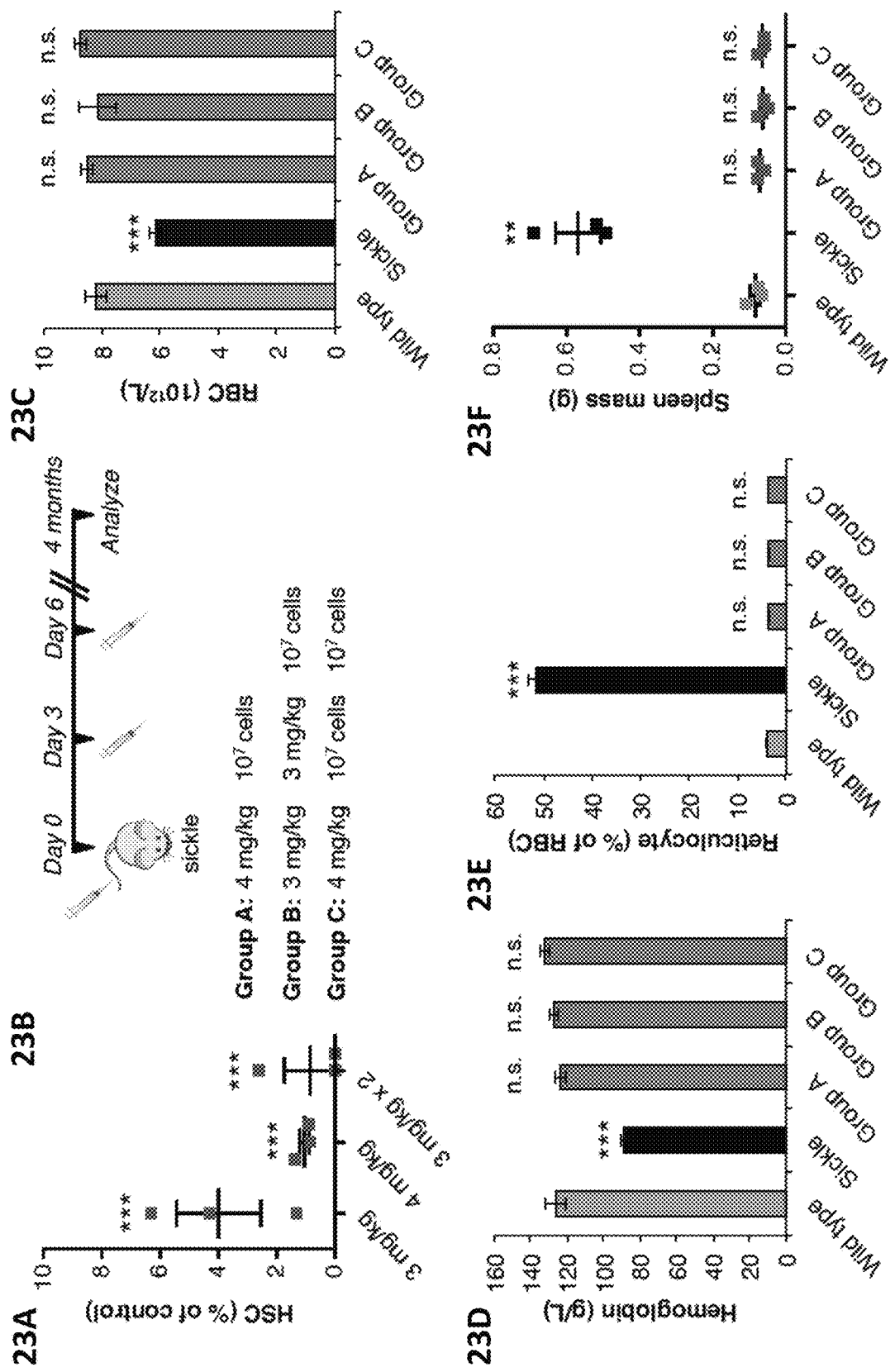
FIGS. 23A-23F demonstrate sickle cell disease correction by HSCT post CD45-SAP conditioning.

As sickle mice have elevated WBC levels (versus wild-type), the present inventors re-optimized the dose of CD45-SAP and determined a single dose of 4 mg/kg or 2 sequential doses of 3 mg/kg CD45-SAP achieved maximal stem cell depletion (≈99% depletion, FIG. 23A). Based on these doses, 3 transplantation protocols were investigated (groups A-C) as outlined by in FIGS. 22A and 23B (6 mice/group). All 3 groups (18/18 mice) conditioned with CD45-SAP and transplanted with wild-type cells demonstrated >90% donor myeloid chimerism at 4 months post-transplantation (FIG. 22B). A complete normalization of red blood cell, hemoglobin, hematocrit and reticulocyte levels was also achieved post-transplantation (FIGS. 22C and 23C-E).

Sickle hemoglobin protein in the blood was completely replaced with normal hemoglobin protein as assessed by native-PAGE analysis (FIG. 22D). In addition, blood smears showed a lack of sickle-shaped red blood cells versus sickle control (FIG. 22E) and spleen sizes were also returned to normal (FIGS. 22F and 23F). CD45-SAP conditioning, therefore, achieves >90% myeloid chimerism with full disease correction of sickle cell anemia post-transplantation.

Example 9

Figure 24:
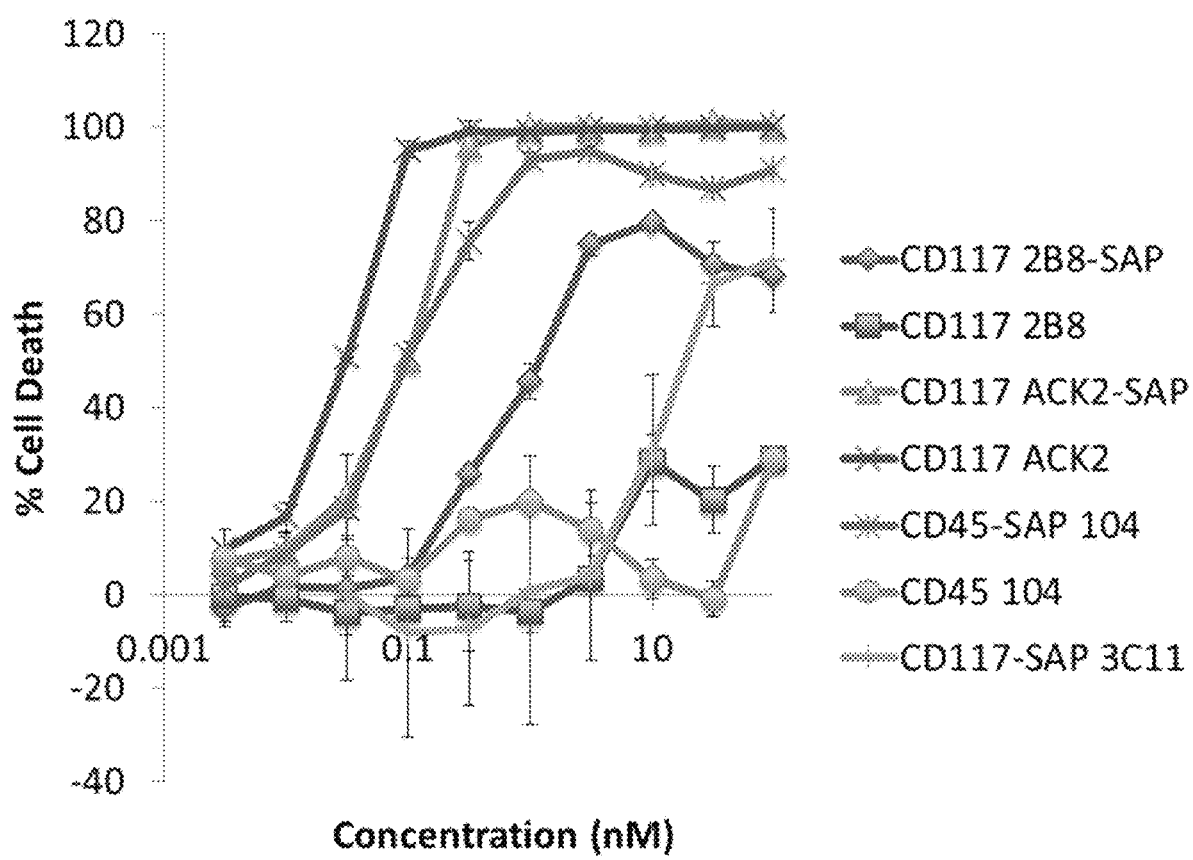
FIG. 24 illustrates the in vitro killing of various antibody and antibody-immunotoxin conjugates, including 2B8-SAP, against EML progenitor cell line. As illustrated, the 2B8 (CD117) and 104 (CD45) antibodies are inactive unless combined with saporin to create an internalizing antibody-toxin conjugate. In addition the ACK2 (CD117) antibody demonstrated intrinsic cell depletion activity without saporin due to antagonizing the stem cell factor (SCF)-CD117 interaction. Cells that require SCF are sensitive to antagonism.

The present inventors performed a viability assay to demonstrate the activity of various antibodies and antibody-saporin conjugates targeting the CD45 and CD117 markers. ACK2 is an antagonist monoclonal antibody clone to mCD117, which inhibits stem cell factor 1 (SCF) binding to the receptor. 2B8 is a non-antagonist monoclonal antibody clone to mCD117, which unlike ACK2 does not inhibit SCF binding. An MTS assay was performed by treating EML progenitor cell line with varying concentrations of the antibodies alone or coupled to saporin. Cells were grown in media containing 200 ng/ml SCF, and viability was assessed at 72 hours post treatment. 10 uM Staurosporine used as a 100% death control. As illustrated in FIG. 24, the 2B8-saporin conjugate demonstrated killing of EML progenitor cell line in vitro. In contrast, the 2B8 (CD117) and 104 (CD45) antibodies were inactive unless combined with saporin to create an internalizing antibody-toxin conjugate. In addition the ACK2 (CD117) antibody demonstrated intrinsic cell depletion activity without saporin due to antagonism of the SCF-CD117 interaction. Cells that require SCF are sensitive to antagonism.

Figure 25A:
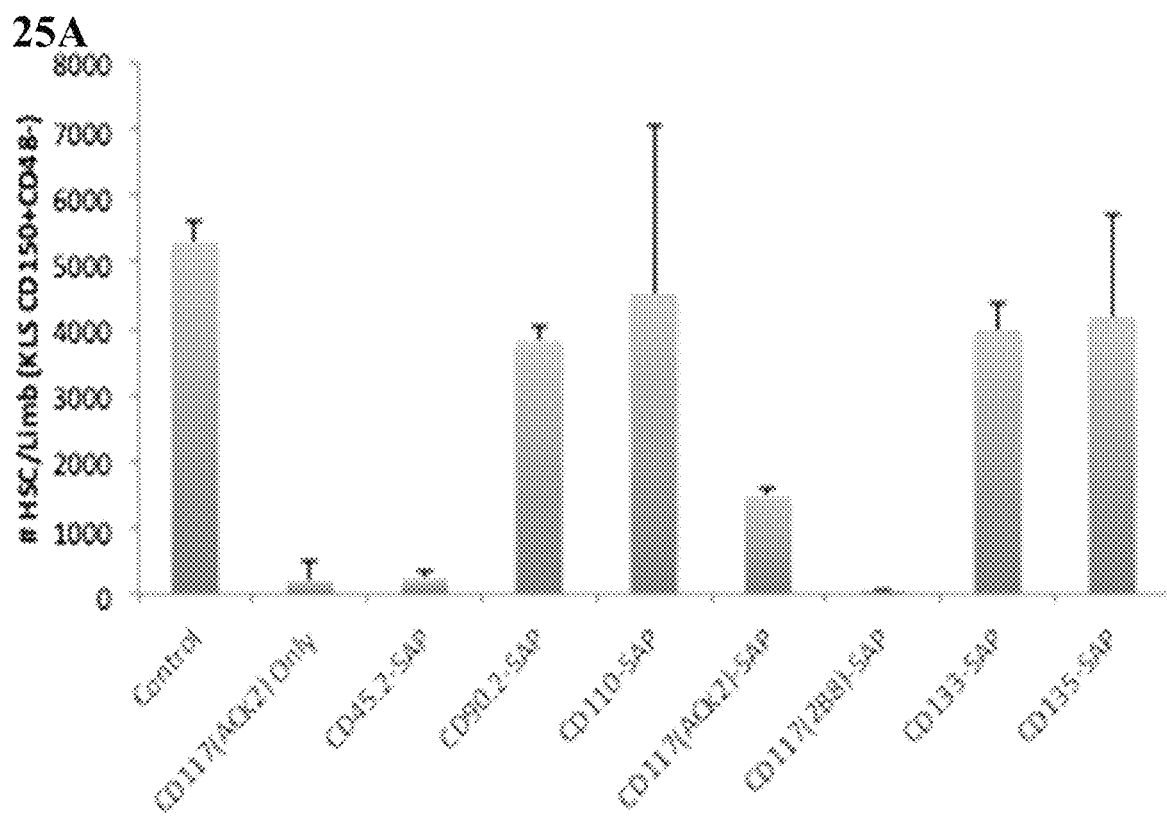
FIGS. 25A and 25B depict the results of a saporin pilot study where various monoclonal antibodies to known antigens on HSC were evaluated.
Figure 25B:
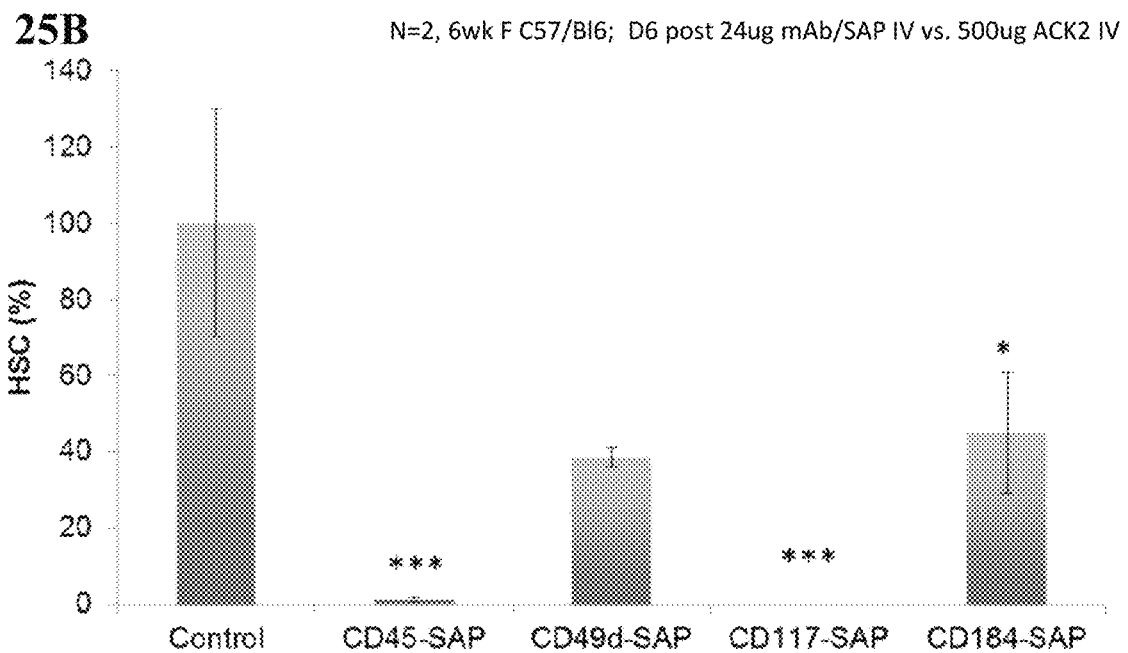
Figure 26:
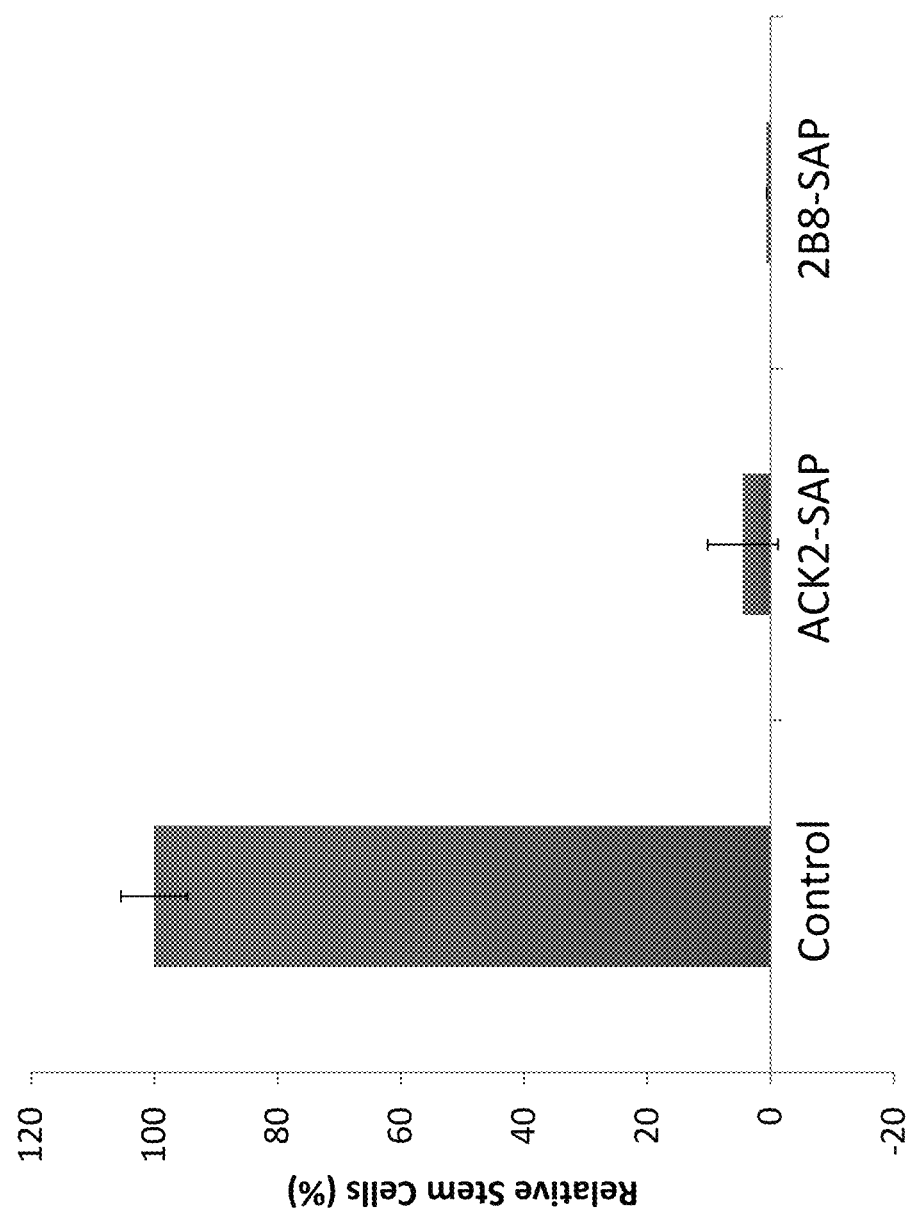
FIG. 26 shows stem cell depletion of both ACK2-SAP and 2B8-SAP antibodies and, as illustrated, both achieve phenotypic HSC depletion, however only 2B8-SAP enables engraftment.
Figure 28:
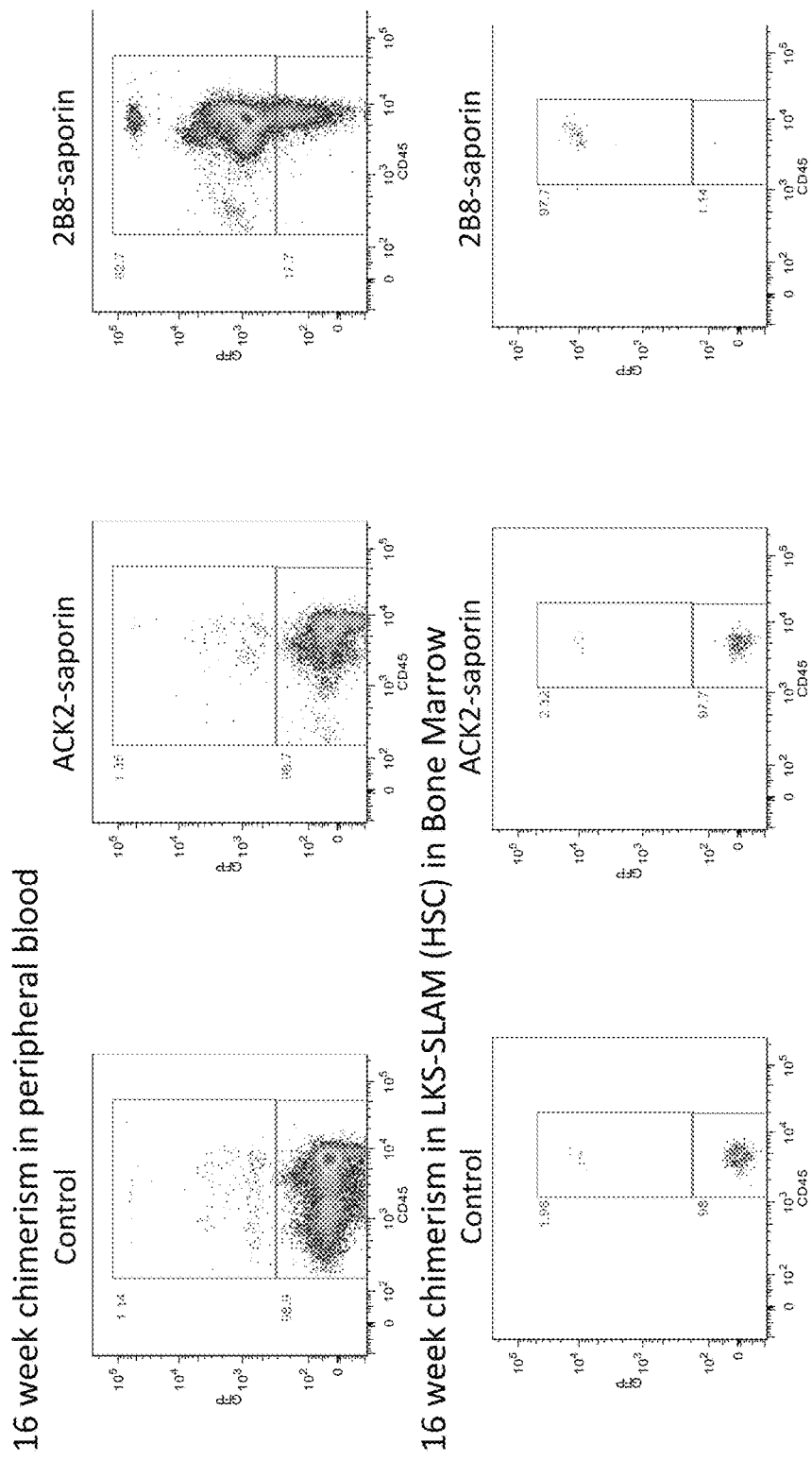
FIG. 28 shows the results of a 16-week pilot engraftment study in peripheral blood and in LKS-SLAM (HSC) in bone marrow. 10 million whole bone marrow GFP cells were transplanted 8 days post antibody-toxin conjugate administration and chimerism was assessed 16 weeks post transplantation in blood cells and bone marrow HSCs. As illustrated, the CD117 ACK2-SAP conjugate failed to enable engraftment whereas the CD117 2B8-SAP conjugate enabled efficient engraftment (80-98%) of GFP donor cells.

Further studies were conducted to evaluate various monoclonal antibodies directed to known antigens on HSC. As illustrated in FIGS. 25A and 25B, some antibodies produced a very high HSC depletion (e.g., antibodies targeting the CD45, CD117, CD49d and CD184 markers), while several others had high toxicity (e.g., CD34, CD93, CD201 and ESAM). Although both ACK2-SAP and 2B8-SAP achieved phenotypic HSC depletion as shown in FIG. 26, only 2B8-SAP enabled engraftment (FIGS. 27 and 28). As shown in FIG. 27, ACK2-SAP is better than ACK2 only, but 2B8-SAP is considerably more efficient than either, and comparable to CD45-SAP.

Next, following the transplant of 10 million whole bone marrow GFP cells 8 days post antibody-toxin conjugate administration, chimerism was assessed (16 weeks post transplantation) in blood cells and bone marrow HSCs. As illustrated, in FIG. 28 the CD117 ACK2-SAP conjugate failed to enable engraftment whereas the CD117 2B8-SAP conjugate enabled efficient engraftment (80-98%) of GFP donor cells.

Example 10

Figure 29:
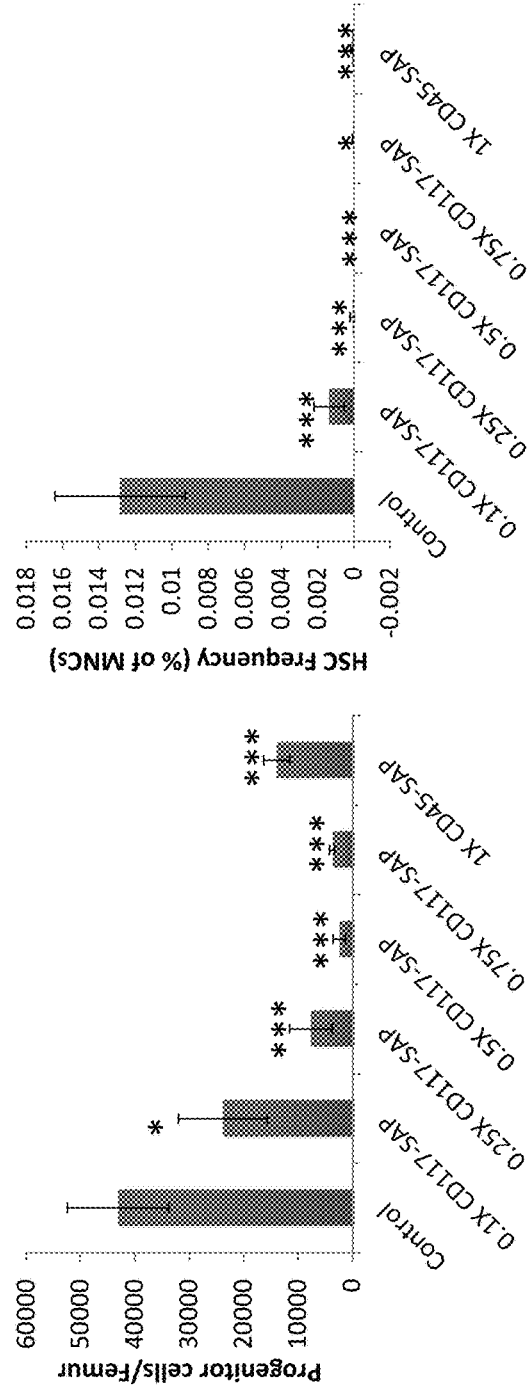
FIG. 29 depicts the results of an in vivo 2B8-SAP does optimization study (n=4 mice per group) 8 days post administration.

An in vivo CD117 2B8-SAP dose optimization study (n=4 mice per group) was performed by intravenously administering 2B8-SAP to nine week C57/Bl6 female mice. Mice were administered 2B8-SAP and stem cell depletion was assessed 8 Days post administration. As illustrated in FIG. 29, no obvious toxicity was observed at 0.1-0.5× doses, while 2/4 deaths were observed at 0.75× dose and 4/4 deaths were observed at 1.0× dose.

Figure 30:
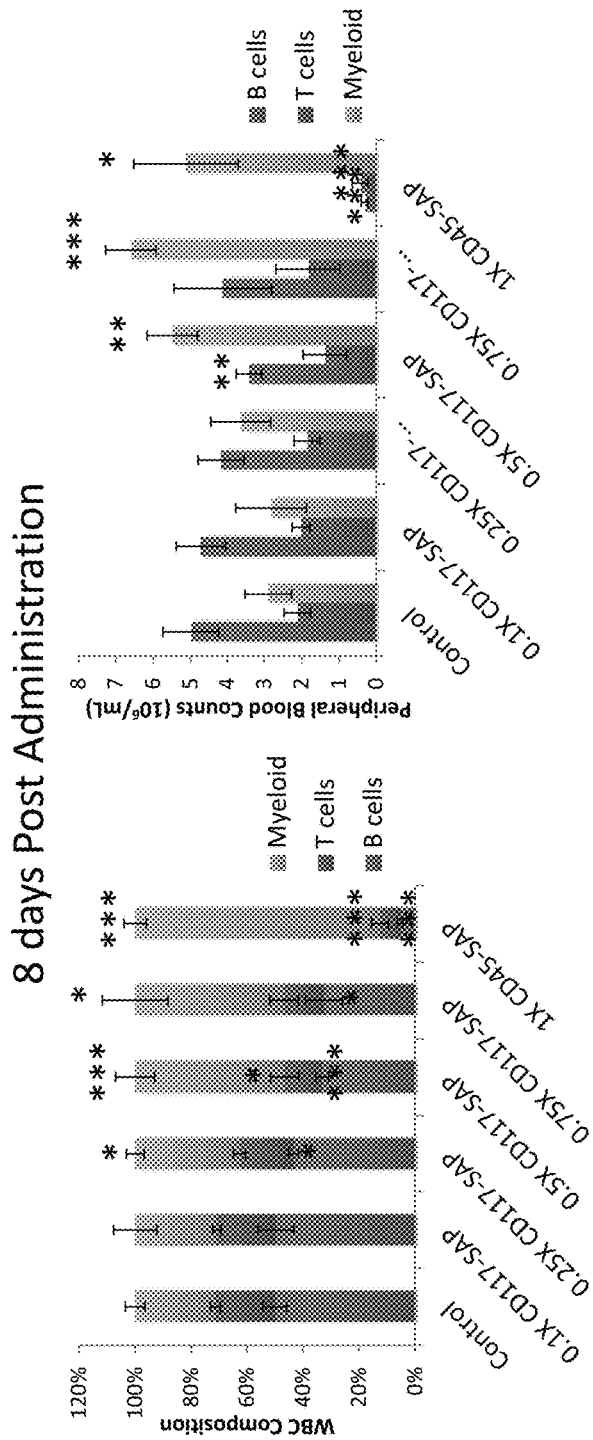
FIG. 30 illustrates that the 2B8-SAP conjugate leaves peripheral blood intact, confirming that 2B8-SAP is non-myeloablative and non-lymphoablative, as determined 8 days post-administration. As shown, the CD45-SAP conjugate depletes B- and T-cells, whereas the 2B8-SAP conjugate does not deplete B- and T-cells.

As shown in FIG. 30, 2B8-SAP leaves peripheral blood intact and is thus non-myeloablative and non-lymphoablative 8 days post-administration. As also illustrated in FIG. 30, an expansion of the myeloid compartment was observed and, in contrast to a CD45-SAP which depletes B- and T-cells, 2B8-SAP surprising does not deplete B- and T-cells. Thus, clone 2B8 based CD117-saporin avoids T-cell and B-cell depletion, suggesting innate immunity is preserved. No RBC loss-relevant to anemic diseases was observed.

Example 11

Figure 31:
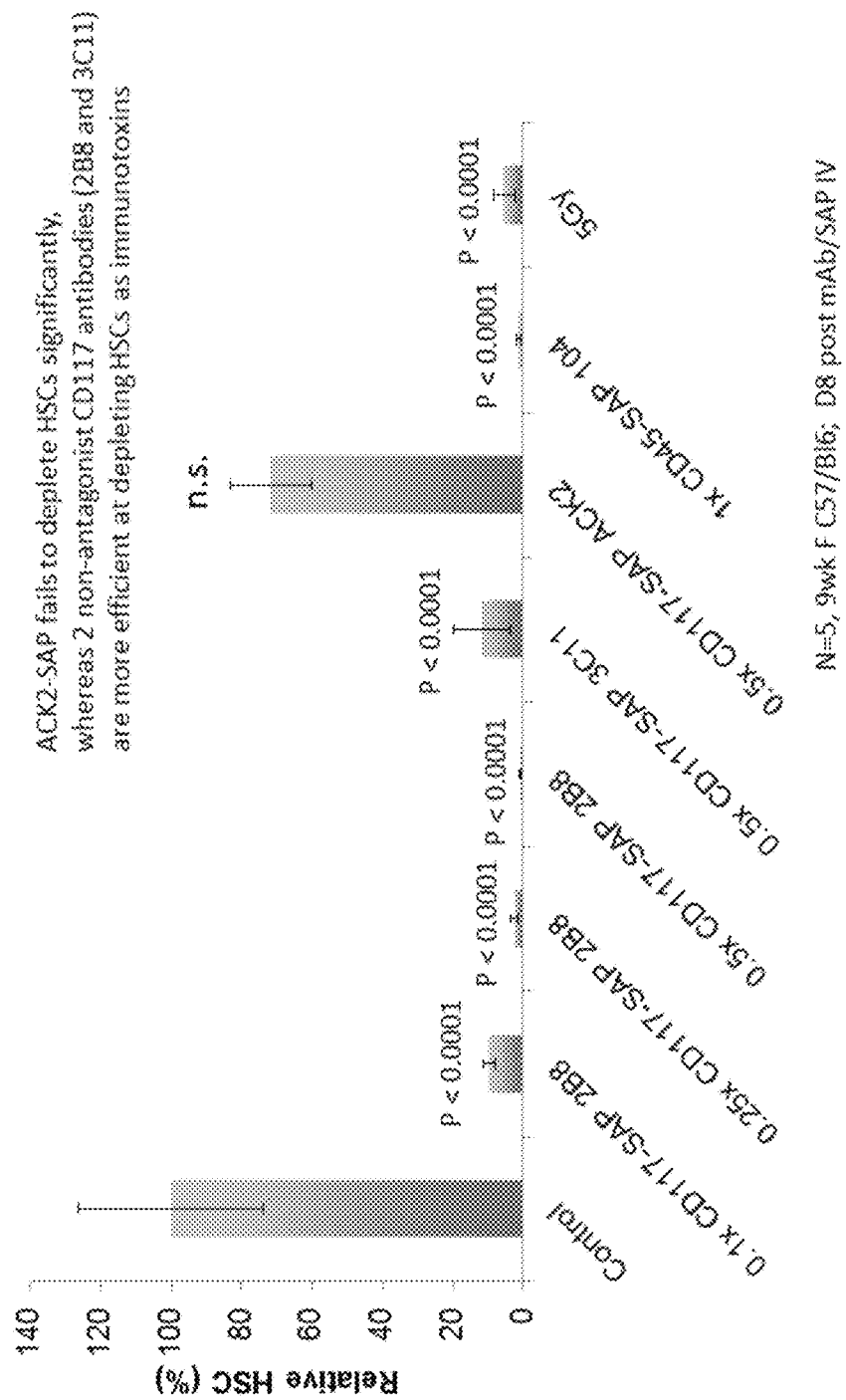
FIG. 31 compares the in vivo efficacy of various CD117-SAP clones in bone marrow tissue relative to a CD45-SAP clone and 5Gy total body irradiation (n=5 mice per group). The number of stem cells in the bone marrow tissue of the subject animals was assessed 8 days post-administration of the antibody-toxin conjugate. As illustrated, the ACK2-SAP conjugate failed to deplete HSCs significantly, whereas two non-antagonist CD117 antibody-toxin conjugates (2B8-SAP and 3C11-SAP) are more efficient at depleting HSCs as immunotoxins.

The inventors sought to compare the activity of various CD117-SAP clones in vivo relative to a CD45-SAP clone and 5Gy total body irradiation (n=5 mice per group). The selected CD117-SAP conjugate was intravenously administered to nine week C57/Bl6 female mice and the number of stem cells in the bone marrow tissue of the subject animals was assessed 8 days post-administration of the antibody-toxin conjugate. As illustrated in FIG. 31, the ACK2-SAP conjugate failed to deplete HSCs significantly, whereas two non-antagonist CD117 antibody-toxin conjugates (2B8-SAP and 3C11-SAP) are more efficient at depleting HSCs as immunotoxins.

Figure 32:
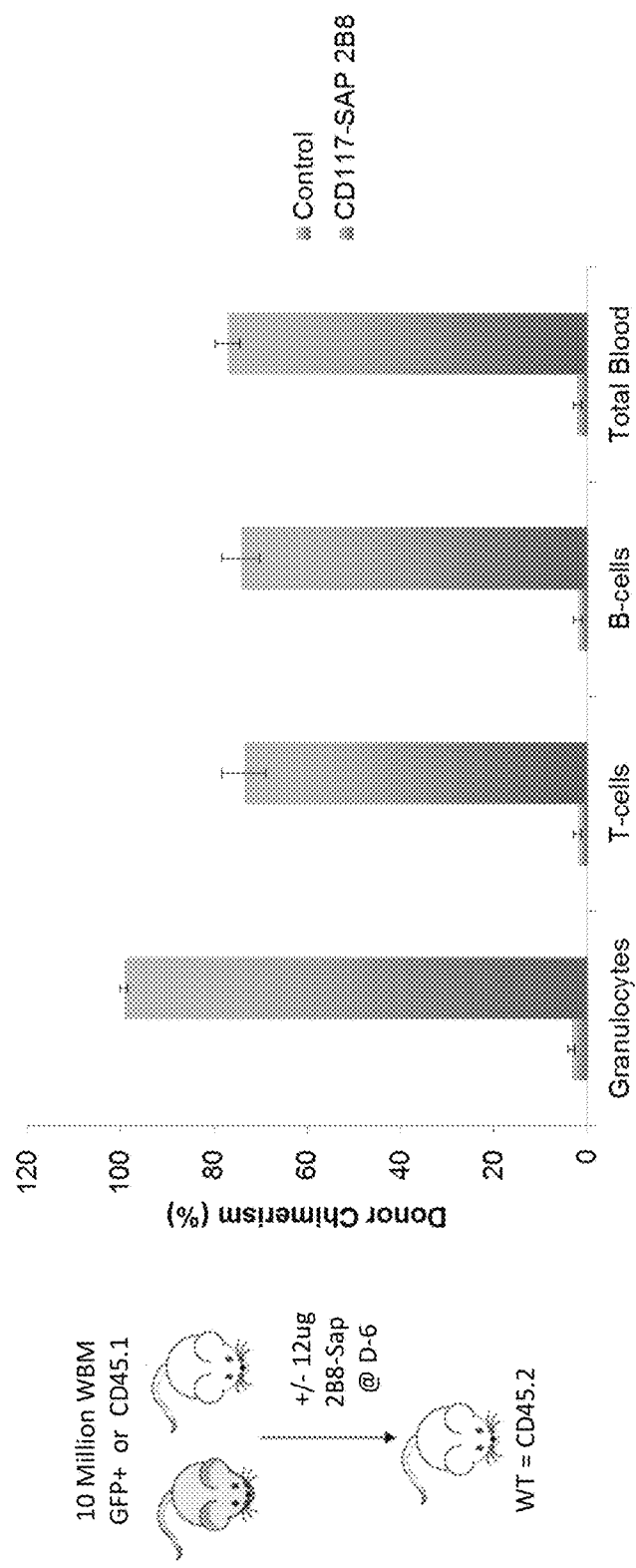
FIG. 32 depicts the results of a 16 week engraftment study (n=5 mice per group) performed using the CD117 2B8-SAP conjugate, as depicted. To perform the study, 10 million whole bone marrow CD45.1 cells were transplanted 8 days post-administration of the CD117 SAP-2B8 conjugate and chimerism was assessed 16 weeks post-transplantation.

The inventors next performed a sixteen-week engraftment study (n=5 mice per group) for the CD117 2B8-SAP conjugate in nine week C57/Bl6 female mice, as schematically depicted in FIG. 32. 10 million whole bone marrow CD45.1 cells transplanted 8 days post-administration of the CD117 SAP-2B8 conjugate and chimerism was assessed 16 weeks post-transplantation. Total blood chimerism is 80% donor; donor cells contribute to granulocyte (myeloid), T-cells and B-cells. As shown in FIG. 32, the non-antagonist 2B8-SAP conjugate achieved efficient donor cell engraftment in fully immunocompetent animals, thus greatly expanding the scope of diseases to include non-SCID conditions. The foregoing represents an alternative approach to the treatment of malignant and pre-malignant diseases as well, as in many of those cases the malignancy or pre-malignant cells rely on SCF for growth and likely particularly sensitive to this reagent.

Example 12

Figure 33:
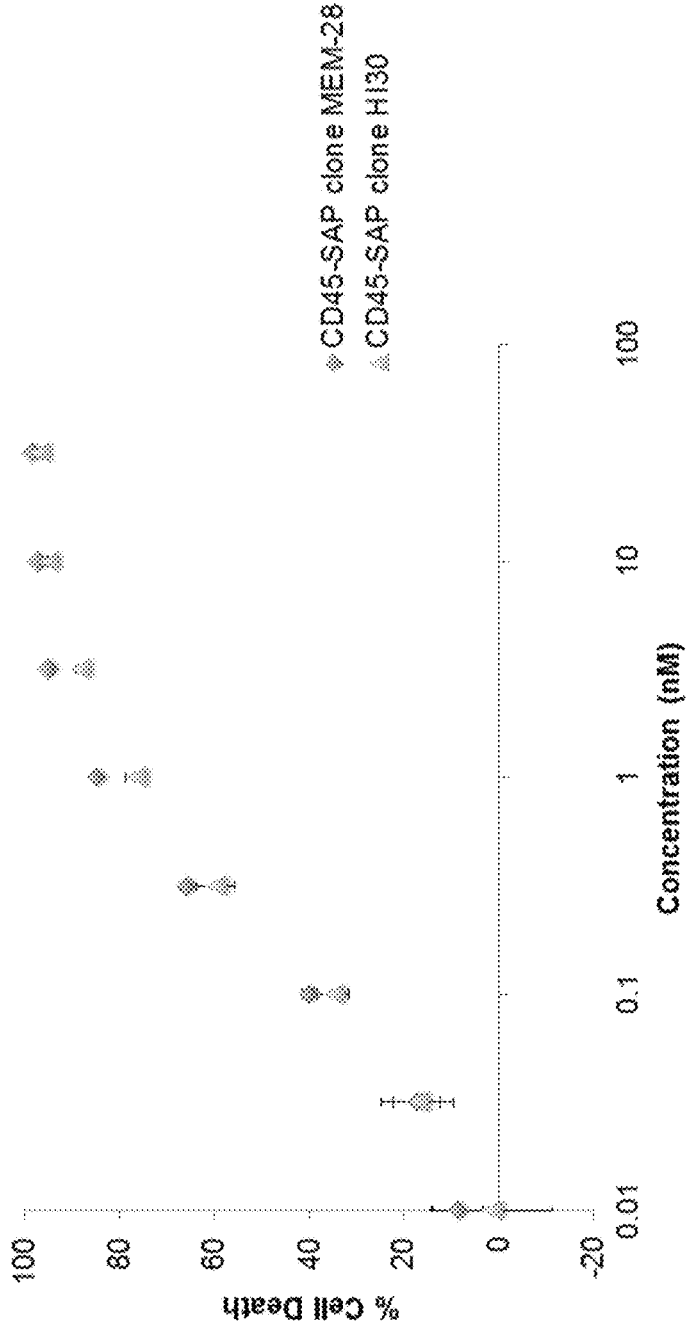
FIG. 33 illustrates the in vitro activity of anti-human CD45-SAP conjugates against human hematopoietic cells. Human Jurkat CD45+ hematopoietic cells were treated in vitro with various concentrations of anti-human CD45-SAP immunotoxins (created using anti-human antibodies) for 72 hours and cell viability was assessed using MTS assay (Promega). As illustrated, $IC_{50}$ values for cell killing are 130 pM and 200 pM for the MEM-28 and HI30 clones, respectively. Data represents mean±SD (n=3 technical replicates) of a representative experiment.

The present inventors next sought to assess the in vitro activity of anti-human CD45-SAP conjugates against human hematopoietic stem cells. CD45-SAP immunotoxins were created from anti-human antibody clones 104, MEM-28 and HI30. Human Jurkat CD45+ hematopoietic cells were treated in vitro with various concentrations of anti-human CD45-SAP immunotoxins for 72 hours and cell viability was assessed using MTS assay (Promega). As illustrated in FIG. 33, $IC_{50}$ values for cell killing were 130 pM and 200 pM for the MEM-28 and HI30 clones, respectively, evidencing that CD45 internalization is not species-specific and that such CD45-SAP conjugates demonstrate efficacy in human hematopoietic cells in vitro.

Figure 34:
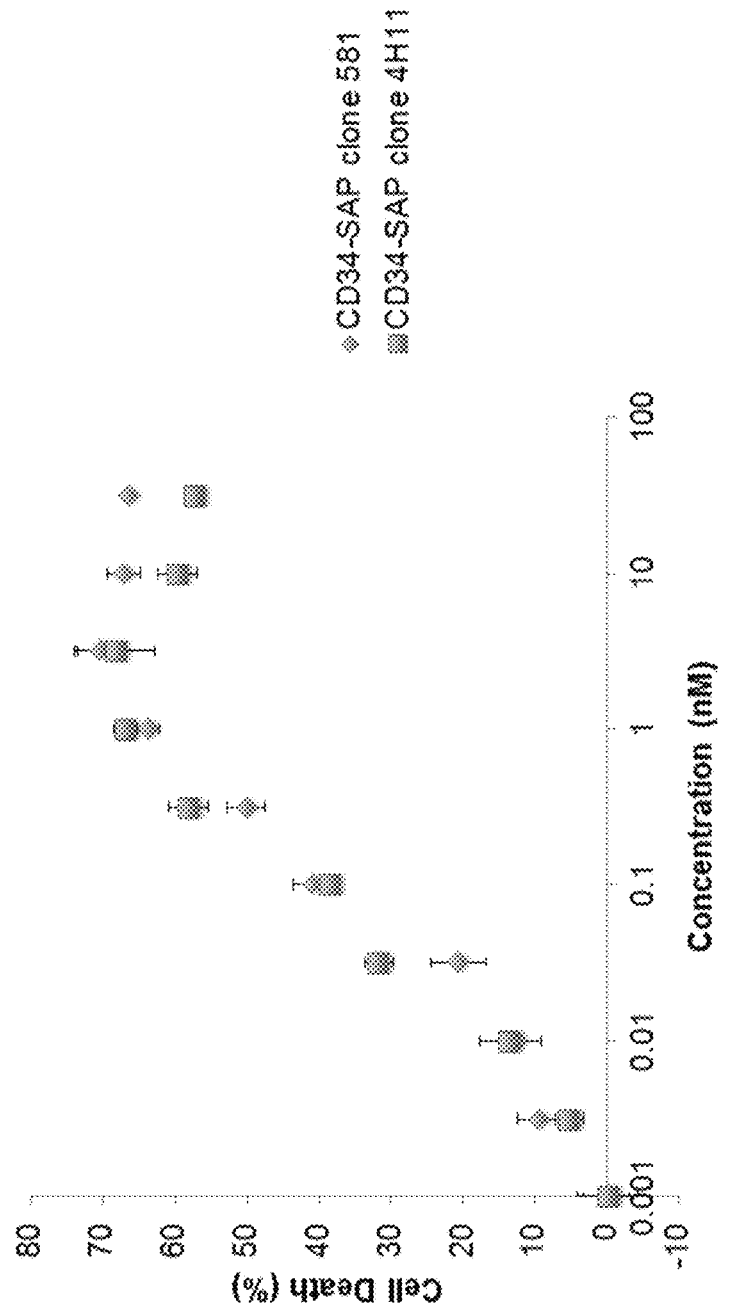
FIG. 34 presents the activity of anti-human CD34-SAP against human hematopoietic stem cells (HSCs) in vitro. Human mobilized peripheral blood CD34+ HSCs were treated in vitro with various concentrations of anti-human CD34-SAP immunotoxins for 96 hours and cell viability was assessed using MTS assay (Promega). As illustrated, $IC_{50}$ value for cell killing is approximately 100 pM for both clones tested.

The activity of the anti-human CD34-SAP conjugate against human hematopoietic stem cells (HSCs) was also assessed in vitro. Human mobilized peripheral blood CD34+ HSCs were treated in vitro with various concentrations of anti-human CD34-SAP immunotoxins for 96 hours and cell viability was assessed using MTS assay (Promega). As illustrated in FIG. 34, the $IC_{50}$ values for cell killing were approximately 100 pM for both the 581 and 4H11 clones tested.

Example 13

Mutant protective antigens (mut-PA) can be fused to ligands or scFv to create chimeras that enable cell-specific forming of cell surface pores that can import lethal factor N-terminus-toxin chimeras (LFN-toxin). Various LFN-toxins can be used, including diptheria toxin (LFN-DTA, LFN-SAP, etc.) The internalization mechanism is intrinsic to PA and LFN and does not require internalizing receptor or internalizing properties of antibody/ligand and is depicted in FIG. 35.

The present inventors sought to demonstrate the activity of LFN-DTA against human hematopoietic stem cells (HSCs) in vitro. Human mobilized peripheral blood CD34+ HSCs were treated in vitro with various concentrations of LFN-DTA immunotoxin in the presence of 10 nM WT-PA for 96 hours and cell viability was assessed using MTS assay (Promega). As illustrated in FIG. 36, 100% cell death was observed at 1 femtomolar concentration of LFN-DTA, demonstrating LFN-DTA can be used to enable potent killing of human HSCs.

Figure 37:
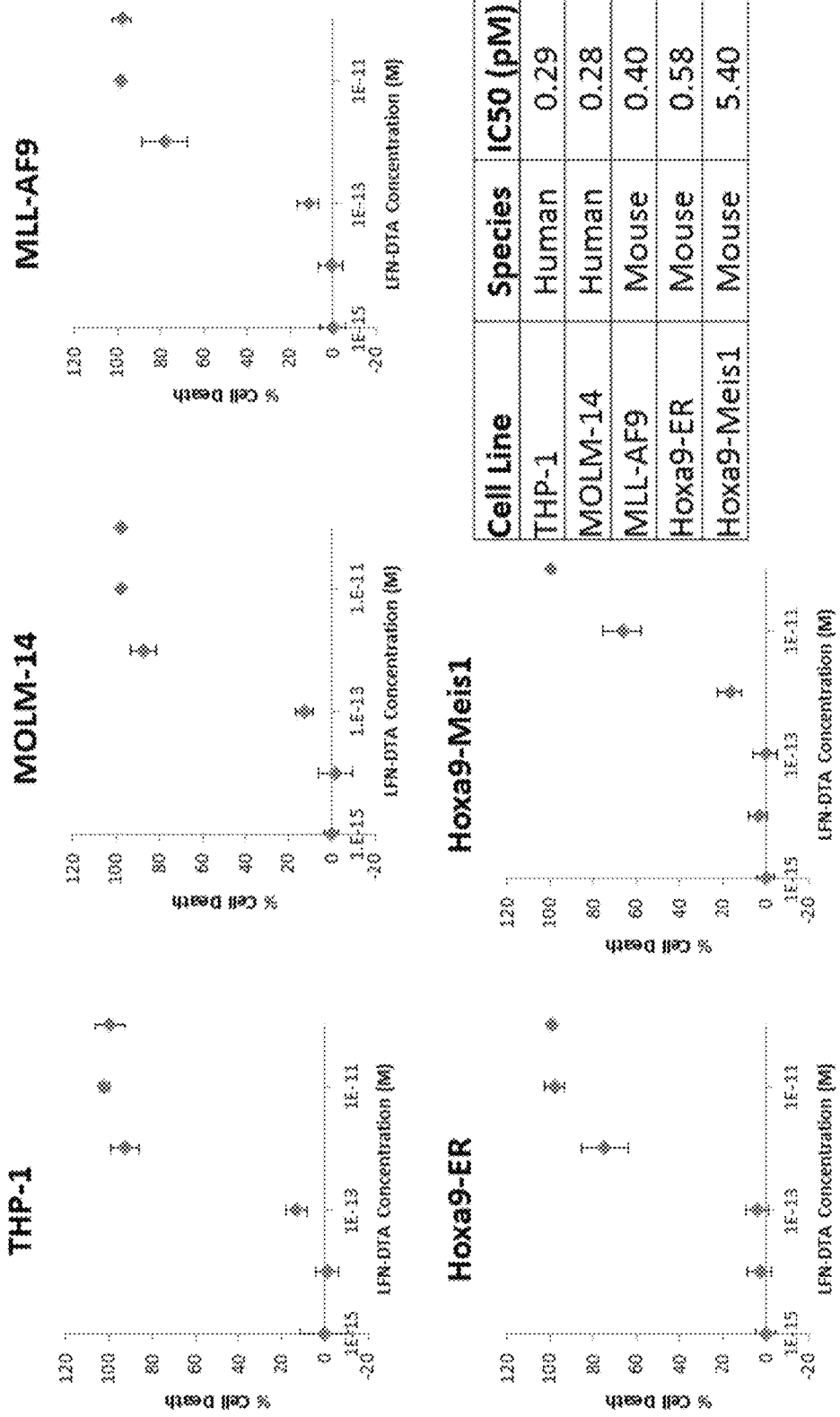
FIG. 37 depicts the activity of LFN-DTA against various hematopoietic cell lines by treating such cells in vitro with various concentrations of LFN-DTA immunotoxin for 48 hours and assessing cell viability using the MTS assay (Promega). As illustrated, the LFN-DTA demonstrated activity against the treated hematopoietic cell lines.
Figure 38:
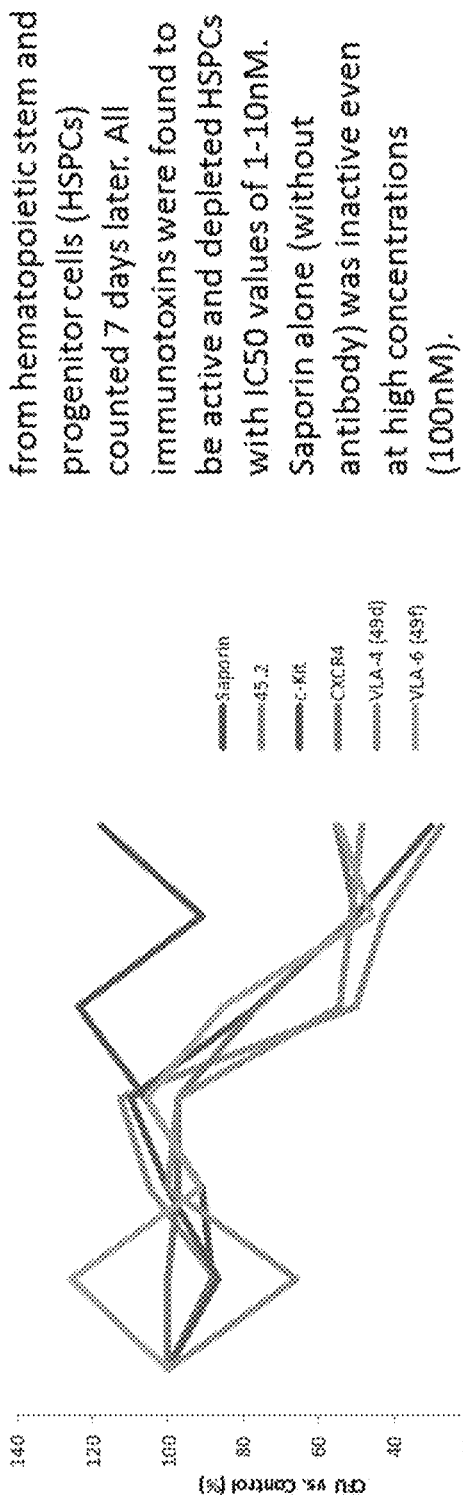
FIG. 38 depicts several conditioning targets or markers. 30,000 whole bone marrow cells in 50 μL IMDM cytokine media treated with various concentrations of immunotoxins or saporin alone for 24 h. Cells were then plated in M3434 methyl cellulose and colonies arising from hematopoietic stem and progenitor cells (HSPCs) counted 7 days later. All immunotoxins were found to be active and depleted HSPCs with $IC_{50}$ values of 1-10 nM. Saporin alone (without antibody) was inactive even at high concentrations (100 nM).

The activity of LFN-DTA against hematopoietic cells was also assessed in various cell lines by treating such cells in vitro with various concentrations of LFN-DTA immunotoxin for 48 hours and cell viability was assessed using MTS assay (Promega). As illustrated in FIG. 37, the LFN-DTA demonstrated activity against the treated cell lines.

Example 14

To investigate whether the conditioning therapies disclosed herein could enable curative transplantation in humans, the present inventors anticipate further evaluating the efficacy of such therapies in one or more human subjects (e.g., an immunocompetent human subject) suffering from sickle cell disease. In particular, the present inventors contemplate administering escalating doses of the immunotoxins disclosed herein to human subjects to evaluate the efficacy of such immunotoxins in conditioning (e.g., depleting or ablating) cells from the subject's target tissues.

The tissues (e.g., bone marrow tissue) of human subjects suffering from or otherwise affected by sickle cell disease would be conditioned by administered to the subjects the immunotoxins (e.g., anti-CD45-SAP immunotoxins) disclosed herein. Following conditioning using the immunotoxins disclosed herein, it is expected that the stem cells from the subject's target tissue would be depleted. Baseline complete blood cell counts (e.g., red blood cell counts, hematocrit and hemoglobin levels), the presence of sickle hemoglobin protein in the blood of the subject and the subject's spleen sizes would then be evaluated prior to, and monitored during and after conditioning therapy.

Following conditioning of the human subjects and dissipation of the immunotoxin from the subject's target tissue, a stem cell population (e.g., an exogenous stem cell population) would be administered, transplanted or otherwise engrafted to the subject's conditioned target tissue. The percent chimerism both prior to and following engraftment would be assessed.

The present inventors anticipate that following administration of the stem cells to the target tissues (e.g., bone marrow tissues) of the subject, a complete normalization of red blood cell, hemoglobin, hematocrit and reticulocyte levels would be observed in the subject and sickle hemoglobin protein in the blood of the subject would be completely replaced with normal hemoglobin protein (e.g., as assessed by native-PAGE analysis). Similarly, it is expected that blood smears obtained post-engraftment will demonstrate a lack of sickle-shaped red blood cells relative to baseline values or a sickle control and spleen sizes would also returned to normal.

As was observed in animal models of disease, it is anticipated that administration of the targeted immunotoxins disclosed herein to human subjects would also avoid the toxicities traditionally associated with current genotoxic conditioning approaches, while preserving innate immunity, thymic integrity and enabling quicker recovery of adaptive immune cells and while avoiding loss of vascular integrity, undesirable anemia, and prolonged cytopenias. Given these advantages, the present inventors anticipate that the foregoing study would demonstrate the efficacy of the immunotoxins and related methods disclosed herein as a means of conditioning human subjects (e.g., non-malignant transplant subjects). The foregoing would also therefore confirm the non-myeloablative nature of the immunotoxins disclosed herein, as well as the ability of the immunotoxins and related methods disclosed herein to fully correct disease in human subjects.

Example 15

Figure 39:
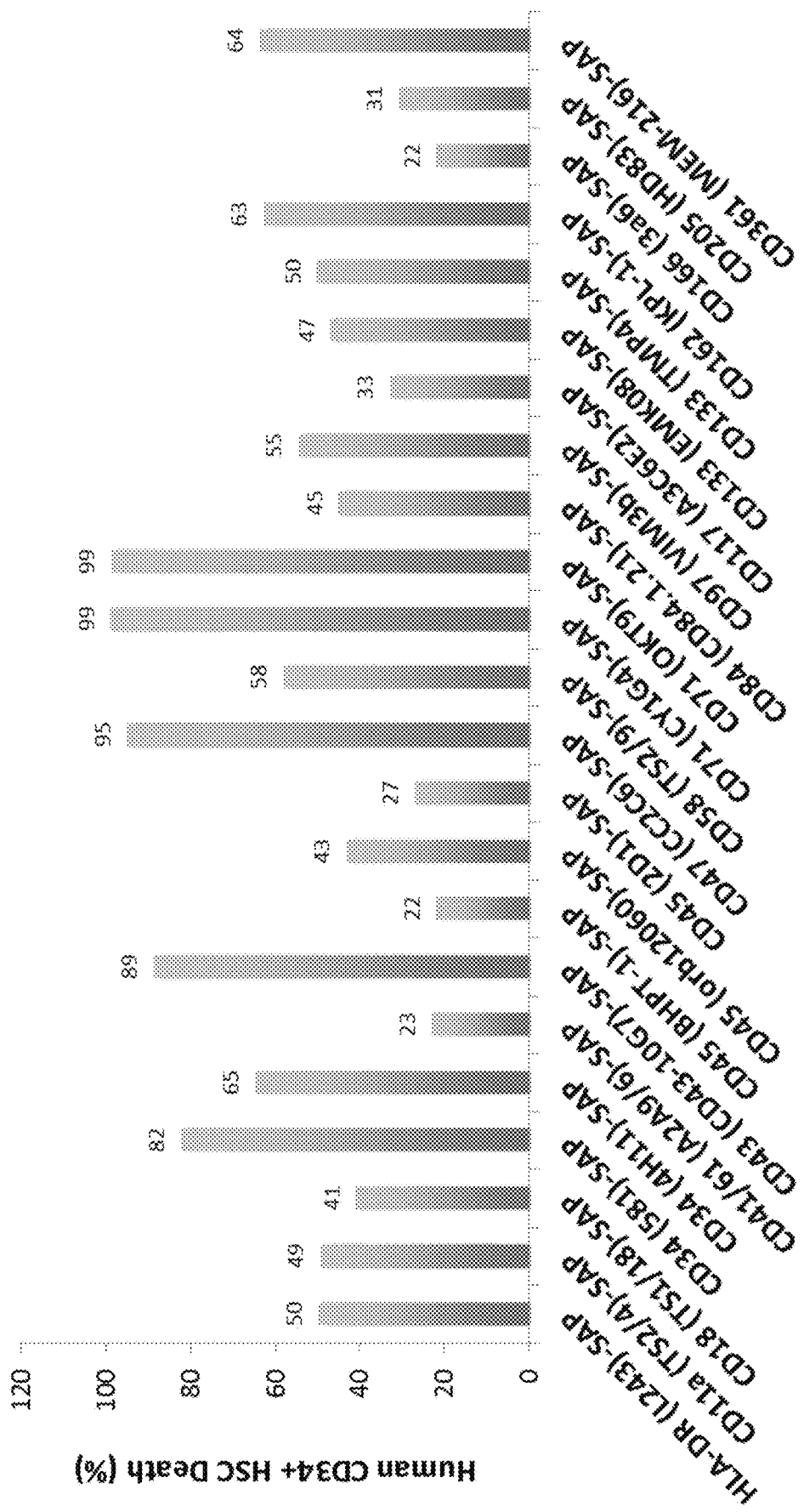
FIG. 39 depicts the results of a human CD34+ hematopoietic stem cell (HSC) killing assay. Immunotoxins were created from saporin and anti-human monoclonal antibodies (mAb) targeting various cell surface receptors and were tested for their ability to kill human bone marrow-derived CD34+ HSC over 5 days and cell viability was assessed using MTS assay. Immunotoxins that killed greater than 20% of the CD34+ cells are shown.

The present inventors conducted a human CD34+ hematopoietic stem cell (HSC) killing assay. Immunotoxins were created using saporin from the listed commercially available anti-human monoclonal antibodies (mAb) and targeting various cell surface receptors and were tested for their ability to kill human bone marrow-derived CD34+ HSC over 5 days. Immunotoxins that killed greater than 20% of the human CD34+ HSCs are shown below in Table 1 below and depicted in FIG. 39.

TABLE 1

Human CD34+ HSC Killing Assay

| mAb Target | mAb Clone | Immunotoxin | mAb concentration (nM) | secondary-toxin | % Cell death |
|---|---|---|---|---|---|
| HLA-DR | L243 | HLA-DR (L243)-SAP | 3 | 3 nM Streptavidin-saporin | 49.68553459 |
| CD11a | TS2/4 | CD11a (TS2/4)-SAP | 3 | 20 nM Fab-saporin | 49.48805461 |
| CD18 | TS1/18 | CD18 (TS1/18)-SAP | 3 | 20 nM Fab-saporin | 40.9556314 |
| CD34 | 581 | CD34 (581)-SAP | 10 | 10 nM Streptavidin-saporin | 82.38 |
| CD34 | 4H11 | CD34 (4H11)-SAP | 3 | 3 nM Streptavidin-saporin | 64.77987421 |
| CD41/61 | A2A9/6 | CD41/61 (A2A9/6)-SAP | 3 | 20 nM Fab-saporin | 23.07692308 |
| CD43 | CD43-10G7 | CD43 (CD43-10G7)-SAP | 10 | 20 nM Fab-saporin | 88.7312187 |
| CD45 | BHPT-1 | CD45 (BHPT-1)-SAP | 3 | 20 nM Fab-saporin | 21.97802198 |
| CD45 | orb12060 | CD45 (orb12060)-SAP | 3 | 20 nM Fab-saporin | 43.3447099 |
| CD45 | 2D1 | CD45 (2D1)-SAP | 3 | 3 nM Streptavidin-saporin | 27.04402516 |
| CD47 | CC2C6 | CD47 (CC2C6)-SAP | 3 | 3 nM Streptavidin-saporin | 94.96855346 |
| CD58 | TS2/9 | CD58 (TS2/9)-SAP | 3 | 20 nM Fab-saporin | 58.24175824 |
| CD71 | CY1G4 | CD71 (CY1G4)-SAP | 3 | 20 nM Fab-saporin | 98.97610922 |
| CD71 | OKT9 | CD71 (OKT9)-SAP | 3 | 20 nM Fab-saporin | 98.9010989 |
| CD84 | CD84.1.21 | CD84 (CD84.1.21)-SAP | 3 | 20 nM Fab-saporin | 45.05119454 |
| CD97 | VIM3b | CD97 (VIM3b)-SAP | 3 | 20 nM Fab-saporin | 54.60750853 |
| CD117 | A3C6E2 | CD117 (A3C6E2)-SAP | 3 | 3 nM Streptavidin-saporin | 33.05785124 |
| CD133 | EMK08 | CD133 (EMK08)-SAP | 10 | 20 nM Mab-saporin | 46.9115192 |
| CD133 | TMP4 | CD133 (TMP4)-SAP | 10 | 20 nM Mab-saporin | 50.16694491 |
| CD162 | KPL-1 | CD162 (KPL-1)-SAP | 3 | 20 nM Fab-saporin | 62.79863481 |
| CD166 | 3a6 | CD166 (3a6)-SAP | 3 | 20 nM Fab-saporin | 21.97802198 |
| CD205 | HD83 | CD205 (HD83)-SAP | 3 | 20 nM Fab-saporin | 30.76923077 |
| CD361 | MEM-216 | CD361 (MEM-216)-SAP | 3 | 20 nM Mab-saporin | 63.58866737 |

The foregoing therefore evidences that the immunotoxins of the present invention demonstrate human CD34+ HSCs killing activity.

Example 16

Figures 40A, 40B:
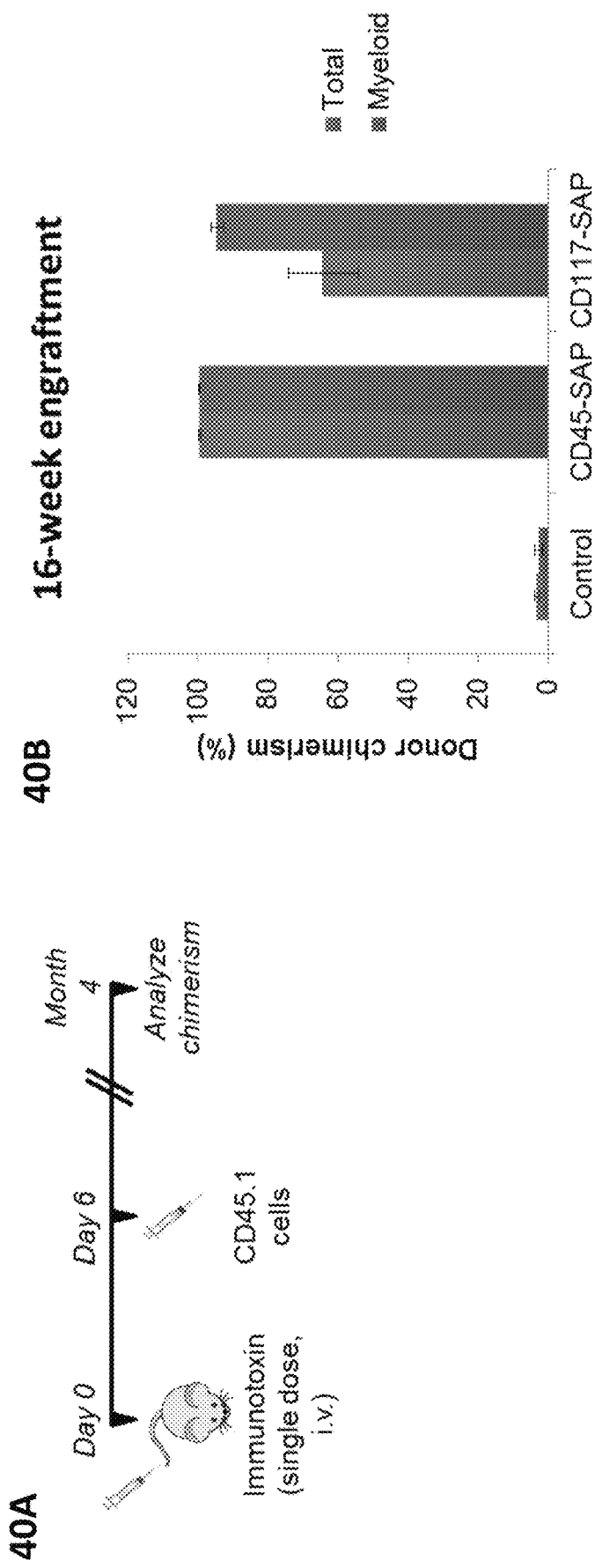
FIGS. 40A-40B depict a transplant study performed in immunocompetent Balb/c mice. 8-week old immunocompetent Balb/c mice were injected with 3 mg/kg CD45-SAP (clone 104) or 1.5 mg/kg CD117-SAP (clone 2B8) and transplanted with 10 million whole bone marrow donor cells 6-days post immunotoxin, as shown in FIG. 40A. Overall total and myeloid-specific donor chimerism was assessed in the peripheral blood of the animals 16-weeks post-transplantation.

The CD45-SAP were prepared and, as generally depicted in FIG. 40A, a transplant study performed in immunocompetent Balb/c mice. 8-week old immunocompetent Balb/c mice were injected with 3 mg/kg CD45-SAP (clone 104) or 1.5 mg/kg CD117-SAP (clone 2B8) and transplanted with 10 million whole bone marrow donor cells 6-days post immunotoxin. Overall total and myeloid-specific donor chimerism was assessed in the peripheral blood of the animals 16-weeks post-transplantation. As illustrated in FIG. 40B, CD45-SAP and CD117-SAP enabled efficient donor cell engraftment in comparison to non-conditioned control mice (at least n=3 mice/group).

Figure 41A:
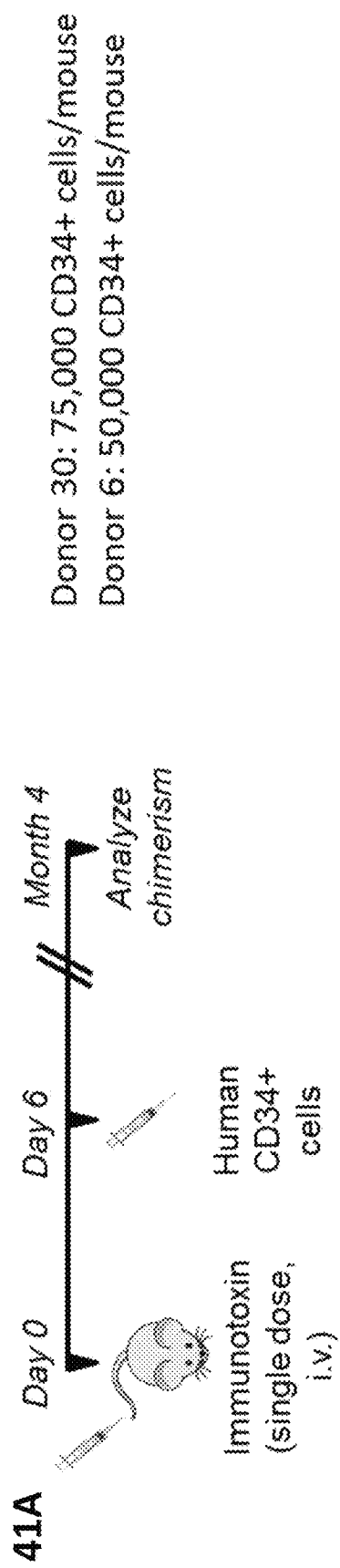
FIGS. 41A-41B illustrate a study performed involving the transplant of human CD34+ donor cells into immunocompromised NSG mice.

The present inventors then performed a study involving the transplant of human CD34+ donor cells into immuno-compromised NSG mice, as illustrated in FIG. 41A. 8 week old immuno-compromised NSG mice were conditioned with 2 Gy irradiation, 3 mg/kg CD45.1-SAP or 1.5 mg/kg CD117-SAP and transplanted with human cord blood CD34+ donor cells 6-days post immunotoxin. Total human donor chimerism was assessed in the peripheral blood 16-weeks post-transplantation, (n=5 mice/group) and is depicted in FIG. 41B.

Figure 41B:
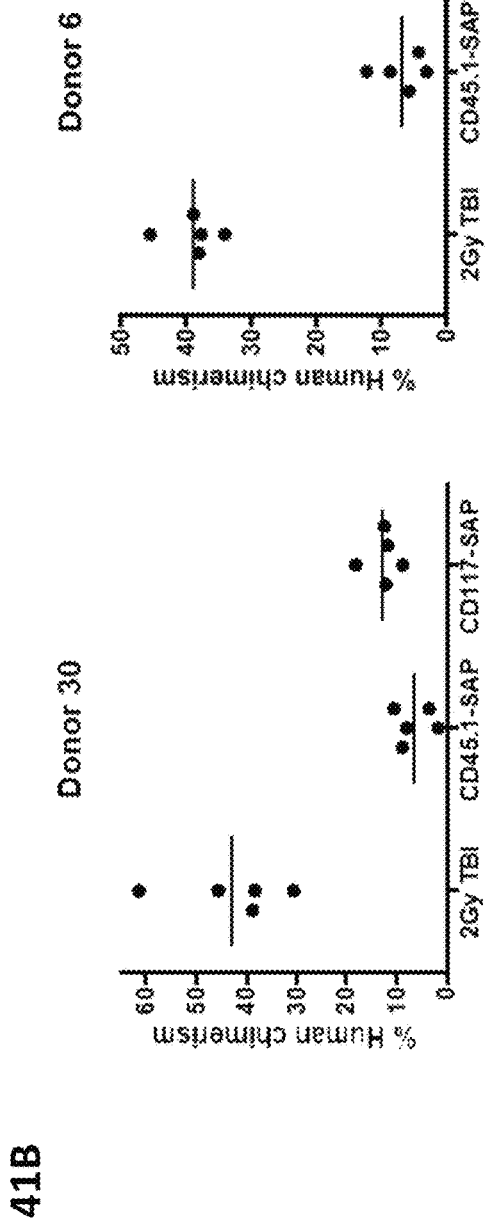
Figures 42A, 42B, 42C:
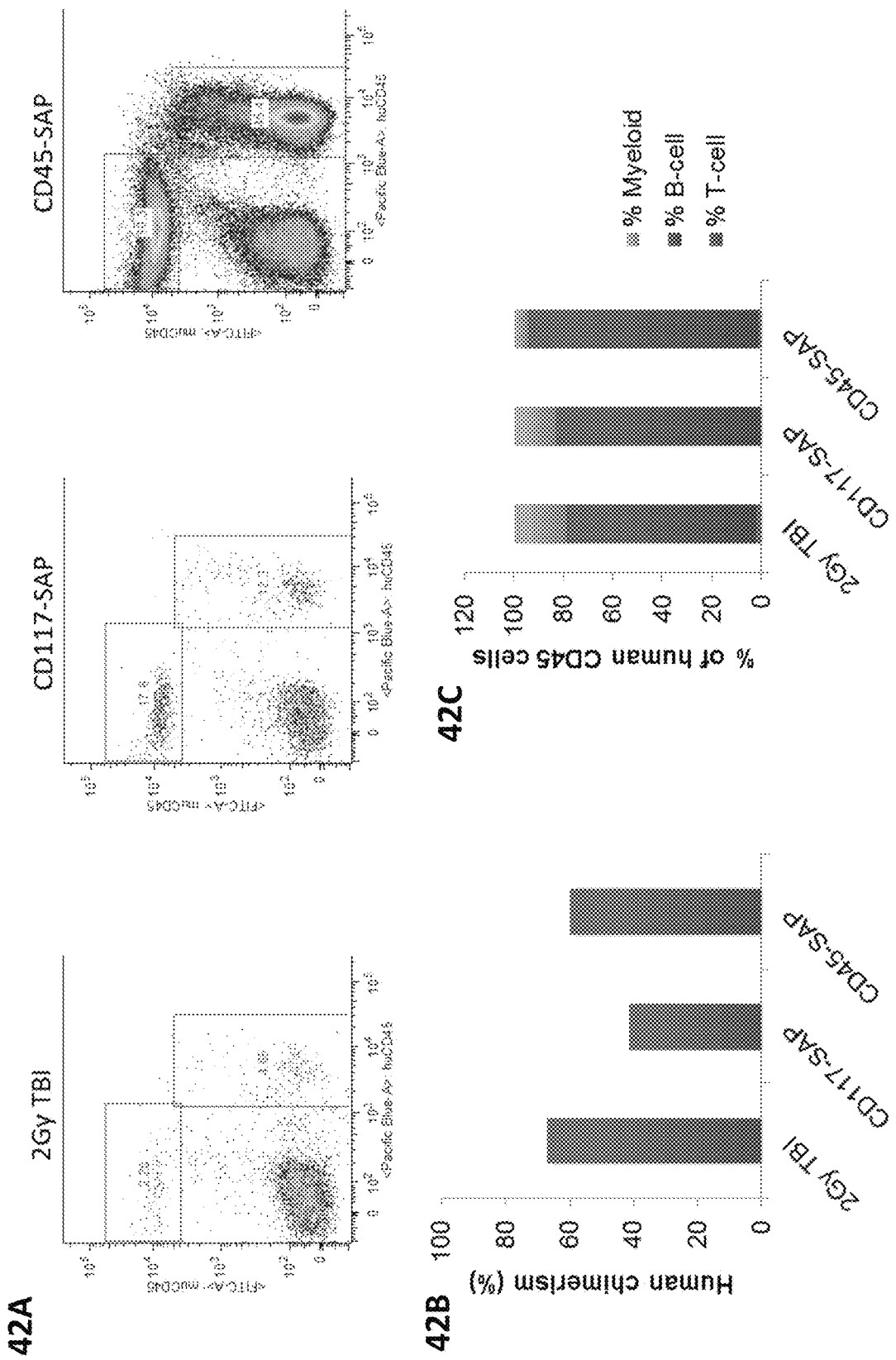
FIGS. 42A-42C illustrate the results of NSG bone marrow human chimerism following conditioning with 2 Gy irradiation, CD117-SAP, or CD45.1-SAP. Conditioning with 2 Gy irradiation, CD117-SAP, or CD45.1-SAP enabled high levels of human engraftment in bone marrow 16-weeks post-transplantation as shown in FIGS. 42A and 42B.

As illustrated in FIG. 41B, FIGS. 42A and 42C, conditioning with 2 Gy irradiation, CD117-SAP, or CD45.1-SAP enabled high levels of human engraftment in bone marrow 16-weeks post-transplantation. As illustrated in FIG. 42C, human donor cells in the bone marrow primarily consisted of B-cells with some myeloid cells and few T-cells.

DISCUSSION

The foregoing results are the first demonstration of an internalizing non-radiolabelled immunotoxin used as a single-entity agent to efficiently condition fully immuno-competent animals for HSCT, and the present inventors believe this is the first example of non-genotoxic conditioning and subsequent HSCT demonstrating disease correction in an animal model. As the CD45 receptor is exclusively expressed by hematopoietic cells, CD45 may be an ideal marker and an immunotoxin target that minimizes toxicity to non-hematopoietic tissues.

The observed lack of neutropenia (as illustrated in FIG. 3B) following conditioning with CD45-SAP and the observed expansion of neutrophils was a surprising result considering neutrophils express CD45. Without wishing to be bound by any particular theory, it may be possible that neutrophils, unlike other blood cells, do not internalize the CD45-SAP or, because of their short life-span (12 hours), that this effect is not visible due to quick turnover of the cell population. It is conceivable that the rapid expansion of neutrophils observed may be a response to CD45+ cell death, as neutrophils are responsible for clearance of apoptotic cells. It is not anticipated that the transient expansion of neutrophils will be an adverse effect, as neutrophils play a prominent role in fighting bacterial infections and their expansion will therefore limit the incidence of bacterial infection, a major cause of traditional conditioning-related mortality.

Although transient lymphopenia in B- and T-cells was observed, it may be that this is necessary (but perhaps not sufficient in itself) for engraftment to occur, as suggested by the ineffectiveness of ACK2 in immunocompetent animals and studies in our lab demonstrating regulatory T-cells directly interact with HSCs in the bone marrow and are necessary for HSC persistence (Fujisaki, J., et al., Nature (2011) 474, 216-219). While T-cell depletion may be an area of concern for HIV patients, the transient nature of depletion may be acceptable on a case-by-case assessment of individual patients (especially prior to development of full-blown AIDS). Also, depletion of recipient T-cells may be advantageous as it would enable clearance of CCR5 positive T-cells which serve as viral reservoirs of HIV. The inventors do not anticipate the transient T-cell depletion to be an issue for the treatment of other hemoglobinopathies and it is important to note that current conditioning regimens fully ablate T-cell and B-cell populations.

The lack of anemia following CD45-SAP conditioning, as evidenced by no decreases in red blood cells, hematocrit or hemoglobin levels, suggests that CD45-SAP conditioning will be relevant to enabling transplantation in anemic conditions (e.g. sickle cell, Diamond-Blackfan anemia and thalassemias).

The use of anti-CD117 antibodies previously explored may target non-hematopoietic CD117+ cells (e.g. cardiac progenitors, gastrointestinal cells, neuronal cells, and cells of the reproductive system). Furthermore, successful conditioning using CD117 antagonists is expected to be limited to immunocompromised patients, and pre-clinical studies suggest this approach may lead to severe neutropenia, thrombocytopenia and anemia: factors that may limit broad utility.

The use of protein immunotoxins offers significant advantages as compared to whole body irradiation, DNA-alkylating agents or radioimmunotherapy (RIT). In addition to the specificity that is achieved by antibody targeting, the requirement for receptor-mediated internalization of protein toxin significantly reduces risks of off-target and by-stander toxicity (e.g. to niche cells). Although anti-CD45 RIT is currently under clinical investigation as a myeloablative alternative to conventional conditioning in acute myeloid leukemia (AML) and myelodysplastic syndrome (MDS) patients, it results in toxicities similar to conventional conditioning including neutropenia, lymphopenia, and thrombocytopenia. In contrast, the foregoing studies demonstrate that targeting CD45 using a protein-based toxin avoids neutropenia, anemia and thymic damage while promoting rapid marrow and peripheral lymphocyte regeneration, presumably by avoiding toxicity to non-target niche cells. Therefore protein-based immunotoxins may be preferred for non-malignant conditions where stable mixed chimerism is sufficient to cure the underlying disease (e.g. hemoglobinopathies and SCID conditions). Additionally, the enhanced stability and cost-effective production of protein-based immunotoxins would likely facilitate widespread use, especially in the countries where hemoglobinopathies are more prevalent. In addition, as protein-based immunotoxins compared to RIT do not induce DNA-damage, they may be better suited to condition pre-malignant Fanconi Anemia patients, who are genetically predisposed to be hyper-sensitive to DNA damaging agents and conventional conditioning.

It is conceivable the proof-of-principle approach used in the foregoing studies may lead to HSC-specific immunotoxins that completely preserve immunity while enabling engraftment. Towards this goal, the foregoing studies offer several considerations. As HSCs are predominantly in a quiescent non-dividing state, it will be of interest to determine whether protein synthesis inhibitor toxins (e.g. saporin, modified ricin analogs, pseudomonas or diphtheria toxin)

are privileged in effecting HSC-depletion as they induce death independent of the cell cycle, in contrast to antimitotic small molecules currently used in antibody-drug conjugates (ADCs). While a previous study suggested CD45 would be an unsuitable target for internalizing immunotoxins due to its poor internalization frequency, the present inventors observed that a 12% internalization is sufficient to achieve potent HSC depletion for in vivo utility. As CD45 is highly expressed with 200,000 molecules per leukocyte, the absolute number of internalized molecules, rather than internalization frequency alone, determines target suitability. Furthermore, in addition to favorable in vivo persistence, high-affinity immunotoxins that minimize shedding and undesirable targeting of donor cells may be required to achieve a wide transplantation window.

Together, the results presented herein support the use and efficacy of an anti-human CD45 and/or CD117-targeting immunotoxin as a less toxic, non-myeloablative conditioning regimen. Moreover, such results surprisingly and unexpectedly validate targeting CD45+ and CD117+ cells as a viable conditioning target and offer distinct advantages and differences (e.g., relative to the CD45 radioimmunotoxin). Such observations are particularly surprising given that monoclonal antibodies targeting CD45 have not previously been considered a viable internalization strategy (Press, et al., *Blood*. (1994), 83(5): 1390-1397). For example, the CD45-targeting immunotoxins disclosed herein are shelf-stable, and would be cost-effective to manufacture, whereas the CD45 radioimmunotoxin has a short half-life (due to radioactive decay) and requires a highly specialized and expensive infrastructure to produce. In stark contrast to the CD45 radioimmunotoxin, which mimics the myeloablative nature of irradiation, the CD45-targeting immunotoxins disclosed herein do not deplete neutrophils and platelets and is therefore expected to minimize patient risk and the need for post-transplantation palliative care.

Furthermore, the methods and compositions disclosed herein selectively target CD45+ and/or CD117+ cells, as internalization is a prerequisite for cell death. In contrast, while CD45 radioimmunotoxin will bind specifically to hematopoietic cells, death is not internalization-dependent and will occur in nearby cells exposed to irradiation (including undesired irradiation to the spleen and liver). Importantly, the radiation-exposed cells, which include cells comprising the niche, are essential for engraftment to proceed (Wang, Y., et al., *Free Radic Biol Med* (2010), 48, 348-356; Wang, Y., et al., *Blood* (2006), 107, 358-366; and Madhusudhan, T., et al., *Stem Cells Dev* (2004), 13, 173-182). Therefore, while the CD45 radioimmunotoxin is suited for BMT in patients with malignancy (e.g., where myeloablative conditioning is necessary to enable 100% donor chimerism), the CD45- and/or CD117-immunotoxins disclosed herein are suitable for treatment of subjects where partial chimerism is sufficient to correct non-malignant disease and minimize the risks during the conditioning procedure. The reduced risk and, the utility of the CD45 and/or CD117 immunotoxins as a single-entity shelf-stable agent, will likely enable more wide-spread use of bone marrow transplant (both allogeneic and gene therapy autologous) even to hospitals that currently lack the infrastructure (e.g. irradiator) or palliative care facilities to perform traditional BMT.

Until now, no non-radiolabelled antibody-based method has successfully conditioned immunocompetent animals and the CD45-SAP, CD117-SAP and related compositions and methods disclosed herein represent the first example of this. Moreover, the ACK2 antibody (antagonist of c-kit receptor) is an example of an antibody approach that only works in immunodeficient mice and fails to condition in immunocompetent animals. Internalizing antibody-immunotoxins in conditioning in any animal has not been previously used.

While the clinical utility of immunotoxins in anti-cancer therapy has largely been limited by issues of immunogenicity and cumulative dose-limiting toxicity, these factors are not applicable to pre-HSC transplant conditioning where non-recurrent use is likely. Furthermore, the wealth of safety data available from previous immunotoxin clinical trials targeting hematological malignancies may in fact facilitate rapid clinical translation. The results presented herein strongly suggest that the CD45-SAP, CD117-SAP or similar protein-based immunotoxins, may be useful in stem cell transplantation to enable the treatment of diseases that are currently limited by toxicities of existing conditioning regimens.

Materials and Methods

General Methods and Statistics

Sample sizes for animal studies (typically n=5 mice/group within each experiment) were based on prior similar work without the use of additional statistical estimations. All statistics were calculated using unpaired student t-test using two-sided analysis except Kaplan-Meier data, which was analyzed by log-rank (Mantel-Cox) test. Alphanumeric coding was used to blind pathology samples and colony forming cell (CFC) counting.

Animals

All animal studies were performed with institutional IACUC approval. Female wild type CD45.2 mice (C57BL/6J), congenic CD45.1 mice (B6.SJL-Ptprca Pepcb/BoyJ), GFP mice (CByJ.B6-Tg(UBC-GFP)30Scha/J), and sickle mice (B6; 129-Hbatm1(HBA)Tow Hbbtm2(HBG1,HBB*)Tow/Hbbtm3(HBG1,HBB)Tow/J were purchased from Jackson Laboratories. Mice were used for experiments at approximately 9 weeks of age, unless stated otherwise. For sickle experiments, sickle chimeras were created by transplanting lethally irradiated (9.5Gy single dose, cesium-137 irradiator, JL Shephard & Associates) 6-week-old C57BL/6J mice with 5 million whole bone marrow (BM) cells harvested from sickle mice. Immunotoxin conditioning and transplantation in sickle chimeras was performed 8 weeks post chimera creation.

Antibodies and Immunotoxin Preparation

Biotinylated anti-CD45 (clone 30-F11), anti-CD45.2 (clone 104), anti-CD49d (clones 9C10), and anti-CD84 (clone mCD84.7) monoclonal antibodies were purchased from BioLegend. Biotinylated anti-CD90 (clone 30-H12), anti-CD133 (clone 13A4), anti-CD184 (clone CD184) and anti-CD135 (clone A2F10) monoclonal antibodies were purchased from eBioscience. Anti-CD117 antagonist antibody (clone ACK2) was purchased from BioLegend and injected at 28 mg/kg. Immunotoxins were prepared by combining biotinylated antibodies (160 kDa MW) with streptavidin-saporin conjugate (135 kDa MW, Advanced Targeting Systems) in a 1:1 molar ratio and subsequently diluted in PBS immediately prior to use. Dose calculations assumed a combined molecular weight of 295 kDa for the immunotoxins. In vivo administration of immunotoxin was performed by intravenous injections (300 μL volume).

In Vitro Cell Death Assay

In vitro cell death experiments involving EL4 (ATCC TIB-39) or EML (ATCC CRL-11691) cells were performed in 96-well plates with 5,000 cells/well plated in 100 μL cell culture media containing various concentrations of immunotoxin. Three independent experiments were performed with three technical replicates within each experiment. EML cells were tested in the presence of 200 ng/mL recombinant murine stem cell factor (R&D Systems). After 72 hours, cell viability was determined using the CellTiter MTS assay (Promega). PBS-treated and 10 μM staurosporine-treated cells (Sigma Aldrich) were used as live and dead controls, respectively.

Measurement of Antibody Internalization

In vitro antibody internalization was assessed as previously described. Briefly, EL4 cells (200,000/mL) in complete media (RPMI w/o phenol red, 10% FBS) were plated into 96-well plates with 20 nM AF488-labelled anti-CD45.2 antibody (clone 104, BioLegend) or a 1:1 mixture of biotinylated anti-CD45.2 antibody and streptavidin-AF488 conjugate (Life Technologies). After 24 hours of incubation, the cells were washed twice and re-suspended in PBS containing 2% FBS. Samples were split into two and one half was incubated with 0.25 mg/mL polyclonal anti-AF488 quenching antibody (clone A-11094, Life Technologies). AF488 signal in samples with and without quenching antibody was quantitated by flow cytometry. Unstained and time zero controls were performed to determine the quenching efficiency and calculate internalization frequency.

In Vivo Antibody Persistence

Mice were i.v. injected with streptavidin-AF488 conjugate premixed with biotinylated anti-CD45 antibody (1:1 ratio in PBS, 1.8 mg/kg). Twenty-four hours post administration, blood, BM and spleen were harvested and AF488 signal determined by flow cytometry. BM cells were co-stained with lineage cocktail (BD Biosciences), anti-cKit and anti-Sca1 antibodies in order to determine AF488 signal within the Lin–cKit+Sca1+ (LKS) progenitor population. AF488 signal in splenocytes and peripheral blood cells was assessed within the CD45+ cell fraction following ex vivo staining with anti-CD45 PeCy7 antibody.

BM Analysis and Transplantation

BM cells for transplantation or analysis were harvested by crushing all limbs or one femur respectively. Total cellularity was determined by complete blood cell counting (CBC) analysis, using an Abaxis VetScan HM5 instrument; and progenitor colony assays were performed following manufacturer's instructions (Stem Cell Technologies). Immunophenotypic stem cell quantification was performed by flow cytometry using lineage antibody cocktail, anti-cKit, anti-Sca1, anti-CD48, and anti-CD150 antibodies and stem cells were defined as Lin–cKit+Sca1+CD48–CD150+. For whole BM transplants, 10 million cells in 300 μL PBS were injected intravenously. For purified stem cells injections, whole BM cells were lineage depleted by magnetic selection (BD Biosciences) prior to FACS sorting of LKS CD48–CD150+ or LKS CD34–CD150+ cells. Two thousand purified stem cells were injected per mouse. Secondary transplants were performed by injecting 1 million BM cells from primary conditioned and transplanted mice (4 months post-transplantation) and injected into secondary lethally irradiated recipients (9.5Gy single dose). Competitive transplants were performed by injecting 1 million BM cells containing a 1:1 ratio of CD45.1 competitor and CD45.2 test cells into lethally irradiated (9.5Gy single dose) congenic CD45.1 recipients.

Peripheral Blood Analysis

Cohorts of mice (typically 4 mice/group) were serially bled or terminally bled by cardiac bleed. White blood cell (WBC), hemoglobin, red blood cell (RBC), platelet and hematocrit levels were quantified by CBC analysis (Abaxis VetScan HM5). For flow cytometry quantification of T-, B- and myeloid cells, blood samples were RBC-lysed and fixed prior to staining with anti-CD45, -B220, -CD3, -Mac1, and -Gr1 antibodies and absolute numbers of T-, B-, myeloid cells were calculated using flow cytometry frequencies and WBC values. Peripheral blood donor chimerism was determined by flow cytometry using anti-CD45.1 and CD45.2 antibodies for transplants involving CD45.1 donor cells. For transplants using CD45.2-GFP donor cells, chimerism was based on GFP+ events within the CD45+ gate. Reticulocyte frequency within the red blood cell population was determined by flow cytometry using thiazole orange staining (Retic-COUNT reagent, BD Biosciences). Native-PAGE analysis of hemoglobin protein was performed on any-kD precast gels (Bio-Rad) using lysed whole blood samples.

Pathology and Histology

At various time points (2, 4, 6, and 8 days post-conditioning) mice were euthanized, fixed in Bouin's solution (Sigma Aldrich) and submitted for necropsy and histology. Two independent experiments were performed with 1 mouse/group. Hematoxylin and eosin staining was performed on paraffin embedded sections of the liver, spleen, femur, kidney, intestinal tract, lymph nodes, thymus and ovaries for assessment of toxicity. Representative images shown are consistent between the two independent experiments.

Intravital Imaging of Vascular Integrity

Live imaging of the mouse calvarial BM vasculature of conditioned mice (2 days post-conditioning) or untreated control mice was performed using a custom made multi-photon microscope (Thorlabs, Inc.) incorporating a high pulse energy fiber based femtosecond laser (Cazadero FLCPA, Calmar laser) with excitation wavelengths set at 775 and 950 nm. A water-immersed 60×/1.00 w objective (LUMPLFLN60XW, Olympus) provided a 415×415 μm field of view and 0.5-5 μm Z-steps were use to a depth of 150-200 μm. Mice were maintained under anesthesia (1.35% isoflurane/oxygen mixture) and body core temperature was maintained using a warmed plate. A U-shaped incision on the scalp exposed the calvarium bone, to which, 2% methocellulose gel was applied for refractive index matching. Second harmonic generation signal (excited at 387.5 nm) was used to visualize bone collagen and to determine a region of interest. On-stage retro-orbital injection of 2 MDa rhodamine-dextran conjugate (150 μL of 3.3 mg/mL D-7139, Life Technologies) was performed and rhodamine signal (585 nm excitation) was continuously recorded (13 frames/second) for the first 2-5 minutes after injection. Serial images were collected up to 30 minutes post-injection. Images taken at similar times post-dextran administration were used for comparison between groups and 2 independent experiments were performed with n=1 mouse/group. Contrast and brightness settings of the images in the figures were adjusted for display purposes only.

Systemic Challenge with *Candida albicans*

*Candida albicans*, wild type stain SC5314 (ATCC MYA-2876), was grown overnight from frozen stocks in yeast extract, peptone, and dextrose (YPD) medium (BD Biosciences) with 100 μg/mL ampicillin (Sigma) in an orbital shaker at 30° C. After pelleting and washing with cold PBS, yeast were counted using a hemocytometer and cell density adjusted in PBS to 75,000 CFUs per 200 μL. Mice were injected via lateral tail vein with 75,000 CFUs and animals were monitored daily. Moribund mice were euthanized humanely.

Quantification of Thymic T-Cell Receptor Excision Circles (TRECs)

TREC quantification was performed as previously described. Briefly, thymi were harvested from non-conditioned mice, 5Gy TBI or CD45-SAP conditioned mice (3 days post-conditioning). Total DNA was extracted using TRIZOL following tissue homogenization in a Bullet Blender Storm BBX24 instrument (Next Advance, Inc.). DNA was quantified by UV-Vis and 1 μg of DNA per sample was used as input for real-time PCR. A standard curve of mouse sjTREC plasmid was used to calculate the absolute number of sjTRECs per sample.

What is claimed is:

1. A method of conditioning a human subject for hematopoietic stem cell engraftment, the method comprising administering to the human subject an amount of an immunotoxin effective to condition bone marrow in the human subject for hematopoietic stem cell engraftment by selectively depleting endogenous hematopoietic stem cells in the bone marrow of the human subject,
wherein the immunotoxin comprises a targeting moiety coupled to a toxin;
wherein the targeting moiety selectively binds to human CD117 or human CD45, and the toxin inhibits protein synthesis;
wherein the immunotoxin is internalized by the endogenous hematopoietic stem cells;
wherein the immunotoxin is capable of conditioning an immunocompetent subject; and
wherein the method does not induce anemia in the human subject prior to hematopoietic stem cell engraftment.

2. The method of claim 1, wherein the immunotoxin is a scFv-toxin conjugate.

3. The method of claim 1, wherein the immunotoxin is a scFv-toxin chimera.

4. The method of claim 1, wherein the toxin inactivates ribosome.

5. The method of claim 1, wherein the toxin is selected from the group consisting of saporin, diphtheria toxin, and ricin A chain.

6. The method of claim 1, wherein the targeting moiety is covalently coupled to the toxin.

7. The method of claim 1, wherein the targeting moiety is noncovalently coupled to the toxin.

8. The method of claim 1, wherein the targeting moiety is selected from the group consisting of an antibody, a Fab, a scFv, a discFv, a biscFv, a tri-scFv, and a tandem scFv.

9. The method of claim 1, wherein the human subject has a hemoglobinopathy.

10. The method of claim 1, wherein the human subject has a thalassemia.

11. The method of claim 1, wherein the human subject has sickle cell disease.

12. The method of claim 1, wherein the targeting moiety is a ligand.

13. The method of claim 12, wherein the ligand is stem cell factor.

14. The method of claim 1, wherein the targeting moiety selectively binds to CD117.

15. The method of claim 1, wherein the targeting moiety selectively binds to CD45.

16. The method of claim 1, wherein the targeting moiety selectively binds to both CD45 and CD117.

17. The method of claim 1, wherein the toxin is of bacterial origin.

18. A method of conditioning a human subject prior to hematopoietic stem cell transplantation, the method comprising administering to the human subject an amount of an immunotoxin effective to condition bone marrow in the human subject for hematopoietic stem cell engraftment by selectively depleting endogenous hematopoietic stem cells in the bone marrow of the human subject,
wherein the immunotoxin comprises a targeting moiety coupled to a toxin;
wherein the targeting moiety selectively binds to human CD117 or human CD45;
wherein the immunotoxin is internalized by the endogenous hematopoietic stem cells;
wherein the immunotoxin is capable of conditioning an immunocompetent subject; and
wherein the method does not induce life-threatening anemia in the human subject prior to hematopoietic stem cell transplantation.

19. The method of claim 18, wherein the targeting moiety is selected from the group consisting of an antibody, a Fab, a scFv, a discFv, a biscFv, a tri-scFv, and a tandem scFv.

20. The method of claim 18, wherein the immunotoxin is a scFv-toxin conjugate.

21. The method of claim 18, wherein the immunotoxin is a scFv-toxin chimera.

22. The method of claim 18, wherein the toxin inactivates ribosome.

23. The method of claim 18, wherein the targeting moiety is covalently coupled to the toxin.

24. The method of claim 18, wherein the toxin is a protein-based bacterial toxin.

25. The method of claim 18, wherein the human subject has a hemoglobinopathy or a thalassemia.

26. The method of claim 18, wherein the human subject has sickle cell disease.

27. A method of conditioning a human subject prior to hematopoietic stem cell transplantation, the method comprising administering to the human subject an amount of an immunotoxin effective to selectively deplete endogenous hematopoietic stem cells in bone marrow of the human subject,
wherein the immunotoxin comprises a targeting moiety coupled to a toxin;
wherein the targeting moiety selectively binds to human CD45 and is selected from the group consisting of an antibody, a Fab, a scFv, a discFv, a biscFv, a tri-scFv, and a tandem scFv;
wherein the toxin inhibits protein synthesis;
wherein the immunotoxin is internalized by the endogenous hematopoietic stem cells;
wherein the immunotoxin is capable of conditioning an immunocompetent subject; and
wherein the method does not induce life-threatening anemia prior to hematopoietic stem cell transplantation.

28. The method of claim 27, wherein the immunotoxin is a scFv-toxin chimera, and the toxin is a protein-based bacterial toxin.

29. A method of hematopoietic stem cell engraftment in a human subject, the method comprising:
administering to the human subject an amount of an immunotoxin effective to condition bone marrow in the human subject for hematopoietic stem cell engraftment by selectively depleting endogenous hematopoietic stem cells in the bone marrow of the human subject,
wherein the immunotoxin comprises a targeting moiety coupled to a toxin, wherein the targeting moiety selectively binds to human CD117 or human CD45, wherein the toxin inhibits protein synthesis, wherein the immunotoxin is internalized by the endogenous hematopoietic stem cells, and wherein the immunotoxin is capable of conditioning an immunocompetent subject; and administering to the human subject exogenous hematopoietic stem cells, wherein the exogenous hematopoietic stem cells engraft in the human subject;

wherein the method does not induce life-threatening anemia in the human subject prior to administration of the exogenous hematopoietic stem cells.

30. The method of claim 29, wherein the method achieves at least about 5-90% donor chimerism in the human subject's bone marrow four months post-administration of the hematopoietic exogenous stem cells.

* * * * *